United States Patent [19]

Cantrell et al.

[11] Patent Number: 5,250,542
[45] Date of Patent: Oct. 5, 1993

[54] PERIPHERALLY SELECTIVE PIPERIDINE CARBOXYLATE OPIOID ANTAGONISTS

[75] Inventors: Buddy E. Cantrell, Fountaintown; Dennis M. Zimmerman, Mooresville, both of Ind.

[73] Assignee: Eli Lilly and Company, Indianapolis, Ind.

[21] Appl. No.: 916,783

[22] Filed: Jul. 17, 1992

Related U.S. Application Data

[63] Continuation of Ser. No. 677,042, Mar. 29, 1991, abandoned.

[51] Int. Cl.$^5$ .............. A61K 31/445; C07D 401/12; C07D 211/32
[52] U.S. Cl. .................. 514/315; 514/316; 514/318; 514/320; 514/331; 546/187; 546/190; 546/193; 546/207; 546/208; 546/209; 546/231; 546/233; 546/234; 546/235; 546/238; 546/316; 546/318; 546/320; 546/331
[58] Field of Search .......... 546/187, 190, 193, 207, 546/208, 209, 231, 233, 234, 235, 238, 316, 318, 320, 331; 514/315, 316, 318, 320, 331

[56] References Cited

U.S. PATENT DOCUMENTS

| | | | |
|---|---|---|---|
| 3,498,978 | 2/1970 | Clark et al. | 546/208 |
| 3,884,916 | 5/1975 | Janssen et al. | |
| 3,936,468 | 1/1976 | Yamamoto et al. | 546/236 |
| 3,954,779 | 3/1976 | Smith et al. | 546/248 |
| 3,991,199 | 9/1976 | Berger | 546/238 |
| 4,081,450 | 4/1978 | Zimmerman | 546/233 |
| 4,115,400 | 11/1978 | Zimmerman | 546/233 |
| 4,141,980 | 4/1979 | Berger | 546/238 |
| 4,175,197 | 7/1979 | Zimmerman | 546/233 |
| 4,191,771 | 11/1980 | Zimmerman | 546/238 |
| 4,284,635 | 3/1981 | Zimmerman | 546/238 |
| 4,581,456 | 6/1986 | Barnett | 546/238 |
| 4,663,460 | 7/1987 | Barnett | 546/233 |
| 4,788,283 | 2/1988 | Karrer | 546/187 |
| 4,891,379 | 3/1990 | Zimmerman et al. | 514/315 |
| 4,992,450 | 7/1991 | Zimmerman et al. | 514/315 |
| 5,086,054 | 2/1992 | Parish | 546/208 |
| 5,159,081 | 10/1992 | Cantrell et al. | |

FOREIGN PATENT DOCUMENTS 428434 6/1990 European Pat. Off. ............ 546/315

OTHER PUBLICATIONS

"New Structural Concepts for Narcotic Antagonist Defined in a 4-Phenylpiperidine Series", of Zimmerman, et al., Nature, 275, No. 5678, pp. 332-334 (1978).
"Selective Opioid Receptor Agonist and Antagonist; Research Tools and Potential Therapeutic Agents", J. Med. Chem., 1990, 33, 895-902 of Zimmerman, et al.
Leander, et al., in the paper "Novel Phenylpiperidine Opioid Antagonist and Partial Antagonists; Effects on Fluid Consumption", European Journal of Pharmacology, 81, 185-192 (1982).
Oh-ishi, et al., Journal of Medicinal Chemistry, 1973, vol. 16, 12, 1376-1378.
Leander, et al., in the paper entitled "Antagonism of Bremazocine-Induced Urination as a Test for Kappa-Opioid Receptor Antagoinists Within the Phenylpiperidine Series", Drug Development Research 4, 421-427 (1984).
Baile, et al., in a paper entitled "Opiate Antagonists and Agonists and feeding in Sheep", Philsiology and Behavior, 26, 1019-23 (1981).
Leander in a paper entitled "A Kappa Opioid Affect; Increased Urination in the Rat", The Journal of Pharmacology and Therapeutics 224, No. 1, 89-94 (1983).
B. Huegi, et al., Eur. J. Med. Chem.-Chim. Ther. 1934-19, No. 6, pp. 487-494.

Primary Examiner—C. Warren Ivy
Assistant Examiner—Raymond Covington
Attorney, Agent, or Firm—MaCharri R. Vorndran-Jones; Leroy Whitaker

[57] ABSTRACT

3,4,4-trisubstitutedpiperidinyl-N-alkylcarboxylates and intermediates for their preparation are provided. These piperidine-N-alkylcarboxylates are useful as peripheral opioid antagonists.

40 Claims, No Drawings

PERIPHERALLY SELECTIVE PIPERIDINE CARBOXYLATE OPIOID ANTAGONISTS

This application is a continuation of application Ser. No. 07/677,042, filed Mar. 29, 1991 abandoned.

FIELD OF THE INVENTION

This invention relates to 3,4,4-trisubstituted-piperidinyl-N-alkyl-carboxylates and their methods of use as peripheral opioid antagonists.

BACKGROUND OF THE INVENTION

A substantial body of evidence indicates that peripheral opioid peptides and their receptors have a major physiological role in the regulation of gut motility. Consequently gastrointestinal disorders such as idiopathic constipation and irritable bowel syndrome may relate to a dysfunction of opioid receptor mediated control and, agents which act as antagonists for these receptors may benefit a patient suffering from such a dysfunction.

Natural and synthetic opiates such as morphine have been used extensively in the mediation of pain. However, these agents can produce undesirable side effects such as constipation, nausea, and vomiting which are peripheral to the desired action as analgesics. Thus, a peripheral opioid antagonist should not substantially affect the analgesic effects of the opiate while acting to control gastrointestinal function and to minimize the undesirable side effects of the narcotic drug.

A number of opioid antagonists have been reported including naloxone and naltrexone (Blumberg et al., *Toxicol Appl. Pharmacol.*, 10, 406, 1967). Other derivatives of these compounds have been recently reported (Portoghese et al., *J. Med. Chem.*, 31, 281-282, 1988). 4-Arylpiperidines have also been reported as having analgesic activity and in some instances acting as narcotic antagonists Zimmerman U.S. Pat. No. 4,191,771 (1980); Barnett U.S. Pat. No 4,581,456 (1986); Zimmerman U.S. Pat. No. 4,081,450 (1978) These compounds are disclosed as having useful analgesic activity and in some cases acting as potent narcotic antagonists.

It would be advantageous to have compounds which would act as antagonists to the peripheral effects of opiate analgesics and endogenous opioid peptides. It would also be advantageous if these compounds had a minimal effect on the analgesic activity of the opiate drugs. It would be further advantageous to have compounds which can act to minimize the effects of idiopathic constipation and irritable bowel syndrome.

It has now been found that the N-substituted piperidines of the instant invention are useful as peripherally selective opioid antagonists. The instant compounds can also be useful in relieving the symptoms of idiopathic constipation and irritable bowel syndrome. Certain of the instant compounds are also useful as intermediates in preparing new piperidine compounds.

SUMMARY OF THE INVENTION

The present invention relates to the trans-3,4-isomer of a compound of the Formula wherein:
$R^1$ is hydrogen or $C_1$-$C_5$ alkyl;
$R^2$ is hydrogen, $C_1$-$C_5$ alkyl or $C_2$-$C_6$ alkenyl;
$R^3$ is hydrogen, $C_1$-$C_{10}$ alkyl, $C_3$-$C_{10}$ alkenyl, phenyl, cycloalkyl, $C_5$-$C_8$ cycloalkenyl, cycloalkyl-substituted $C_1$-$C_3$ alkyl, $C_5$-$C_8$ cycloalkenyl-substituted $C_1$-$C_3$ alkyl, or phenyl-substituted $C_1$-$C_3$ alkyl;
A is $OR^4$ or $NR^5R^6$; wherein:
$R^4$ is hydrogen, $C_1$-$C_{10}$ alkyl, $C_2$-$C_{10}$ alkenyl, cycloalkyl, $C_5$-$C_8$ cycloalkenyl, cycloalkyl-substituted $C_1$-$C_3$ alkyl, $C_5$-$C_8$ cycloalkenyl-substituted $C_1$-$C_3$ alkyl or phenyl-substituted $C_1$-$C_3$ alkyl;
$R^5$ is hydrogen or $C_1$-$C_3$ alkyl;
$R^6$ is hydrogen, $C_1$-$C_{10}$ alkyl, $C_3$-$C_{10}$ alkenyl, cycloalkyl, phenyl, cycloalkyl-substituted $C_1$-$C_3$ alkyl, $C_5$-$C_8$ cycloalkenyl, $C_5$-$C_8$ cycloalkenyl-substituted $C_1$-$C_3$ alkyl, phenyl-substituted $C_1$-$C_3$ alkyl, or $(CH_2)_q$-B; or
$R^5$ and $R^6$ are each $CH_2$ which together with N form a 4 to 6 membered heterocyclic ring; wherein B is B is an isoxazole ring ,CW or $NR^7R^8$;

or $NR^7R^8$; wherein:
$R^7$ is hydrogen or $C_1$-$C_3$ alkyl;
$R^8$ is hydrogen, $C_1$-$C_{10}$ alkyl, $C_3$-$C_{10}$ alkenyl, cycloalkyl-substituted $C_1$-$C_3$ alkyl, cycloalkyl, $C_5$-$C_8$ cycloalkenyl, $C_5$-$C_8$ cycloalkenyl-substituted $C_1$-$C_3$ alkyl, phenyl or phenyl-substituted $C_1$-$C_3$ alkyl; or
$R^7$ and $R^8$ are each $CH_2$ which together with N form a 4 to 6 membered heterocyclic ring;
W is $OR^9$, $NR^{10}R^{11}$, or OE; wherein
$R^9$ is hydrogen, $C_1$-$C_{10}$ alkyl, $C_2$-$C_{10}$ alkenyl, cycloalkyl, $C_5$-$C_8$ cycloalkenyl, cycloalkyl-substituted $C_1$-$C_3$ alkyl, $C_5$-$C_8$ cycloalkenyl-substituted $C_1$-$C_3$ alkyl or phenyl-substituted $C_1$-$C_3$ alkyl;
$R^{10}$ is hydrogen or $C_1$-$C_3$ alkyl;
$R^{11}$ is hydrogen, $C_1$-$C_{10}$ alkyl, $C_3$-$C_{10}$ alkenyl, phenyl, cycloalkyl, $C_5$-$C_8$ cycloalkenyl, cycloalkyl-substituted $C_1$-$C_3$ alkyl, $C_5$-$C_8$ cycloalkenyl-substituted $C_1$-$C_3$ alkyl, phenyl-substituted $C_1$-$C_3$ alkyl or $$\overset{O}{\underset{CY}{\|}};$$

or
$R^{10}$ and $R^{11}$ are each $CH_2$ which together with N form a 4 to 6 membered hetercyclic ring;
E is

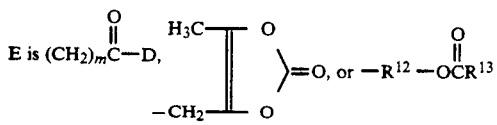

wherein
R$^{12}$ is C$_1$-C$_3$ alkyl substituted methylene,
R$^{13}$ is C$_1$-C$_{10}$ alkyl;
D is OR$^{14}$ or NR$^{15}$R$^{16}$;
wherein:
R$^{14}$ is hydrogen, C$_1$-C$_{10}$ alkyl, C$_2$-C$_{10}$ alkenyl, cycloalkyl, C$_5$-C$_8$ cycloalkenyl, cycloalkyl-substituted C$_1$-C$_3$ alkyl, C$_5$-C$_8$ cycloalkenyl-substituted C$_1$-C$_3$ alkyl, or phenyl-substituted C$_1$-C$_3$ alkyl;
R$^{15}$ is hydrogen, C$_{10}$-C$_{10}$ alkyl, C$_3$-C$_{10}$ alkenyl, phenyl, phenyl-substituted C$_1$-C$_3$ alkyl, cycloalkyl, C$_5$-C$_8$ cycloalkenyl, cycloalkyl-substituted C$_1$-C$_3$ alkyl or C$_5$-C$_8$ cycloalkenyl-substituted C$_1$-C$_3$ alkyl;
R$^{16}$ is hydrogen or C$_1$-C$_3$ alkyl; or
R$^{15}$ and R$^{16}$ are each CH$_2$ which together with N form a 4 to 6 membered heterocyclic ring;
Y is OR$^{17}$ or NR$^{18}$R$^{19}$;
wherein:
R$^{17}$ is hydrogen, C$_1$-C$_{10}$ alkyl, C$_2$-C$_{10}$ alkenyl, cycloalkyl, C$_5$-C$_8$ cycloalkenyl, cycloalkyl-substituted C$_1$-C$_3$ alkyl, C$_5$-C$_8$ cycloalkenyl-substituted C$_1$-C$_3$ alkyl, or phenyl-substituted C$_1$-C$_3$ alkyl;
R$^{18}$ is hydrogen or C$_1$-C$_3$ alkyl;
R$^{19}$ is hydrogen, C$_1$-C$_{10}$ alkyl, C$_3$-C$_{10}$ alkenyl, phenyl, cycloalkyl, C$_5$-C$_8$ cycloalkenyl, cycloalkyl-substituted C$_1$-C$_3$ alkyl, C$_5$-C$_8$ cycloalkenyl-substituted C$_1$-C$_3$ alkyl, or phenyl-substituted C$_1$-C$_3$ alkyl; or
R$^{18}$ and R$^{19}$ are each CH$_2$ which together with N form a 4 to 6 membered heterocyclic ring;
n is 0-4;
q is 1-4;
m is 1-4;
or pharmaceutically acceptable salts thereof.

The present invention also provides a method for using an effective amount of the compounds of the instant invention to treat constipation, nausea or vomiting induced by the use of opiates in a patient.

In a further embodiment the instant invention provides a method for treating the symptoms of idiopathic constipation or irritable bowel syndrome.

In another embodiment the instant invention provides pharmaceutical formulations comprising an effective amount of a compound of the instant invention in combination with a pharmaceutically acceptable excipient.

DETAILED DESCRIPTION OF THE INVENTION

The term "C$_1$-C$_5$ alkyl", as used herein, represents a branched or linear alkyl group having from one to five carbon atoms. Typical C$_1$-C$_5$ alkyl groups include methyl, ethyl, n-propyl, iso-propyl, butyl, iso-butyl, sec-butyl, tert-butyl, pentyl and the like. Other such terms represent straight chain or branched alkyl groups of the specified number of carbon atoms, e.g. "C$_1$-C$_3$ alkyl" represents methyl, ethyl, n-propyl and isopropyl.

The terms "C$_2$-C$_6$ alkyenyl", "C$_2$-C$_{10}$ alkenyl" and "C$_3$-C$_{10}$ alkenyl" refer to groups containing 2 to 6, 2 to 10, and 3 to 10 carbon atoms respectively and one double bond. The group can be branched or straight chain. Examples of such groups include 2-propenyl (—CH$_2$—CH=CH$_2$), 1-butanyl (—CH=CHCH$_2$CH$_3$) and the like.

The term "cycloalkyl" represents C$_3$-C$_8$ cycloalkyl groups such as cyclopropyl, cyclobutyl, cyclopentyl, cyclohexyl, cycloheptyl and cyclooctyl. "Substituted C$_5$-C$_6$ cycloalkyl" includes cycloalkyl groups substituted with C$_1$-C$_3$ alkyl, C$_1$-C$_3$ alkoxyl or halo.

The term "cycloalkyl-substituted C$_1$-C$_3$ alkyl" represents a linear C$_1$-C$_3$ alkyl group substituted at a terminal carbon with a C$_3$-C$_8$ cycloalkyl group. Typical cycloalkyl-substituted alkyl groups include cyclohexylmethyl, cyclohexylethyl, cyclopentylethyl, cyclopentylpropyl and the like.

The term "C$_5$-C$_8$ cycloalkenyl" represents and olefinically unsaturated cyclic ring having five to eight carbon atoms.

The term "phenylalkyl" represents a linear C$_1$-C$_3$ alkyl chain substituted at a terminal carbon with a substituted or unsubstituted benzene ring. Typical phenylalkyl groups include phenylmethyl, phenylethyl and 3-(4-methylphenyl)propyl.

The term "phenyl" includes a benzene ring as well as a benzene ring substituted with one or two C$_1$-C$_2$ alkyl groups.

The "4 to 6-membered N-containing heterocyclic ring" referred to herein includes aromatic and nonaromatic rings such as pyrroles and piperidines.

While all of the compounds of the present invention are useful peripheral opioid antagonists, certain of the present compounds are preferred for that use. Preferred compounds of Formula I are those in which R$^1$ is hydrogen, R$^2$ is methyl; R$^3$ is cyclohexyl, cyclohexylmethyl, phenyl or benzyl; n is 1 or 2; A is OH or NH(CH$_2$)$_x$C(O)W where x is 1 to 3; and W is OR$^9$, NHR$^{11}$ or —OR$^{12}$—O—C(O)R$^{13}$; wherein R$^9$ is hydrogen, C$_1$-C$_5$ alkyl, benzyl, or substituted-cyclohexyl; R$^{11}$ is hydrogen or C$_1$-C$_5$ alkyl; R$^{12}$ is C$_1$-C$_3$ alkyl substituted methylene; and R$^{13}$ is C$_1$-C$_3$ alkyl.

Certain of the compounds of the instant invention can serve as intermediates in the preparation of other compounds of the invention. Compounds which are preferred are those in Formula I in which R$^1$ is hydrogen or CH$_3$; R$^2$ is CH$_3$; R$^3$ is cyclohexyl, cyclohexylmethyl, benzyl, or phenyl; A is OH, methoxy or ethoxy; and n is 1 or 2.

The piperidines of the invention as illustrated in Formula I can occur as the trans and cis stereochemical isomers by virtue of the substituents at the 3- and 4-positions of the piperidine ring. The term "trans" as used herein refers to R$^2$ in position 3 being on the opposite side from the methyl group in position 4, whereas in the "cis" isomer R$^2$ and the 4-methyl are on the same side of the ring. The present invention contemplates the individual stereoisomers as well as racemic mixtures. In the most preferred compounds of the present invention, the group R$^2$ at the 3-position is situated on the opposite side of the ring, i.e., trans to the methyl group in the 4-position and on the same side of the ring, i.e., Zusammen or Z, relative to the higher priority phenyl group at the 4-position. These trans or Z-isomers can exist as the 3R,4R-isomer as shown in Formula II

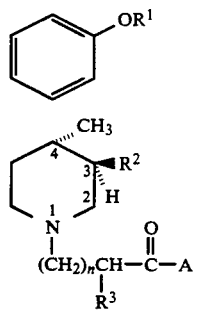

or the 3S,4S-isomer of Formula III

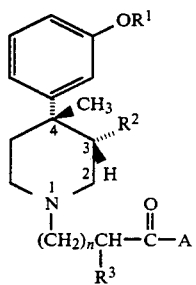

The terms "R" and "S" are used herein as commonly used in organic chemistry to denote specific configuration of a chiral center. The term "R" refers to "right" and refers that configuration of a chiral center with a clockwise relationship of group priorities (highest to second lowest) when viewed along the bond toward the lowest priority group. The term "S" or "left" refers to that configuration of a chiral center with a counterclockwise relationship of group priorties (highest to second lowest) when viewed along the bond toward the lowest priority group. The priority of groups is based upon their atomic number (heaviest isotope first). A partial list of priorities and a discussion of stereo chemistry is contained in the book: *The Vocabulary of Organic Chemistry*, Orchin, et al., John Wiley and Sons Inc., publishers, page 126, which is incorporated herein by reference.

The preferred compounds of the present invention are those of Formula I in which the configuration of substituents on the piperidine ring is 3R and 4R.

When $R^3$ is not hydrogen, the carbon atom attached to $R^3$ is asymmetric. As such, this class of compounds can further exist as the individual R or S stereoisomers at this chiral center, or the racemic mixture of the isomers, and all are contemplated within the scope of the present invention. Preferably, a substantially pure stereoisomer of the compounds of this invention is used, i.e., an isomer in which the configuration at the chiral center is R or S, i.e., those compounds in which the configuration at the three chiral centers is preferably 3R, 4R, S or 3R, 4R, R.

Furthermore, other asymmetric carbons can be introduced into the molecule depending on the structure of A. As such, these classes of compounds can exist as the individual R or S stereoisomers at these chiral centers, or the racemic mixture of the isomers, and all are contemplated as within the scope of the present invention.

Preferred compounds of the instant invention include the following:

U-OCH$_2$CH$_3$; U-OH; G-OH; U-NHCH$_2$C(O)NHCH$_3$; U-NHCH$_2$C(O)NH$_2$; G-NHCH$_2$C(O)NHCH$_3$; U-NHCH$_2$C(O)NHCH$_2$CH$_3$; G-NH(CH$_2$)$_3$C(O)OCH$_2$CH$_3$; G-NHCH$_2$C(O)OH; M-NHCH$_2$C(O)NH$_2$; M-NH(CH$_2$)$_2$C(O)OCH$_2$(C$_6$H$_5$); X-OCH$_2$CH$_3$; X-OH; X-NH(CH$_2$)$_2$CH$_3$; Z-NH(CH$_2$)$_3$C(O)OCH$_2$CH$_3$; X-NHCH$_2$C(O)OH; Z-NH(CH$_2$)$_2$N(CH$_3$)$_2$; Z-NH(CH$_2$)$_2$C(O)NHCH$_2$CH$_3$; X-OCH$_2$(C$_6$H$_5$); X-N(CH$_3$)$_2$; Z-NH(CH$_2$)$_3$C(O)NHCH$_3$; Z-NH(CH$_2$)$_3$C(O)NH$_2$; Z-NH(CH$_2$)$_3$C(O)NHCH$_2$CH$_3$; X-OCH$_2$C(O)OCH$_3$; X-OCH$_2$C(O)NHCH$_3$; and X-N(CH$_3$)CH$_2$C(O)CH$_2$CH$_3$; in which:

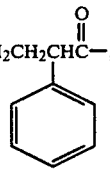

U represents Q—CH$_2$CH$_2$CHC—,

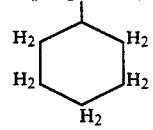

G represents Q—CH$_2$CH$_2$CHC—;

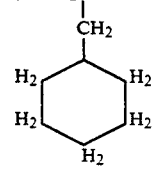

M represents Q—CH$_2$CH—C—;

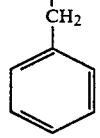

Z represents Q—CH$_2$CHC—;

$$X \text{ represents } Z-NHCH_2\overset{O}{\underset{\|}{C}}-;$$

wherein:

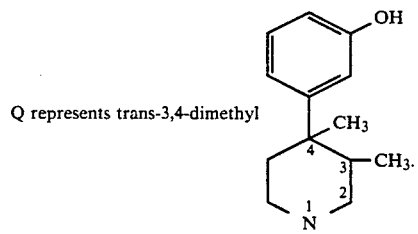

Q represents trans-3,4-dimethyl

Particularly preferred compounds of the instant invention include the following:

Z-OH; Z-NH(CH$_2$)$_2$C(O)OH; G-NH(CH$_2$)$_2$C(O)NH$_2$; G-NH(CH$_2$)$_2$C(O)NHCH$_3$; G-NHCH$_2$C(O)NH$_2$; G-NHCH$_2$C(O)NHCH$_2$CH$_3$; G-NH(CH$_2$)$_3$C(O)NHCH$_3$; G-NH(CH$_2$)$_2$C(O)OH; G-

NH(CH$_2$)$_3$C(O)OH; X-NH$_2$; X-NHCH(CH$_3$)$_2$; X-OCH$_2$CH(CH$_3$)$_2$; X-OCH$_2$C$_6$H$_5$; X-OH; X-O(CH$_2$)$_4$CH$_3$; X-O-(4-methoxycyclohexyl); X-OCH(CH$_3$)OC(O)CH$_3$; X-OCH$_2$C(O)NHCH$_2$(C$_6$H$_5$); M-NHCH$_2$C(O)OH; M-NH(CH$_2$)$_2$C(O)OH; M-NH(CH$_2$)$_2$C(O)NH$_2$; U-NHCH$_2$C(O)OCH$_2$CH$_3$; and U-NHCH$_2$C(O)OH; wherein Z, G, X and U are as defined above.

The compounds of the instant invention can be named in several ways. For example the compound with the structure IIa

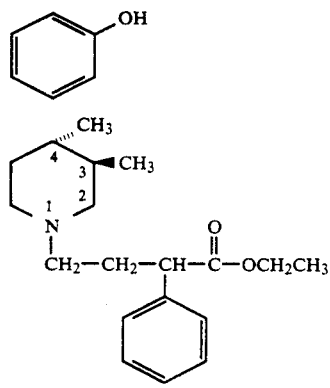

can be named trans-4-(3-hydroxyphenyl)-3,4-A-phenyl-1-piperidine butanoic acid, ethyl ester or ethyl-trans-4-[4-(3-hydroxyphenyl)-3,4-dimethyl-1piperidinyl]-2-phenylbutanoate.

The piperidines of this invention form pharmaceutically acceptable acid addition salts with a wide variety of inorganic and organic acids. Typical acids used include sulfuric, hydrochloric, hydrobromic, phosphoric, hypophosphoric, hydroiodic, sulfamic, citric, acetic, maleic, malic, succinic, tartaric, cinnamic, benzoic, ascorbic, mandelic, p-toluenesulfonic, benzenesulfonic, methanesulfonic, trifluoroacetic, hippuric and the like.

The compounds of the present invention can be prepared by a variety of procedures well known to those of ordinary skill in the art. The 3-substituted-4-methyl-4-(3-hydroxy- or alkanoyloxyphenyl)piperidine derivatives employed as starting materials in the synthesis of the instant compounds can be prepared by the general procedure taught by Zimmerman in U.S. Pat. No. 4,115,400 (1978), and Zimmerman et al. in U.S. Pat. No. 4,891,379 (1990) both incorporated herein by reference The starting material for the synthesis of the compounds of the present invention, (3R,4R)-4-(3-hydroxypheny)-3,4-dimethylpiperidine, can be prepared by the procedure of Barnett in U.S. Pat. 4,581,456, herein incorporated by reference, but adjusted as described in such patent so that the $\beta$-stereochemistry is preferred. This process is depicted in Scheme 1, wherein R$^{20}$ is C$_1$-C$_3$ alkyl, R$^{21}$ is C$_1$-C$_6$ alkyl, R$^{22}$ is C$_1$-C$_4$ alkyl; R$^{23}$ and R$^{24}$ independently are C$_1$-C$_3$ alkyl or, when taken together with the nitrogen atom to which they are attached, form piperidine, piperazine, N-methylpiperazine, morpholine or pyrrolidine, and J is halogen, preferably chlorine or bromine.

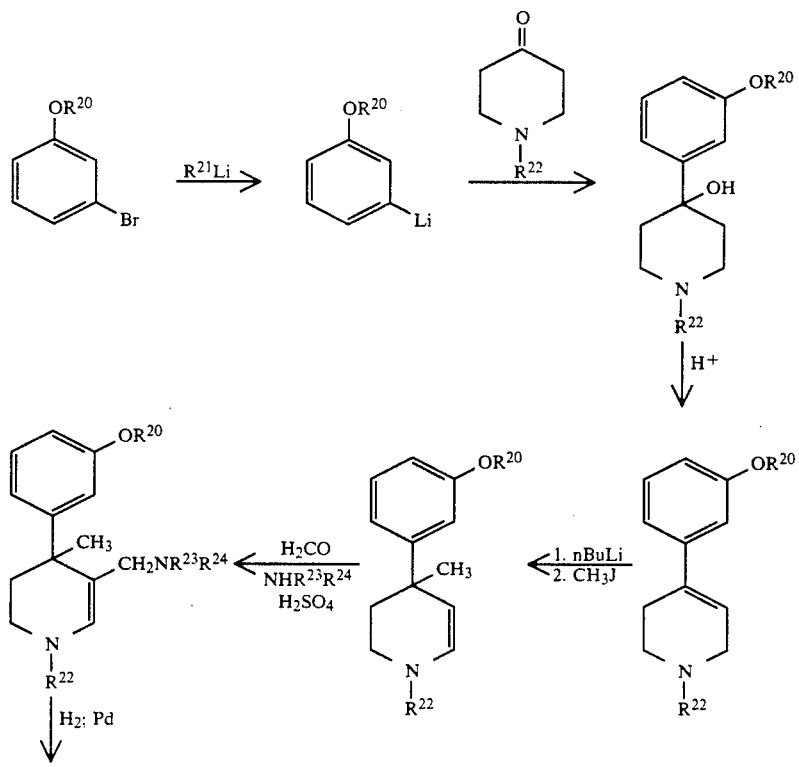

Scheme 1

Scheme 1

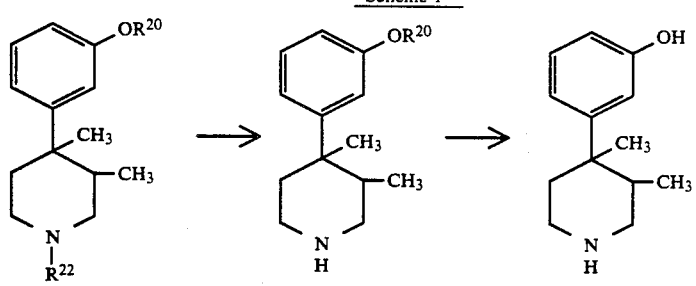

The first step of the above-described process involves the formation of the 3-alkoxyphenyllithium reagent by reacting 3-alkoxybromobenzene with an alkyl-lithium reagent. This reaction is typically performed under inert conditions and in the presence of a suitable non-reactive solvent such as dry diethyl ether or preferably dry tetrahydrofuran. Preferred alkyllithium reagents used in this process are n-butyllithium, and especially sec.-butyllithium. Generally, approximately an equimolar to slight excess of alkyllithium reagent is added to the reaction mixture. The reaction is conducted at a temperature between about −20° C. and about −100° C., more preferably from about −50° C. to about −55° C.

Once the 3-alkoxyphenyllithium reagent has formed, approximately an equimolar quantity of a 1-alkyl-4-piperidone is added to the mixture while maintaining the temperature between −20° C. and −100° C. The reaction is typically complete after about 1 to 24 hours. At this point, the reaction mixture is allowed to gradually warm to room temperature. The product is isolated by the addition to the reaction mixture of a saturated sodium chloride solution in order to quench any residual lithium reagent. The organic layer is separated and further purified if desired to provide the appropriate 1-alkyl-4-(3-alkoxyphenyl)piperidinol derivative.

The dehydration of the 4-phenylpiperidinol prepared above is accomplished with a strong acid according to well known procedures. While dehydration occurs in various amounts with any one of several strong acids such as hydrochloric acid, hydrobromic acid, and the like, dehydration is preferably conducted with phosphoric acid, or especially p-toluenesulfonic acid in toluene or benzene This reaction is typically conducted under reflux conditions, more generally from about 50° C. to about 150° C. The product thus formed is generally isolated by basifying an acidic aqueous solution of the salt form of the product and extracting the aqueous solution with a suitable water immiscible solvents. The resulting residue following evaporation can then be further purified if desired.

The 1-alkyl-4-methyl-4-(3-alkoxyphenyl)tetrahydropyridine derivatives are prepared by a metalloenamine alkylation. This reaction is preferably conducted with n-butyllithium in tetrahydrofuran (THF) under an inert atmosphere, such as nitrogen or argon. Generally, a slight excess of n-butyllithium is added to a stirring solution of the 1-alkyl-4-(3-alkoxyphenyl)-tetrahydropyridine in THF cooled to a temperature in the range of from about −50° C. to about 0° C., more preferably from about −20° C. to about −10° C. This mixture is stirred for approximately 10 to 30 minutes followed by the addition of approximately from 1.0 to 1.5 equivalents of methyl halide to the solution while maintaining the temperature of the reaction mixture below 0° C. After about 5 to 60 minutes, water is added to the reaction mixture and the organic phase is collected. The product can be purified according to standard procedures, but the crude product is preferably purified by either distilling it under vacuum or slurrying it in a mixture of hexane:ethyl acetate (65:35, v:v) and silica gel for about two hours. According to the latter procedure, the product is then isolated by filtration followed by evaporating the filtrate under reduced pressure.

The next step in the process involves the application of the Mannich reaction of aminomethylation to non-conjugated, endocyclic enamines. This reaction is preferably carried out by combining from about 1.2 to 2.0 equivalents of aqueous formaldehyde and about 1.3 to 2.0 equivalents of a secondary amine $NHR^{23}R^{24}$ in a suitable solvent. While water is the preferred solvent, other non-nucleophilic solvents such as acetone and acetonitrile can also be employed in this reaction. The pH of this solution is adjusted to approximately 3.0–4.0 with an acid which provides a non-nucleophilic anion. Examples of such acids include sulfuric acid, the sulfonic acids such as methanesulfonic acid and p-toluenesulfonic acid, phosphoric acid, and tetrafluoroboric acid. The preferred acid is sulfuric acid. To this solution is added one equivalent of a 1-alkyl-4-methyl-4-(3-alkoxyphenyl)tetrahydropyridine, typically dissolved in aqueous sulfuric acid, and the pH of the solution is readjusted with the non-nucleophilic acid or a secondary amine as defined above. The pH should be maintained in the range of from about 1 0 to 5.0 with a pH of about 3 0 to 3.5 being preferred during the reaction. The reaction is substantially complete after about 1 to 4 hours, more typically about 2 hours, when conducted at a temperature in the range of from about 50° C. to about 80° C., more preferably at about 70° C. The reaction is next cooled to approximately 30° C. and added to a sodium hydroxide solution. This solution is extracted with a water immiscible organic solvent, such as hexane or ethyl acetate, and the organic phase, following thorough washing with water to remove any residual formaldehyde, is evaporated to dryness under reduced pressure.

The next step of the process involves the catalytic hydrogenation of the 1-alkyl-4-methyl-4-(3-alkoxyphenyl)-3-tetrahydropyridinemethanamine prepared above to the corresponding trans-1-alkyl-3,4-dimethyl-4-(3-alkoxyphenyl)piperidine. This reaction actually occurs in two steps. The first step is the hydrogenolysis reaction wherein the exo C-N bond is reductively cleaved to generate the 3-methyltetrahydropyridine. In the second step, the 2,3-double bond in the tetrahydropyridine ring is reduced to afford the desired piperidine ring.

Reduction of the enamine double bond introduced the crucial relative stereochemistry at the 3 and 4 carbon atoms of the piperidine ring. The reduction does not occur with complete stereoselectivity. The catalysts employed in the process are chosen from among the various palladium and preferably platinum catalysts.

The catalytic hydrogenation step of the process is preferably conducted in an acidic reaction medium. Suitable solvents for use in the process include the alcohols, such as methanol or ethanol, as well as ethyl acetate, tetrahydrofuran, toluene, hexane, and the like.

Proper stereochemical outcome has been found to be dependent on the quantity of catalyst employed. The quantity of catalyst required to produce the desired stereochemical result is dependent upon the purity of the starting materials in regard to the presence or absence of various catalyst poisons.

The hydrogen pressure in the reaction vessel is not critical but can be in the range of from about 5 to 200 psi. Concentration of the starting material by volume is preferably around 20 ml. of liquid per gram of starting material, although an increased or decreased concentration of the starting material can also be employed. Under the conditions specified herein, the length of time for the catalytic hydrogenation is not critical because of the inability for over-reduction of the molecule. While the reaction can continue for up to 24 hours or longer, it is not necessary to continue the reduction conditions after the uptake of the theoretical two moles of hydrogen. The product is isolated by filtering the reaction mixture for example through infusorial earth, and evaporating the filtrate to dryness under reduced pressure. Further purification of the product thus isolated is not necessary and preferably the diastereomeric mixture is carried directly on to the following reaction.

The alkyl substituent is next removed from the 1-position of the piperidine ring by standard dealkylation procedures. Preferably, a chloroformate derivative, especially the vinyl or phenyl derivatives, are employed and removed with acid. Next, the alkoxy compound prepared above is dealkylated to the corresponding phenol. This reaction is generally carried out by reacting the compound in a 48% aqueous hydrobromic acid solution. This reaction is substantially complete after about 30 minutes to 24 hours when conducted at a temperature between 50° C. to about 150° C., more preferably at the reflux temperature of the reaction mixture. The mixture is then worked up by cooling the solution, followed by neutralization with base to an approximate pH of 8. This aqueous solution is extracted with a water immiscible organic solvent. The residue following evaporation of the organic phase is then preferably used directly in the following step.

The compounds employed as starting materials to the compounds of the invention can also be prepared by brominating the 1-alkyl-4-methyl-4-(3-alkoxyphenyl)-3-tetrahydropyridinemethanamine prepared above at the 3-position, lithiating the bromo compound thus prepared, and reacting the lithiated intermediate with a methylhalide such as methyl bromide to provide the corresponding 1-alkyl-3,4-dimethyl-4-(3-alkoxyphenyl)tetrahydropyridinemethanamine. This compound is then reduced and converted to the starting material as indicated above.

As noted above, the compounds of the present invention can exist as the individual stereoisomers. Preferably reaction conditions are adjusted as disclosed by Barnett (supra) or as set forth in Example 1 hereof to be substantially stereoselective and provide a racemic mixture of essentially two enantiomers. These enantiomers can then be resolved. The preferred procedure employed to prepare the resolved starting materials used in the synthesis of these compounds includes treating a racemic mixture of alkyl-3,4-dimethyl-4-(3-alkoxyphenyl)piperidine with either (+)- or (−)-di-benzoyl tartaric acid to provide the resolved intermediate. This compound is dealkylated at the 1-position with vinyl chloroformate and finally converted to the desired 4-(3-hydroxyphenyl)piperidine isomer. This reaction scheme is represented in the following Scheme 2:

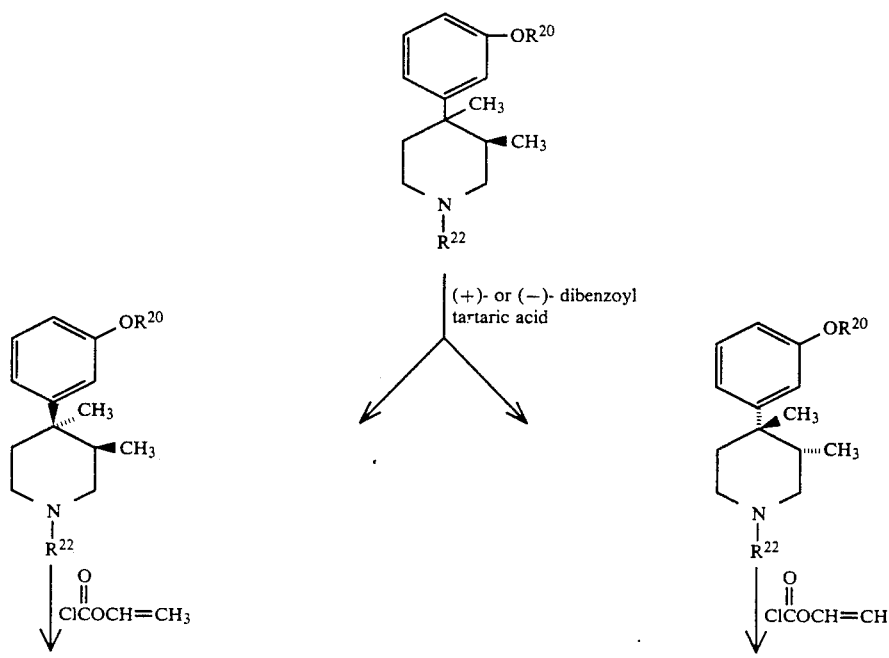

-continued
Scheme 2

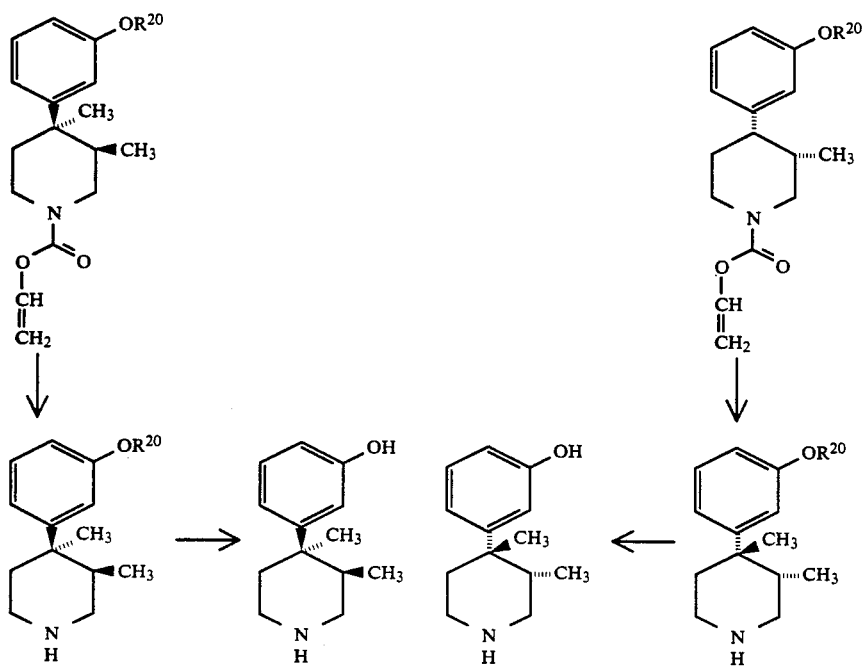

wherein R[20] and R[22] are as defined above.

As will be understood by those skilled in the art, the individual enantiomers of the invention can also be isolated with either (+) or (−) dibenzoyl tartaric acid, as desired, from the corresponding racemic mixture of the compounds of the invention. Preferably the (+)-trans enantiomer is obtained.

Although the (+)trans-3,4 stereoisomer is preferred, all of the possible stereoiosmers of the instant compounds are within the contemplated scope of the present invention. Racemic mixtures of the stereoisomers as well as the substantially pure stereoisomers are within the scope of the invention. The term "substantially pure" is used herein to refer to at least about 90 mole percent, more preferably at least about 95 mole percent and most preferably at least about 98 mole percent of the desired stereoisomer is present compound to other possible stereoisomers.

Intermediates and compounds with the instant invention can be prepared by reacting a 3,4-alkyl-substituted-4-(3-hydroxyphenyl)piperidine with a compound of the formula $LCH_2(CH_2)_{n-1}CHR^3C(O)E$ where L is a leaving group such as chlorine, bromine or iodine, E is a carboxylic acid, ester or amide, and R[8] and n are as defined hereinabove. Preferably L is chlorine and the reaction is carried out in the presence of a base to alkylate the piperidine nitrogen. For example 4-chloro-2-cyclohexylbutanoic acid, ethyl ester can be contacted with (3R,4R)-4-(3-hydroxyphenyl)-3,4-dimethylpiperidine to provide 4-[(3R,4R)-4-(3-hydroxyphenyl)-3,4-dimethyl-1-piperidine]butanoic acid, ethyl ester. Although the ester of the carboxylic acid is preferred, the free acid itself or an amide of the carboxylic acid can be used.

In alternative synthesis, the substituted piperidine can be contacted with an e-methylene alkyl ester to alkylate the piperidine nitrogen. For example, 2-methylene-3-phenylproponic acid, ethyl ester can be contacted with a desired piperidine to provide 2-benzyl-3-piperidinepropanoic acid ethyl ester.

Another synthetic route can involve the reaction of a substituted piperidine with a haloalkylnitrile. The nitrile group of the resulting piperidine alkylnitrile can be hydrolyzed to the corresponding carboxylic acid.

With each of the synthetic routes, the resulting ester or carboxylic acid can be reacted with an amine or alcohol to provide modified chemical structures. In the preparation of amides, the piperidine-carboxylic acid or -carboxylic acid ester is reacted with an amine in the presence of a coupling agent such as dicyclohexylcarbodiimide, boric acid, borane-trimethylamine, and the like. Esters can be prepared by contacting the piperidine-carboxylic acid with the appropriate alcohol in the presence of a coupling agent such as p-toluenesulfonic acid, boron trifluoride etherate or N,N'-carbonyldiimidazole. Alternatively, the piperidine-carboxylic acid chloride can be prepared using a reagent such as thionyl chloride, phosphorus trichloride, phosphorus pentachloride and the like. This acyl chloride can be reacted with the appropiate amine or alcohol to provide the corresponding amide or ester. Examples of such reactions are provided in the appended examples.

The following examples are provided for purposes of illustration and are not to be construed as limiting the scope of the claimed invention.

As used in the instant examples, the following terms have the meanings indicated. "Hobt" refers to 1-hydroxybenzotriazole hydrate "THF" refers to tetrahydrofuran. "DMF" refers to dimethylformamide. "TEA" refers to triethylamine. "DCC" refers to dicyclohexylcarbodiimide.

The column chromatography procedure used involved gravitational flow with Allied Fischer silica gel (70–150 mesh). Gradient solvent procedures were employed using the solvent systems specified in the particular example. The gradient procedure involved starting the indicated solvent system and incrementally changing the solvent mixture until the indicated final solvent system was obtained. Fractions containing product were evaporated generally under reduced vacuum to provide product.

Preparative liquid chromatography was performed with the Waters Prep LC/500 apparatus using dual silica prep pack cartridges. Gradient solvent systems were employed as listed in the particular example.

Optical rotations were determined using methanol as the solvent.

For those examples indicated, purification of the specified compound was accomplished by preparative, centrifugal, thin layer chromatography on a Harrison Model 7924A Chromatron using Analtech silica gel GF rotors. The plate thickness and solvent system employed are indicated in the particular example.

The hydrochloride salt of the particular compound was prepared by placing the free base into ethyl ether. While stirring this ether solution, a solution of HCl in ethyl ether was added dropwise until the base-containing solution became acidic. A preciptate formed which was filtered and dried to provide the corresponding hydrochloride salt of the free base.

In the instant Examples Q-, X-, Z-, M-, G-, and U- are used to represent the moieties indicated hereinabove.

EXAMPLE 1

Preparation of
(+)-(3R,4R)-4-(3-hydroxyphenyl)-3,4-dimethylpiperidine [Q-H]

3-Bromophenol was combined with an equal molar amount of 2-bromopropane in ethanol and in the presence of potassium carbonate to provide 3-bromoisopropoxybenzene.

The 3-bromo-i-propoxybenzene (200 g, 0.08703 mol) was combined with THF (540 ml) under nitrogen and cooled to about $-75°$ C. n-Butyl lithium (565 ml, 0.8306 mol) was added dropwise while maintaining the mixture at less than $-70°$ C. After 2 hours 1,3-Dimethyl-4-piperidone (106.7 g, 0.8389 mol) was added while maintaining the temperature of the mixture between $-80°$ C. and $-70°$ C. After stirring 2 hours at $-70°$ C., the reaction mixture was then added to 6N HCl (280 ml) while maintaining the temperature at 20°-25° C. The pH was adjusted to 1 with 12 N HCl. The aqueous layer containing product was separated and heptane (320 ml) was added along with 50% NaOH (48 ml, pH=13-14) and the resulting mixture allowed to stand overnight. The mixture was heated to 45°-50° C. and the upper layer was separated. The remaining aqueous layer was extracted with heptane (320 ml) at 45°-50° C. The combined organic fractions were washed with de-ionized water (120 ml) at 45°-50° C. The resulting organic layer was vacuum distilled at a pot temperature of about 55° C. at 100 mmHg. Crystallization from heptane and drying provided 151.8 g of 3-(3-i-propoxyphenyl)-1,3-dimethyl-4-hydroxypiperidine. Melting point 75.0°-76.0° C.

This 4-hydroxypiperidine (463 g, 1.758 mol) was combined with ethyl acetate (2275 ml) under nitrogen. The solution was cooled to 0°-5° C. and ethyl chloroformate (205 ml, 2.144 mol) was added while maintaining the temperature below 15° C. The reaction mixture was stirred for an additional 3 hours at room temperature. The mixture was then added to 5N NaOH (750 ml) with stirring (pH=12-13) the organic layer was separated and washed with de-ionized water. Solvent was removed by evaporation at 50° C. to provide 591 g of a viscous oil.

This viscous oil (284.8 g) was dissolved in ethanol (2.6 L) and warmed to 55° C. under nitrogen. (+)-Di-p-toluoyl-D-tartaric acid, monohydrate was added and the solution heated to reflux. After stirring overnight at room temperature, the mixture was cooled to 0°-5° C. before filtering. The filter cake was washed with cold ethanol, air dried for 30 minutes then vacuum dried at 45°-50° C. Recrystallization from ethanol provided 201.7 g of product with a melting point of 153.5°-155° C. (dec). This material had a ratio of isomers by proton NMR of 97:3.

Product prepared in this manner (411.7 g) was added to heptane (1200 ml) and 2N NaOH (550 ml) over a 15 minute period. pH of the mixture was adjusted to about 13 with 50% NaOH and stirred until all solid had dissolved. The layers were separated and the organic layer washed with 1N NaOH (275 ml), de-ionized water (275 ml) and the saturaed aqueous sodium chloride (210 ml). The organic fraction was dried over 175 g of sodium sulfate, filtered and washed with heptane (125 ml). The solvent was removed by evaporation to provide 189.4 g of a colorless viscous oil. $[\alpha]_{589}$ of $-6.92°$ (c=1.01, methanol).

This viscous oil product (50.0 9) and decalin (250 ml) were heated at 190°-195° C. for 19 hr under nitrogen while removing the ethanol formed by distillation. The solution was cooled to 15°-20° C. under nitrogen and 1N HCl (155 ml) was added with stirring. The aqueous fraction was separated and extracted with heptane (2×30 ml). The pH of the aqueous layer was adjusted to about 13 by adding 50% NaOH and extracted with heptane 36.5 g of a yellow-orange liquid were removed from the organic layer. $[\alpha]_{589} = -67.24°$.

This yellow-orange liquid product (19.6 g) was combined with THF (175 ml) and cooled to $-15°$ C. to $-20°$ C. under nitrogen. n-Butyl lithium (70.0 ml) was added with stirring over about 0.5 hr while maintaining the internal temperature at about $-10°$ C. to about $-20°$ C. The mixture was stirred for another 0.5 hr at $-10°$ C. to $-15°$ C. and then cooled to $-45°$ to $-50°$ C. Dimethyl sulfate (7.7 ml) was added slowly over 20-30 minutes while maintaing the temperature between $-45°$ C. and $-50°$ C. The mixture was then stirred for an additional 30 minutes at about $-50°$ C. This reaction mixture was then added slowly to a dilute solution of aqueous ammonium hydroxide (15.5 ml aqueous ammonium hydroxide solution plus 55 ml de-ionized water) at 0°-5° C. The mixture was warmed to 20°-25° C. over 30-45 minutes and stirred an additional 2 hrs at 20-25° C. The organic layer was recovered and washed with de-ionized water followed by removal of solvent by evaporation to provide 21.44 g of 4-(3-i-propoxyphenyl)-1,4,5-trimethyl-2,3-dehydropiperidine as an orange liquid.

This dehydropiperidine (21.2 g) and methanol (195 ml) were combined under nitrogen and cooled to 0°-5° C. Sodium borohydride (4.2 g) was added slowly while maintaining the temperature below 15° C. The reaction mixture was stirred at room temperature for 3 hrs. Acetone (21 ml) was added to the reaction mixture and stirred for 5 minutes. A saturated solution of sodium bicarbonate (25 ml) was added and the mixture stirred for 5 minutes. The alcohols were removed by evaporation at 50° C. De-ionized water (95 ml) and ethyl acetate (95 ml) were added and the resulting mixture stirred to form a solution. Phases were separated and the aqueous phase extracted with ethyl acetate (20 ml). Combined organic fractions were washed with de-ionized water (95 ml) and the solvent removed by evaporation at 50° C. to provide (+)-4-(3-i-propoxyphenyl)-1,3,4-trimethylpiperidine as a yellow liquid (20.5 g).

Anhydrous ethanol (75 ml) and (+)-di-p-toluoyl-D-tartaric acid, monohydrate (12.48 g) were combined and heated to 55°-60° C. under nitrogen. An ethanol solution of the trimethyl piperidine (8.07 g in 20 ml) was added while heating to reflux (about 75° C.). De-ionized water (6 ml) was added to obtain a clear homogeneous solution which was stirred at reflux for 0.5 hr. Cooling, filtering, washing with cold ethanol, and drying provided 15.07 g of (+)-4-(3-i-propoxyphenyl)-1,3,4-trimethylpiperidine·(+)-di-p-toluoyl-D-tartaric acid salt with a melting point 145°-147.5° C. (dec).

Toluene (1400 ml) and 2N NaOH (700 ml) were combined and cooled to 15°-20° C. The piperidine-tartaric salt (395.0 grams) was added with stirring at 15°-25° C. and stirring continued until all solids had dissolved. The layers were separated and the organic fraction washed with 1N NaOH (385 ml) and di-ionized water (385 ml). The organic fraction was filtered and the solvent removed by evaporation (50° C.) to provide 164.8 g of the free base as an oil. $[\alpha]_{589} = +74.18°$.

To a mixture of the free base (+)-4-(3-i-propoxyphenyl)-1,3,%-trimethyl-piperidine (25 g) in toluene (160 ml) at 80-90° C. was added phenylchloroformate (17.2 g). The mixture was heated at reflux (110° C.) for 2 hrs and then cooled to 45°-50° C. NaOH (5 ml, 50%, in 40 ml water) was added and the mixture stirred with cooling to room temperature. After 30 minutes the layers were separated and the organic layer washed with a 1:1 mixture of methanol and 1N HCl, a 1:1 mixture of methanol and 1N NaOH, and then washed with water. Evaportion of the solvent provided 33.9 g of the phenyl carbamate as an oil.

The phenyl carbamate (13.95 g), 48% HBr (17.4 ml) and glacial acetic acid (4.7 ml) were combined and refluxed for 18 hours. The solution was cooled to room temperature; water (50 ml) was added; and the solution was extracted 3 times with t-butyl methyl ether (30 ml aliquots). The pH of the aqueous phase was adjusted to 8.5-8.8 with 50% NaOH solution. Methanol (15 ml) was added and the pH adjusted to 10.5 with the 50% NaOH solution. The mixture was stirred for 1.5 hours, cooled to 5° C. and filtered to provide the white solid (+)-trans-3,4-dimethyl-4-(3-hydroxyphenyl)-piperidine (6.86 g). $[\alpha]_{589} = +380.37$ (methanol).

EXAMPLE 2

Preparation of 3-phenyl-2-(ethoxycarbonyl)-1-propene

N-butyl lithium (201 ml of 1.6M) was added dropwise to diisopropyl amine (45 ml) in dry tetrahydrofuran (870 ml) at −78° C. After stirring at this temperature for 0.5 hours ethyl-2-benzylacetoacetate (39.6 g, 0.18M) in THF (250 ml) was added dropwise at 0° C. After stirring for 20 minutes, paraformaldehyde (35.42 g) was added at room temperature followed by stirring for one hour and refluxing for 4 hours. The reaction mixture was filtered and the liquid evaporated to dryness. The residue was dissolved in a mixture of KHCO₃/H₂O and methylene chloride (1:1) and stirred for 0.5 hours. The layers were separated and the methylene chloride layer was dried over K₂CO₃ and then evaporated to dryness to yield 46.4 g of named product. This product was purified with a Prep-500 chromatograph eluting with hexane to 5% ethyl acetate/hexane gradient to yield 30 g of a clear liquid. ms (fd)=190M+

EXAMPLE 3

Preparation of 3-cyclohexyl-2-(ethoxycarbonyl)-1-propene

A. Ethyl-2-benzylacetoacetate (50 g, 0.227M) was dissolved in ethanol (435 ml) and combined with 5% Rh/Al₂O₃ (15 g) and stirred at room temperature overnight under hydrogen pressure (60 psi). The mixture was filtered and solvent removed under vacuum. The residue was diluted with ethyl acetate and washed with water. The organic layer was dried over K₂CO₃ and the solvent removed under vacuum to provide 49 g of ethyl-2-aceto-3-cyclohexylpropanoate.

B. Ethyl-2-acetohexylpropanoate (20 g) was contacted with N-butyllithium (101 mL 1.6M), diisopropylamine (23 mL in dry THF, 440 mL) and paraformaldehyde (18 g) as in Example 2 to provide 19 g of crude product which was purified by bulb-to-bulb distillation at 130° C., 0.1 mmHg to provide 10 g of the named product as a clear liquid.

ms (fd)=196M+

EXAMPLE 4

A. Preparation of trans-4-(3-hydroxyphenyl)-3,4-dimethyl-a-(phenylmethyl)-1-piperidinepropanoic acid, ethyl ester hydrochloride [Z-OCH₂CH₃·HCl]

Trans-(+)-3,4-dimethyl-4-(3-hydroxyphenyl)-piperidine (6.0 g, 29 mmole) and 3-phenyl-2-(ethoxycarbonyl)-1-propene (6.1 g) were dissolved in methanol (300 ml) and stirred at room temperature under nitrogen. During the 10 day reaction time, the mixture was evaporated two times and rediluted with methanol on days 5 and 9. On day 10 the mixture was evaporated to dryness to provide 13 g of solid which was passed through a silica column eluting with hexane to ethyl acetate gradient providing 11.4 g of purified product. Analysis for C₂₅H₃₃NO₃·HCl: Theory: C, 69.50; H, 7.93; N, 3.24; Found: C, 69.36; H, 7.69; N, 3.21.

B. Preparation of 4-(3-hydroxyphenyl)-3,4-dimethyl-a-(phenylmethyl)-1-piperidinepropanoic acid monohydrate [Z-OH·H₂O]

To 1.0 g of the product from 4A was added dioxane (60 ml) and 6 N HCl (30 ml). The mixture was heated to reflux for two hours, cooled and the solvent removed under vacuum. The residue was rediluted with water and the pH adjusted to 9.8 with ammonium hydroxide. The desired acid was extracted with 3:1 butanol/toluene solution. The solvent was removed and the residue was passed through a silica column eluting with a mixture of methanol and ethyl acetate (20:80, v:v). The resulting material was slurried in ethyl ether, and filtered to give 650 mg of product having m.p. 120°-131° C.

Analysis for C₂₃H₃₁NO₄: Theory: C, 71.66, H, 8.11; N, 3.63; Found : C, 71.89; H, 8.09; N, 3.71.

EXAMPLE 5

A. Preparation of 3-(3,4-dimethyl-4-(3-hydroxyphenyl)-1-piperidinyl]-2-(cyclohexylmethyl)propanoic acid ethyl ester hydrochloride

[M-OCH₂CH₃·HCl]

The procedure of Example 4A was used with trans-(±)-3,4-dimethyl-4-(3-hydroxyphenyl)piperidine (4.0 g)

and 2-(ethoxycarbonyl)-3-phenyl-1-propene (4.61 g). The solvent was removed under vacuum and the residue diluted with ethyl acetate and water. The pH was adjusted to 9.8 with 1N NaOH and the mixture was extracted with ethyl acetate. This organic layer was dried over $K_2CO_3$. The solvent removed to yield 4.3 g. The HCl-salt was prepared having a melting point 101°-111° C.

Analysis for $C_{25}H_{39}NO_3 \cdot HCl$: Theory: C, 68.55; H, 9.20; N, 3.19; Found: C, 68.32; H, 9.16; N, 3.18.

B. Preparation of 3-[3,4-dimethyl-4-(3-hydroxyphenyl)-1-piperidinyl]-2-(cyclohexylmethyl)-propanoic acid monohydrate [M-OH·$H_2O$]

2.88 g of compound from preparation 5A was added to dioxane (75 ml) and 6N HCl (75 ml) and allowed to reflux with stirring for five hours. The solvent was removed under reduced pressure and the residue was taken into $H_2O$. The pH of the water was adjusted to 9.8 with ammonium hydroxide. The solution was extracted with a mixture of butanol and toluene (3:1, v:v) and dried over magnesium sulfate. The solvent was removed by vacuum to yield 2.6 g of solid. This material was purified by column chromatography eluting with a 1:1 ethyl acetate-methanol mixture. After removal of solvent, the material was triterated with ethyl ether and filtered to give 640 mg of product. m.p.=145°-150° C.

Analysis for $C_{23}H_{35}NO_3 \cdot H_2O$: Theory: C, 70.55; H, 9.52; N, 3.57; Found: C, 70.78; H, 9.34; N, 3.54.

EXAMPLE 6

Preparation of ethyl-2-phenyl-4-chlorobutanoate

Diisopropylamine (2.71 ml, 1.1 eq) was added to dry THF (10 ml) and cooled to −78° C. N-butyllithium (11.01 ml of 1.6 Molar, 1.1 eq) was added dropwise. The mixture was stirred at -78° C. for 30 minutes and ethyl-2-phenylacetate (2.9 g, 1.0 eq) was dissolved in dry THF (20 ml) and the solution added dropwise to the reaction mixture. The mixture was stirred at −78° C. for 0.25 hour and then allowed to warm to −30° C. and stirred for an additional 0.25 hour. 1,3-Dimethyl-3,4,5,6-tetrahydro-2(1H)-pyrimidinone (DMPU) (2.13 ml, 1.0 eq) was dissolved in dry THF (20 ml) and added dropwise to the mixture. The resulting mixture was maintained at −30° C. for ten minutes. This mixture was then cannulated under $N_2$ pressure to a flask which had been charged with ethyl ether (100 ml) and 1-bromo-2-chloroethane (7.3 ml, 5.0 eq) at −10° C. The mixture was stirred for three hours at −10° C. to −5° C. The mixture was cooled to −30° C. and quenched with a saturated ammonium chloride solution. The mixture was extracted with ethyl ether which was then dried over $K_2CO_3$. The solvent was stripped to provide 3.2 g of product which distilled at 70°-71° C. under 0.01 mmHg.

ms (fd)=226M+

EXAMPLE 7

Preparation of ethyl-2-cyclohexyl-4-chlorobutanoate

Diisopropylamine (2.71 ml, 1.1 eq.) was added to dry THF (10 ml) and cooled to -78° C. N-Butyllithium (11.01 ml of 1.6 Molar solution, 1.0 eq.) was added and the mixture stirred at -78° C. for 0.5 hour. To this mixture was then added dropwise a solution of ethyl-2-cyclohexylacetate (3.0 g, 1.0 eq.) in THF (20 ml) at −78° C. and stirred for 0.5 hour. DMPU (2.13 ml, 1.0 eq.) in THF (20 ml) was added dropwise and allowed to stir at −78° C. for 10 minutes. To this mixture was added 1-bromo-2-chloroethane (1.46 ml, 1.0 eq.) in THF (10 ml) and the mixture stirred at −5° C. for 15 minutes. The mixture was then warmed to room temperature and stirred for 1.0 hour. The mixture was cooled to 0° C., quenched with saturated ammonium chloride solution, extracted with ethyl ether and the ether layer was washed three times with water. The organic layer was separated, dried over $K_2CO_3$ and the solvent removed to provide 3.6 g of product. This was fractionally distilled to provide 3.0 g of product Boiling Point 66°-70° C. at 0.05 mmHg.

Analysis for $C_{12}H_{21}O_2Cl$; Theory: C, 61.93; H, 9.09; Found: C, 61.66; H, 9.23.

EXAMPLE 8

A. Preparation of trans-4-[(3-Hydroxyphenyl)-3,4-dimethyl-1-piperidine]-2-phenyl butanoic acid, ethyl ester hydrochloride [U-OCH$_2$CH$_3$·HCl]

Ethyl-4-chloro-2-phenylbutanoate (2.43 g), trans-(+)-3,4-dimethyl-4-(3-hydroxyphenyl)piperidine [Q-OH] (2.0 g), NaHCO$_3$ (905 mg), NaI (1.53 g), and dimethylformamide (DMF) (120 ml) were combined and heated to reflux for two hours. The mixture was cooled and evaporated to dryness. The solid was taken into $H_2O$ and the pH adjusted to 9.8 with 1N NaOH. This mixture was extracted with ethyl acetate and the organic layer dried over $K_2CO_3$. The solvent was removed under vaccum to provide 5 g of crude product. This product was subjected to column chromatography eluting with ethyl acetate to provide 4.0 g of material. This material was converted to the HCl salt.

Analysis: $C_{25}H_{33}N_3O \cdot HCl$ Theory: C, 69.51; H, 7.93; N, 3.24; Found: C, 69.72; H, 7.77; N, 3.34.

EXAMPLE 8B

B. Preparation of trans-4-[(3-Hydroxyphenyl)-3,4-dimethyl-1-piperidine]-2-phenyl butanoic acid hydrochloride [U-OH·HCl]

The ethyl ester product of Example 8A (3.0 g) was combined with 6N HCl (250 ml) and dioxane (30 ml). The mixture was stirred at reflux for 18 hours. The solvent was removed under vacuum. The residue was taken into $H_2O$, the pH was adjusted to 9.8 with TEA and the desired product extracted with a 3:1 butanol-toluene solution. The organic layer was dried over MgSO$_4$ and the solvent removed under vacuum to yield 2.6 g white solid. The compound was converted to the HCl salt. m.p.=140°-150° C.

Analysis: $C_{23}H_{29}N_3O \cdot HCl$ Theory: C, 68.39; H, 7.49; N, 3.47; Found: C, 68.19; H, 7.27; N, 3.47.

EXAMPLE 9

A. Preparation of trans-4-[(3-hydroxyphenyl)-3,4-dimethyl-1-piperidine]-2-cyclohexylbutanoic acid, ethyl ester hydrochloride [G-OCH$_2$CH$_3$·HCl]

DMF (80 ml) was added to trans-(+)-3,4-dimethyl-4-(3-hydroxyphenyl)piperidine (1.0 g) followed by NaI (735 mgs, 1.0 eq), $K_2CO_3$ (677 mgs, 1.0 eq) and then ethyl 4-chloro-2-cyclohexylbutanoate (1.0 eq). The mixture was refluxed for 2 hours, cooled and poured into water. The pH was adjusted to 9.8 with 1 NaOH. The mixture was extracted with ethyl ether and the organic layer dried over $K_2CO_3$. The solvent was removed under vacuum to provide 1.6 g of solid. The hydrochloride salt was prepared to yield 1.1 g of a white solid.

m.p. 80°-95° C.

Analysis: $C_{25}H_{39}NO_3 \cdot HCl$ Theory C, 68.55; H, 9.20; N, 3.20; Found: C, 68.27; H, 9.18; N, 3.37.

EXAMPLE 9B

Preparation of trans-4-[(3-hydroxyphenyl)-3,4-dimethyl-1-piperidinyl]-2-cyclohexylbutanoic acid hydrochloride [G-OH·HCl]

Product (HCl salt) from Example 9A (1.0 g) was combined with 6N HCl (100 ml) and the mixture refluxed for 18 hours. The hot mixture was filtered and the filtrate evaporated under vacuum to provide a white solid. The solid was triturated with ethyl acetate and filtered. The white solid was dried in a vacuum oven to provide 600 mg as the HCl salt. This salt was taken into water and the pH adjusted to 9.8 with TEA. The product was extracted with a 3:1 butanol:toluene mixture and dried over $MgSO_4$. The solvent was removed to provide 460 mg of product as a white solid. The HCl salt was made.

m.p. = 140°-160° C. (foam)

Analysis: $C_{23}H_{35}NO_3 \cdot HCl$: Theory: C, 67.38; H, 8.85; N, 3.42; Found: C, 67.44; H, 8.94; N, 3.58.

EXAMPLE 10

Preparation of trans-4-[(3-hydroxyphenyl)-3,4-dimethyl-1-piperidinyl]-2-phenyl-N,N-dimethylbutanamide hydrochloride [U-N(CH₃)₂·HCl]

Acid prepared as in Example 8B (1.5 g, 3.72 mmoles), dimethylamine hydrochloride (334 mg), DCC (845 mg), 1-hydroxybenzotriazole hydrate (553 mg), diisopropyl ethyl amine (5.85 ml), and DMF (100 ml) were combined and stirred at room temperature for 24 hours. The mixture was poured into water and the pH adjusted to 9.8 with 1N NaOH. The mixture was extracted with ethyl acetate and the organic layer dried over $K_2CO_3$. The solvent was removed under vacuum to yield 1.56 g of desired product. The product was passed through a silica column with methanol to provide 800 mg of material. The HCl salt was prepared and filtered to yield 810 mgs.

ms (fd) = 394 M+

Analysis: $C_{25}H_{34}N_2O_2 \cdot HCl$: Theory: C, 69.67; H, 8.19; N, 6.50; Found: C, 69.37; H, 8.06; N, 6.40.

EXAMPLE 11

Preparation of 2-[[4-4-(3-hydroxyphenyl)-3,4-dimethyl-1-piperidinyl]-1-oxo-2-phenylbutyl]amino]-acetic acid ethyl ester monohydrochloride [U-NHCH₂C(O)-OCH₂CH₃·HCl]

The following materials were combined in dry DMF (75 ml): substituted-butanoic acid prepared as in Example 8B (1.5 g, 4 mmole), glycine ethyl ester (558 mg), triethylamine (404 mg), Hobt (540 mg), DCC (824 mg). The above materials were mixed together at room temperature under nitrogen and stirred for three days with the DCC added after solubilization of the solids. The reaction was then filtered and evaporated to dryness. The residue was solubilized in ethyl acetate, washed one time with water and dried over $K_2CO_3$. The solvent was evaporated to provide 800 mg of solid product. The product was subjected to column chromatography eluting with a gradient of ethyl acetate to a 9:1 (v:v) ethyl acetate-methanol mixture to provide 400 mg of a semisolid material. This was converted to HCl salt to provide 270 mg of white solid.

m.p. = 102°-107° C.

ms (fd) = 452 M+, 453 M+ +1

Analysis: $C_{27}H_{36}N_2O_4 \cdot HCl$ Theory: C, 66.31; H, 7.63; N, 5.73; Found: C, 65.99; H, 7.75; N, 5.92.

EXAMPLE 12

Preparation of 2-[[4-[4-(3-hydroxyphenyl)-3,4-dimethyl-1-piperidinyl]-2-phenyl-1-oxobutyl]amino]ethanoic acid monohydrate. [U-NHCH₂C(O)OH·H₂O]

Ethyl ester prepared as in Example 11 (1.6 g, 3.5 mmole) and lithium hydroxide (440 mg) were combined in 60 ml of a mixture of tetrahydrofuran, methanol, and water (v:v:v, 3:1:1) and stirred at room temperature. After three hours the mixture was poured into 100 ml of a 10 weight percent aqueous solution of HCl. The mixture was then extracted with a butanol/toluene (v:v, 3:1) solution. The organic layer was backwashed one time with water, dried over $K_2CO_3$ and the solvent evaporated under vacuum to yield 1.51 g of solid product. The product was subjected to column chromatography eluting with a gradient of ethyl acetate/methanol (9:1, v:v) to ethyl acetate/methanol (1:1, v:v) under nitrogen pressure providing 360 mg of product as a white solid. m.p. = 145°-150° C. with decomposition ms (fd) = 424 M+

Analysis $C_{25}H_{32}N_2O_4 \cdot H_2O$: Theory: C, 67.85; H, 7.74; N, 6.33; Found: C, 67.55; H, 7.87; N, 6.05.

EXAMPLE 13

Preparation of N-(methyl)-2-[[4-[4-(3-hydroxyphenyl)-3,4-dimethyl-1-piperidinyl]-2-phenyl-1-oxobutyl]amino]acetamide monohydrochloride. [U-NHCH₂C(O)-NHCH₃·HCl]

U-NHCH₂C(O)OCH₂CH₃·HCl (400 mg) prepared as in Example 11, methylamine (10 ml, 40% in water), methanol (5 ml) were mixed together and stirred at room temperature overnight. The solvent was removed to provide 392 mg of an oil which was subjected to column chromatography eluting with a gradient of ethyl acetate to ethyl acetate/methanol (v:v, 9:1). 225 mg of a semisolid was recovered. The HCl salt was prepared and dried to provide 220 mg of white solid. m.p. = 115°-119° C.

Analysis for $C_{26}H_{35}N_3O \cdot HCl$ Theory: C, 65.88; H, 7.66; N, 8.86; Found: C, 65.63; H, 7.47; N, 8.70.

EXAMPLE 14

Preparation of trans-N-(2-amino-2-oxoethyl)-4-[3,4-dimethyl-4-(3-hydroxyphenyl)-1-piperidinyl]-2-phenylbutanamide monohydrochloride monohydrate. [U-NHCH₂C(O)NH₂·HCl·H₂O]

The procedure of 13 was followed with product from Example 11 (400 mg), ammonium hydroxide (10 ml, 28%), and methanol (5 ml) to yield 390 mg of a semisolid. This product was subjected to column chromatography eluting with a gradient of ethyl acetate/methanol (v:v, 9:1) to ethyl acetate/methanol (v:v, 1:1). The solvent was removed to yield 240 mg of solid. ms (fd) = 423 M+ and 424 + +1

The HCl salt was prepared and dried to provide 200 mg of a white solid.

m.p. = 128°-132° C.

Analysis for $C_{25}H_{33}N_3O_3 \cdot HCl \cdot H_2O$: Theory: C, 62.81; H, 7.59; N, 8.79; Found: C, 63.04; H, 7.74; N, 8.54.

EXAMPLE 15

Preparation of
N-ethyl-2-[[4-[4-(3-hydroxyphenyl)-3,4-dimethyl-1-piperidinyl]]-2-phenyl-1-oxobutylamino]-acetamide monohydrochloride monohydrate.
U-NHCH$_3$C(O)-NHCH$_2$CH$_3$·HCl·H$_2$O]

The same procedure as in Example 13 was followed using the product from the procedure of Example 11 (400 mg) and ethylamine (20 ml, 70% in H$_2$O) except the reaction was run for 3.5 days. 400 mg of an oil was recovered. This was subjected to column chromatography eluting with a gradient of ethyl acetate to methanol providing 250 mg of a solid.

ms (fd)=451 M+ and 452 M++1

The HCl salt was prepared and dried to provide 200 mg of solid.

m.p.=95°–105° C. (foam)

Analysis for C$_{27}$H$_{37}$N$_3$O$_3$·HCl H$_2$O: Theory: C, 64.08; H, 7.97; N, 8.30; Found: C, 64.37; H, 7.78; N, 8.19.

EXAMPLE 16

Preparation of
3-[[2-cyclohexyl-4-[4-(3-hydroxypheny)-3,4-dimethyl-1-piperidinyl]-1-oxobutyl]amino]proprionic acid ethyl ester monohydrochloride.
[G-NH(CH$_2$)$_2$C(O)OCH$_2$CH$_3$·HCl]

The butanoic acid (G-OH] prepared as in Example 9B (1.45 g, 3.9 mmole), ethyl-3-aminopropionate (600 mg), triethylamine (394 mg) and Hobt (527 mg) were combined in dry DMF (75 ml) followed by the addition of DCC (308 mg). The mixture was stirred at room temperature for 64 hours under nitrogen, evaporated to dryness, and the residue dissolved in ethyl acetate. The ethyl acetate layer was washed two times with water, dried over K$_2$CO$_3$ and then evaporated to dryness to yield 2.16 g of material. This material was subjected to column chromatography eluting with a gradient of ethyl acetate/hexane (v:v, 1:1) to ethyl acetate. Removal of solvent provided 1.35 g of product with a mass spec of 472 M+ and 473 M++1. The HCl salt was prepared and dried to provide 1.5 g of white solid.

m.p.=117°–122° C.

Analysis: C$_{28}$H$_{44}$N$_2$O$_4$·HCl Theory: C, 66.21 H, 9.03 N, 5.31; Found: C, 66.05; H, 8.91; N, 5.40.

EXAMPLE 17

Preparation of
N-(3-amino-3-oxopropyl)-4[3,4-dimethyl-4-(3-hydroxyphenyl)-1-piperidinyl]-2-butanamide monohydrochloride. [G-NH(CH$_3$)$_2$C(O)NH$_2$·HCl]

The ethyl propionate (HCl salt) G-NH(CH$_2$)$_2$-C(O)OCH$_2$CH$_3$] prepared as in Example 16 (400 mg) and ammonium hydroxide (25 ml, 28% in H$_2$O) were mixed and stirred at room temperature overnight. The mixture was evaporated to dryness and the residue was taken into butanol/toluene (v:v, 3:1) and water. The pH was adjusted to 9.8 with 1N NaOH and the layers were separated. The organic layer was washed one time with water, dried over K$_2$CO$_3$ and then evaporated under vacuum to yield 350 mg of material. This material was subjected to column chromatography eluting with ethyl acetate to methanol gradient. Removal of the solvent provided 200 mg of product with a mass spec of 443 M+ and 444 M++1. The HCl salt was prepared and dried to yield 160 mg of white solid.

m.p.=119°–124° C. (with decomposition)

Analysis for C$_{26}$H$_{41}$N$_3$O$_3$·HCl: Theory: C, 65.05; H, 8.82; N, 8.75; Found: C, 64.76; H, 8.75; N, 8.38.

EXAMPLE 18

Preparation of
N-[3-(methylamino)-3-oxopropyl]-4-[4-(3-hydroxyphenyl)-3,4-dimethyl-1-piperidinyl]-2-cyclohexylbutanamide monohydrochloride.
[G-NH(CH$_2$)$_2$-C(O)NHCH$_3$·HCl].

The procedure of Example 17 was followed with the ethyl propionate product (HCl salt) prepared as in Example 16 (450 mg), methylamine (25 ml, 40% in H$_2$O) and dioxane (10 ml) to provide 470 mg of material. This material was subjected to column chromatography eluting with ethyl acetate/methanol (v:v, 9:1) to methanol gradient. Solvent was removed to provide 290 mg of product.

ms (fd)=458 M+, 459 M++1

The HCl salt was prepared and dried to provide 275 mg of a white solid.

m.p.=124°–130° C.

Analysis for C$_{27}$H$_{43}$N$_3$O$_3$·HCl: Theory: C, 65.63; H, 8.98; N, 8.50; Found: C, 65.42; H, 9.01; N, 8.29.

EXAMPLE 19

Preparation of
trans-N-[2-ethoxy-2-oxoethyl-4-[4-(3-hydroxyphenyl)-3,4-dimethyl-1-piperidinyl]-2-cyclohexylbutanamide hydrochloride. [G-NHCH$_2$C(O)OCH$_2$-CH$_3$·HCl]

The butanoic acid prepared as in Example 9B (900 mg), glycine ethyl ester·HCl (348 mg), Hobt (338 mg), TEA (253 mg), and DCC (515 mg) were combined and the reaction was stirred for 72 hours at room temperature. The mixture was evaporated to dryness under vacuum. The residue was dissolved into water/ethyl acetate and the pH of the water layer was adjusted to 9.8 with 1N sodium hydroxide. The layers were separated and the organic layer washed with water, dried over K$_2$CO$_3$ and the solvent was evaporated under vacuum to yield 1.25 g of oily material. This material was subjected to column chromatography eluting with ethyl acetate. Solvent removal provided 720 mg of product. This material was converted to the HCl salt.
ms (fd)=458 M+ m.p.=98°–101° C.

Analysis: C$_{27}$H$_{42}$N$_2$O$_4$·Hcl Theory: C, 65.50; H, 8.75; N, 5.66; Found: C, 65.84; H, 8.81; N, 5.87.

EXAMPLE 20

Preparation of
N-(2-amino-2-oxoethyl)-4-[4-(3hydroxyphenyl)-3,4-dimethyl-1-piperidinyl]-2-cyclohexylbutanamide hydrochloride monohydrate.
[G-NHCH$_2$C(O)-NH$_2$·HCl·H$_2$O]

The procedure of Example 17 was followed with the butanamide product (HCl salt) prepared as in Example 19 (400 mg), ammonium hydroxide (25 ml, 28% in water) and methanol (10 ml) with the mixture being stirred overnight. 350 mg of material was recovered and subjected to column chromatography eluting with a gradient of ethyl acetate to ethyl acetate/methanol (v:v, 1:1). Removal of solvent yielded 220 mg of product with a mass spec of 429 M+ and 430 M++1. The HCl salt was prepared and dried to yield 170 mg of white solid.

m.p.=129°–134° C.

Analysis for $C_{25}H_{39}N_3O_3 \cdot HCl \cdot H_2O$: Theory: C, 62.03; H, 8.75; N, 8.68; Found: C, 62.46; H, 8.53; N, 8.20.

EXAMPLE 21

Preparation of N-[2-(methylamino)-2-oxoethyl]-4-[4-(3-hydroxyphenyl)-3,4-dimethyl-1-piperidinyl]-2-cyclohexyl butanamide hydrochloride.
[G-NHCH$_2$C(O)NHCH$_3 \cdot$HCl]

The procedure of Example 17 was followed with the butanamide product [G-NHCH$_2$C(O)OCH$_2$CH$_3$] (HCl salt) prepared as in Example 19 (600 mg) and methylamine (35 ml, 40% in H$_2$O) to yield 580 mg of material. This material was subjected to column chromatography eluting with a gradient of ethyl acetate to ethyl acetate/methanol (v:v, 1:1) providing 300 mg of product. The HCl salt was prepared and dried to yield 275 mg of a white solid.

ms (fd)=444 M+
m.p.=119°-12° C.

Analysis for $C_{26}H_{41}N_3O_3 \cdot HCl \cdot H_2O$: Theory: C, 62.68; H, 8.90; N, 8.44; Found: C, 62.39; H, 8.64; N, 8.23.

EXAMPLE 22

Preparation of N-[2-(ethylamino)-2-oxoethyl]-4-[4-(3-hydroxyphenyl)-3,4-dimethyl-1-piperidinyl]-2-cyclohexyl butanamide hydrochloride. [G-NHCH$_2$C(O)NHCH$_2$CH$_3 \cdot$HCl]

The procedure of Example 17 was followed with the butanamide (HCl salt) product prepared as in Example 19 (600 mg) and ethylamine (30 ml, 70%) to yield 660 mg of material. This material was subjected to column chromatography eluting with a gradient of ethyl acetate to ethyl acetate/methanol (v:v, 1:1). Solvent removal provided 320 mg of product. The HCl salt was prepared and dried to yield 350 mg of white solid.

ms (fd)=458 M+
m.p.=123°-126° C.

Analysis for $C_{27}H_{43}N_3O_3 \cdot HCl \cdot H_2O$: Theory: C, 63.31; H, 8.98; N, 8.21; Found: C, 63.53; H, 8.92; N, 8.47.

EXAMPLE 23

Preparation of 4-[2-cyclohexyl-4-[4-(3-hydroxyphenyl)-3,4-dimethyl-1-piperidinyl]-1-oxobutyl]amino]-butanoic acid ethyl ester monohydrochloride monohydrate
[G-NH(CH$_2$)$_3$C(O)OCH$_2$CH$_3 \cdot$HCl$\cdot$H$_2$O]

The butanoic acid product prepared as in Example 9B (1.5 g), ethyl-4-aminobutanoate hydrochloride (671 mg), TEA (405 mg) Hobt (540 mg) were combined in dry DMF (150 ml). DCC (824 mg) was added last. The mixture was stirred 64 hours at room temperature under nitrogen. After evaporation to dryness, the residue was taken into ethyl acetate which was washed two times with water and dried over K$_2$CO$_3$. Evaporation to dryness yielded 2.23 g of residue. This material was subjected to column chromatography eluting with a gradient of ethyl acetate to methanol/ethyl acetate (v:v, 9:1). Removal of solvent provided 1 g of product.

ms (fd)=486 M+ and 487 M++1 350 mg of this product was converted to HCl salt to yield 300 mg of white solid after drying.

m.p.=76°-79° C.

Analysis for $C_{29}H_{46}N_2O_4 \cdot HCl \cdot H_2O$ Theory: C, 64.30; H, 9.05; N, 5.18; Found: C, 63.90; H, 9.01; N, 5.12.

EXAMPLE 24

Preparation of N-methyl-4-[[4-[4-(3-hydroxyphenyl)-3,4-dimethyl-1-piperidinyl]-2-cyclohexyl-1-oxobutyl]amino]butanamide monohydrochloride monohydrate.
G-NH(CH$_2$)$_3$C(O)NHCH$_3 \cdot$HCl$\cdot$H$_2$O]

Butanoate product prepared as in Example 23 (450 mg) and methylamine (15 ml, 40% in water) were mixed and stirred at room temperature for three hours. Evaporation of the reaction mixture to dryness provided a residue which was dissolved into butanol-toluene (v:v, 3:1) and water. The water layer was taken to a pH of 9.8 with 1N NaOH and the layers separated. The organic layer was washed one time with water, dried over K$_2$CO$_3$ and the solvent removed to yield 470 mg of a viscous oil. This material was column chromatographed eluting with a gradient of ethyl acetate to ethyl acetate/methanol (v:v, 1:1) providing 250 mg of product. The HCl salt was prepared and dried to yield 250 mg of white solid.

m.p.=78°-84° C. (foam)

Analysis for $C_{28}H_{45}N_3O_3 \cdot HCl \cdot H_2O$: Theory: C, 63.91; H, 9.20; N, 7.99; Found: C, 64.21; H, 8.95; N, 7.83.

EXAMPLE 25

Preparation of 3-[[2-cyclohexyl-4-[4-(3-hydroxyphenyl)-3,4-dimethyl-1-piperidinyl]-1-oxobutyl]amino]propanoic acid phenylmethyl ester hydrochloride monohydrate.
[G-NH(CH$_2$)$_2$C(O)OCH$_2$(C$_6$H$_5$)$\cdot$HCl$\cdot$H$_2$O]

The butanoic acid of Example 9B (900 mg) [G-OH], β-alanine benzyl ester.para-tosylate (878 mg), Hobt (338 mg), DCC (515 mg) and TEA (253 mg) were combined in DMF (100 ml) and stirred for 64 hours at room temperature. The solution was evaporated to dryness under vacuum. The residue was partitioned between ethyl acetate and water and the water layer was adjusted to a pH of 9.8 with 1N NaOH. The layers were separated and the organic layer washed one time with water, dried over K$_2$CO$_3$ and evaporated to yield 1.57 g of material. This material was column chromatographed eluting with a gradient of ethyl acetate to ethyl acetate-methanol (1:1, v:v) providing 620 mg of product. This was converted to HCl salt.

ms (fd)=534 M+ and 535 M++1
m.p.=87°-90° C.

Analysis for $C_{33}H_{46}N_2O_4 \cdot HCl \cdot H_2O$: Theory: C, 67.23; H, 8.39; N, 4.75; Found: C, 67.31; H, 8.43; N, 5.03.

EXAMPLE 26

Preparation of 3-[4-[3,4-dimethyl-4-(-3-hydroxyphenyl)-1-piperidinyl]-2-cyclohexyl-1-oxobutylamino]-propanoic acid monohydrate [G-NH(CH$_2$)$_2$C(O)OH$\cdot$H$_2$O]

Propanoate prepared in Example 25 (1.5 g) was dissolved in ethanol and 5% Pd on carbon was added and the solution was stirred overnight under 60 Psi hydrogen pressure. The mixture was filtered and evaporated to dryness to yield 1.43 g of material. This material was triterated in ethyl acetate and filtered to yield 1.11 g of product.

ms (fd)=444 M+ to 445 M++1
m.p.=90°-93° C.

Analysis for $C_{26}H_{40}N_2O_4 \cdot H_2O$: Theory: C, 67.53; H, 9.09; N, 6.06; Found: C, 67.77; H, 8.96; N, 5.90.

EXAMPLE 27

Preparation of
2-[[2-cyclohexyl-4-[4-(3-hydroxyphenyl)-3,4-dimethyl-1-piperidinyl]-1-oxobutyl]amino]-acetic acid monohydrate [G-NHCH$_2$C(O)OH·H$_2$O]

Butanamide (HCl salt) [G-NHCH$_2$C(O)OCH$_2$CH$_2$·HCl] prepared as in Example 19 (400 mg), 6N HCl (30 ml), and dioxane (30 ml) were combined and refluxed for four hours. The mixture was evaporated to dryness and the residue was partitioned between butanol-toluene (v:v, 3:1) and water. The pH of the water was adjusted to 9.8 with ammonium hydroxide and the layers were separated. The organic layer was dried over MgSO$_4$ and evaporated to provide 540 mg of material. This material was subjected to column chromatography eluting with ethyl acetate/methanol (v:v, 1:1). Removal of solvent provided 172 mg of product.

ms (fd)=430 M$^+$ and 431 M$^+$+1
m.p.=148°-153° C.

Analysis for C$_{25}$H$_{38}$N$_2$O$_4$·H$_2$O: Theory: C, 66.94; H, 8.90; N, 6.24; Found: C, 66.64; H, 8.84; N, 5.88.

EXAMPLE 28

Preparation of
4-[[2-cyclohexyl-4-[4-(3-hydroxyphenyl)-3,4-dimethyl-1-piperidinyl]-1-oxobutyl]amino]-butanoic acid monohydrate [G-NH(CH$_2$)$_3$C(O)OH·H$_2$O]

The butanoate prepared using the procedure of Example 23 (550 mg), 6N HCl (20 ml) and dioxane (20 ml) were combined and refluxed for two hours. The reaction mixture was evaporated to dryness. The residue was taken into water and butanol-toluene (v:v, 3:1). The pH of the water layer was adjusted to 9.8 using ammonium hydroxide and the layers were separated. The organic layer was washed one time with water, dried over MgSO$_4$ and evaporated to provide 490 mg of dry material. This material was subjected to column chromatography eluting with a gradient of hexane/ethyl acetate (v:v, 1:1) to ethyl acetate. Solvent removal provided 300 mg of product.

ms (fd)=458 M$^+$
m.p.=113°-118° C. (with decomposition)

Analysis for C$_{27}$H$_{42}$N$_2$O$_4$·H$_2$O: Theory C, 67.99; H, 9.23; N, 5.88; Found: C, 67.85; H, 8.88; N, 5.65.

EXAMPLE 29

Preparation of
2-[[3-[4-(3-hydroxyphenyl-3,4-dimethyl-1-piperidinyl]-2-cyclohexylmethyl-1-oxopropyl]amino]acetic acid ethyl ester monohydrochloride. [M-NHCH$_2$C(O)OCH$_2$CH$_3$·HCl]

The propanoic acid prepared as in Example 5B (1.0 g), Hobt (384 mg), triethylamine (0.4 ml), glycine ethyl ester·HCl (374 mg), dimethylformamide (50 ml) and DCC (586 mg) were combined and stirred for four days at room temperature. Solvent was removed and the residue was passed through a silica column eluting with ethyl acetate. Removal of solvent yielded 990 mg of product. The HCl salt was prepared and triturate in ethyl ether and filtered to yield a white solid.
m.p. 97°-107° C.

Analysis for C$_{27}$H$_{42}$N$_2$O$_4$·HCl: Theory: C, 65.50; H, 8.75; N, 5.66; Found: C, 65.73; H, 8.50; N, 5.76.

EXAMPLE 30

Preparation of
2-[[3-[4-(3-hydroxyphenyl)-3,4-dimethyl-1-piperidinyl]-2-(cyclohexylmethyl)-1-oxopropyl]-amino]acetic acid monohydrate [M-NHCH$_2$C(O)OH·H$_2$O]

The product of Example 29 (1.08 g), lithium hydroxide (302 mg), and water/methanol/THF (20 ml, 1:1:3) were combined and stirred at room temperature for four hours. The reaction mixture was poured into 10% HCl/water and the mixture was extracted with butanol-toluene (v:v, 3:1). The organic layer was washed one time with water, dried over MgSO$_4$, and evaporated to provide 1.05 g of material. This material was subjected to column chromotography eluting with a gradient of ethyl acetate to ethyl acetate/methanol (1:1) providing 510 mg of solid material.

m.p.=112°-116° C.
ms (fd)=430 M$^+$ to 431 M$^+$+1

Analysis for C$_{25}$H$_{38}$N$_2$O$_4$·H$_2$O: Theory: C, 66.90; H, 8.92; N, 6.25; Found: C, 67.10; H, 8.77; N, 6.24.

EXAMPLE 31

Preparation of
N-ethyl-2-[[3-[4-(3-hydroxyphenyl)-3,4-dimethyl-1-piperidinyl]-2-(cyclohexylmethyl)-1-oxo-propyl]amino]acetamide monohydrochloride monohydrate M-NHCH$_2$C(O)NHCH$_2$CH$_3$·HCl·H$_2$O]

The procedure of Example 17 was followed with the ester of Example 29 (400 mg) and ethylamine (20 ml, 70% in H$_2$O) to yield 390 mg of material. This material was subjected to column chromatography eluting with a gradient of ethyl acetate to ethyl acetate/methanol (v:v, 9:1). Solvent removal yielded 200 mg of product.
ms (fd)=457 M$^+$ and 458 M$^+$+1 The HCl salt was prepared and dried at 60° C. to provide 173 mg of white solid.

m.p.=137°-140.5° C.

Analysis for C$_{27}$H$_{43}$N$_3$O$_3$·HCl H$_2$O: Theory: C, 63.32; H, 9.05; N, 8.21; Found: C, 63.12; H, 8.82; N, 7.95.

EXAMPLE 32

Preparation of
N-[2-methylamino-2-oxoethyl]-3-[4-(3-hydroxphenyl)-3,4-dimethyl(-1-piperidinyl]-2-cyclohexylmethyl-propanamide monohydrochloride [M-NHCH$_2$C(O)NHCH$_3$·HCl]

The procedure of Example 31 was followed with the propanamide prepared as in Example 29 (400 mg) and methylamine (20 ml, 40% in water) to provide 380 mg of material which was subjected to column chromatography eluting with a gradient of ethyl acetate to ethyl acetate/methanol (v:v, 9:1). Solvent removal provided 210 mg of product.

ms (fd)=443 M$^+$, 444 M$^+$+1 The HCl salt was prepared and dried to provide 171 mg of solid.
m.p.=131°-135° C.

Analysis for C$_{26}$H$_{41}$N$_3$O$_3$·HCl: Theory: C, 65.0S; H, 8.82; N, 8.75; Found C, 65.37; H, 8.81; N, 8.88.

EXAMPLE 33

Preparation of 2-[[3-[4-(3-hydroxyphenyl)-3,4-dimethyl-1-piperidinyl]-2-(cyclohexylmethyl)-1-oxophenyl]amino]acetamide monohydrochloride [M-NHCH$_2$C(O)NH$_2$·HCl]

The procedure of Example 31 was followed with the propanamide prepared as in Example 29 (400 mg) and ammonium hydroxide (20 ml, 28% in H$_2$O) except the mixture was stirred for three days and then evaporated to dryness under vacuum. 350 mg of material were recovered which was subjected to column chromatography eluting with a gradient of ethyl acetate to ethyl acetate/methanol (v:v, 9:1). Solvent removal provided 240 mg of product.

ms (fd)=429 M+ and 430 M++1 The HCl salt was prepared and dried at 60° C. to provide 186 mg of solid. m.p.=140°-144° C.

Analysis for C$_{25}$H$_{39}$N$_3$O$_3$·HCl: Theory: C, 64.43; H, 8.65; N, 9.02; Found: C, 64.69; H, 8.86; N, 8.93.

EXAMPLE 34

Preparation of 3-[[2-(cyclohexylmethyl)-1-oxo-3-[4-(3-hydroxyphenyl)-3,4-dimethyl-1-piperidinyl]propyl]-amino]-propanoic acid phenylmethyl ester monohydrochloride [M-NH(CH$_2$)$_2$C(O)OCH$_2$(CH$_6$H$_5$)·HCl]

Propanoic acid product of the Example 5B procedure (809 mg), β-alanine benzyl ester-p-tosylate (760 mg), Hobt (293 mg), TEA (0.364 ml), DCC (447 mg), and DMF (80 ml) were combined and stirred at room temperature for three days. The mixture was stripped to dryness and diluted with butanol-toluene (v:v, 3:1) and water. The pH was adjusted to 9.8 with 1N NaOH and the organic layer was separated. The organic layer was dried over K$_2$CO$_3$ and the solvent removed. The residue was diluted with ethyl acetate and passed through a column of silica gel. The recovered product was converted to the HCl salt and triterated with ethyl ether and filtered to provide 600 mg of white solid. m.p.=80°-90° C.

Analysis for C$_{33}$H$_{46}$N$_2$O$_4$·HCl: Theory: C, 69.39; H, 8.29; N, 4.90 ; Found: C, 69.50; H, 8.42; N, 4.93.

EXAMPLE 35

Preparation of 3-[[3-[4-(3-hydroxyphenyl)-3,4-dimethyl-1-piperidinyl]-2-(cyclohexylmethyl)-1-oxopropyl]-amino]propanoic acid hydrochloride [M-NH(CH$_2$)$_2$C(O)OH·HCl]

The propanoic acid ester product of Example 34 (950 mg) was contacted with 5% Pd on carbon in ethanol under 60 pounds per square inch hydrogen pressure. The solvent was stripped and the residue passed through a silica column eluting with methanol to give 760 mg of product. This was converted to the HCl salt to provide 404 mg of white solid. m.p.=115°-120° C.

Analysis for C$_{26}$H$_{40}$N$_2$O$_4$·HCl: Theory: C, 6%.91; H, 8.59; N, 5.82 ; Found C, 6S.04; H, 8.58; N, 5.90.

EXAMPLE 36

Preparation of 3-[[2-(cyclohexylmethyl)-3-[4-(3-hydroxyphenyl)-3,4-dimethyl-1-piperidinyl]-1-oxo-propyl]amino]propanoic acid ethyl ester monohydrochloride [M-NH(CH$_2$)$_2$C(O)OCH$_2$CH$_3$·HCl]

Propanoic acid product of the procedure of Example 5B (1 g), β-alanine ethyl ester hydrochloride (400 mg) triethylamine (263 mg) Hobt (351 mg), were combined in dry dimethylformamide (75 ml) and then DCC (536 mg) was added. These reactants were mixed together at room temperature under nitrogen for 3 days. The reaction mixture was filtered and evaporated to dryness. The residue was dissolved in ethyl acetate, which was washed one time with water, dried over K$_2$CO$_3$ and evaporated to provide 1.74 g of material. This material was subjected to column chromatography eluting with a gradient of ethyl acetate/hexane (v:v, 1:1) to ethyl acetate. Removal of the solvent provided 520 mg of solid which was coverted to the HCl salt to provide 270 mg of solid.

m.p.=86°-89° C.

ms (fd)=472 M+ and 473 M++1

Analysis for C$_{28}$H$_{44}$N$_2$O$_4$·HCl: Theory C, 66.05; H, 8.91; N, 5.51; Found: C, 6S.86; H, 8.72; N, 5.81.

EXAMPLE 37

Preparation of N-[3-(methylamino)-3-oxopropyl]-3-[3,4-dimethyl-4-(3-hydroxyphenyl)-1-piperidinyl]-2-cyclohexylmethylpropanamide monohydrochloride [M-NH(CH$_2$)$_2$C(O)NHCH$_2$CH$_3$·HCl]

The procedure of Example 17 was followed with the propanoic acid ester product of the procedure of Example 36 (450 mg) and ethylamine (20 ml, 70% in H$_2$O) to provide 440 mg of material. This material was subjected to column chromatography eluting with a gradient of ethyl acetate to ethyl acetate/methanol (v:v, 9:1) providing 250 mg of product.

ms (fd)=471 M+ and 472 M++1 This product was coverted to the HCl salt and dried to provide 225 mg of solid.

m.p.=109°-113° C.

Analysis for C$_{28}$H$_{45}$N$_3$O$_3$·HCl Theory: C, 66.18: H, 9.13: N, 8.27; Found: C, 66.36; H, 9.29 N, 8.53.

EXAMPLE 38

Preparation of 3-[[1-oxo-2-cyclohexylmethyl)-3-[4-(3-hydroxyphenyl)-3,4-dimethyl-1-piperidinyl]propyl]-amino]propanamide hydrochloride [M-NH(CH$_2$)$_2$C(O)NH$_2$·HCl]

Propanoic acid ethyl ester prepared as in Example 36 (300 mg) and ammonium hydroxide (15 ml, 28% in H$_2$O) were combined and stirred at room temperature for three days. Upon evaporating to dryness under vacuum, 270 mg of material were recovered. This material was subjected to column chromatography eluting with a gradient of ethyl acetate to ethyl acetate/methanol (v:v, 9:1). Removal of solvent provided 170 mg of product.

ms (fd)=443 M+ and 444 M+1 This product was converted to the HCl salt and dried to provide 108 mg of solid.

m.p.=101°-105° C.

Analysis for C$_{26}$H$_{41}$N$_3$O$_3$·HCl Theory: C, 65.04; H, 8.82; N, 8.75; Found: C, 65.29; H, 9.07; N, 8.87.

EXAMPLE 39

Preparation of 4-[[3-[3,4-dimethyl-4-(3-hydroxyphenyl)-1-piperidinyl]-2-(cyclohexymethyl)-1-oxopropyl]-amino]butanoic acid ethyl ester monohydrochloride [MNH(CH$_2$)$_3$C(O)OCH$_2$CH$_3$·HCl]

The propanoic acid product of the Example 5B procedure (809 mg), ethyl-4-aminobutyrate·HCl (399 mg), HOBT (293 mg), TEA (0.364 ml), DCC (447 mg) were combined in DMF (80 ml) and stirred for 72 hours at room temperature. The reaction mixture was evaporated to dryness under vacuum. The recovered material was subjected to column chromatography eluting with ethyl acetate/hexane (1:1) to yield 610 mgs after solvent removal. This material was converted to the HCl salt yielding 540 mg of white solid.

m.p.=70°-85° C. Analysis: $C_{29}H_{46}N_2O_4 \cdot HCl$ Theory: C, 66.58; H, 9.06; N, 5.35; Found: C, 66.49; H, 9.05; N, 5.30.

EXAMPLE 40

Preparation of
4-[[1-oxo-2-(cyclohexylmethyl)-3-[4-(3-hydroxyphenyl)-3,4-dimethyl-1-piperidinyl]propyl]-amino]-butanamide hydrochloride
[M-NH(CH$_2$)$_3$C(O)NH$_2 \cdot$HCL]

The procedure of Example 17 was followed with the butanoic acid ester of Example 39 (300 mg) and ammonium hydroxide (15 ml, 28%), with the mixture being stirred for three days. 260 mg of material were recovered and subjected to column chromatography eluting with a gradient of ethyl acetate to ethyl acetate/methanol (9:1, v:v). Solvent evaporation under vacuum provided 100 mg of product.

ms (fd)=457 M+

The product was converted to the HCl salt and dried to provide 63 mg of solid.
m.p.=90°-94° C.

Analysis for $C_{27}H_{43}N_3O_3 \cdot HCl$: Theory C, 65.63; H, 8.98; N, 8.50; Found: C, 65.98; H, 8.98; N, 8.35.

EXAMPLE 41

Preparation of
N-[4-(methylamino)-4-oxobutyl]-3-[4-(3-hydroxyphenyl)-3,4-dimethyl-1-piperidinyl]-2-cyclohexylmethylpropanamide monohydrochloride
[M-NH(CH$_2$)$_3$C(O)NHCH$_3 \cdot$HCl]

The procedure of Example 17 was followed with butanoic acid ethyl ester prepared as in Example 39 (400 mg) and methylamine (20 ml, 40% in H$_2$O), except the mixture was stirred overnight. 350 mg of material were recovered and subjected to column chromatography eluting with a gradient of ethyl acetate to ethyl acetate/methanol (v:v, 9:1) to provide 270 mg of product.

ms (fd)=471 M+ and 472 M++1 This product was converted to the HCl salt and dried to provide 250 mg of white solid.
m.p.=89°-94° C.

Analysis for $C_{28}H_{45}N_3O_3 \cdot HCl$: Theory: C, 66.18; H, 9.13; N, 8.29; Found: C, 65.97; H, 9.12; N, 8.08.

EXAMPLE 42

Preparation of
N-[4-(ethylamino)-4-oxobutyl]-3-[4-(3--hydroxyphenyl)-3,4-dimethyl-1-piperidinyl[-2-cyclohexyl-methyl propanamide monohydrate hydrochloride
[M-NH(CH$_2$)$_3$C(O)NHCH$_2$CH$_3 \cdot$HCl$\cdot$H$_2$O]

The procedure of Example 17 was followed with the butanoic acid ethyl ester product of the procedure of Example 39 (400 mg) in ethylamine (20 ml, 70% in H$_2$O) to provide 340 mg of material which was subjected to column chromatoqraphed eluting with a gradient of ethyl acetate to ethyl acetate/methanol (v:v, 9:1). Solvent removal provided 200 mg of product.

ms (fd)=485 M+, 486 M++1 This was converted to the HCl salt and dried to provide 210 mg of white solid.
m.p=95°-100° C.

Analysis for $C_{29}H_{47}N_3O_3 \cdot HCl \cdot H_2O$: Theory: C, 64.48; H, 9.33; N, 7.78; Found: C, 64.19; H, 9.14; N, 7.68.

EXAMPLE 43

Preparation of
2-[3-[4-(3-hydroxyphenyl)-3,4-dimethyl-1-piperidinyl]-1-oxo-2-(phenylmethyl)propyl]-amino]acetic acid ethyl ester hydrochloride [X-OCH$_2$CH$_3 \cdot$HCl]

Propanoic acid [Z-OH] from the procedure of Example 4B (1.23 g), Glycine ethyl ester·HCl (486 mg), Hobt (473 mg), TEA (0.487 ml) were combined in DMF (100 ml) and cooled to 0° C. To this was added DCC (719 mg) and the mixture allowed to warm to room temperature. The mixtured was stirred for three days at room temperature, filtered and the solvent removed under vacuum. The residue was diluted with butanol-toluene (v:v, 3:1) and water. The pH was adjusted to 9.8 with ammonium hydroxide. The organic layer was separated and dried over K$_2$CO$_3$ and the solvent was removed. The residue was passed through a silica column eluting with ethyl acetate/hexane (v:v, 3:1). The solvent was removed to yield 1.17 g of product. This was converted to the HCl salt to provide 1.0 g of white solid.
m.p.=75°-87° C.

Analysis for $C_{27}H_{36}N_2O_4 \cdot HCl$: Theory: C, 66.31; H, 7.63; N, 5.72; Found: C, 66.06; H, 7.55; N, 5.80.

EXAMPLE 44

Preparation of
2-[[3-[4-(3-hydroxyphenyl)-3,4-dimethyl-1-piperidinyl]-1-oxo-2-(phenylmethyl)propyl]-amino]acetic acid monohydrate [X-OH·H$_2$O]

Acetic acid ester prepared as in Example 43 (HCl salt) (600 mg) was dissolved in ethanol (20 ml) and 1N NaOH (2.6 ml) was added. The mixture allowed to stir at room temperature for two hours and the solvent removed under reduced pressure The residue was taken into H$_2$O and the pH adjusted to 7 with 1N HCl. The H$_2$O was removed under vacuum and the residue dried. The residue was slurried in ethanol, filtered, and the solvent removed to yield 500 mg of material. This material was passed through a silica column eluting with ethyl acetate/methanol (3:2). The solvent was removed to yield 450 mg of material. This was recrystallized from an ethyl acetate/methanol (1:1) mixture to provide 378 mg of final product as a white solid.
m.p.=161°-165° C.

Analysis for $C_{25}H_{32}N_2O_4 \cdot H_2O$: Theory: C, 68.16; H, 7.32; N, 6.36 ; Found: C, 68.08; H, 7.30; N, 6.22.

EXAMPLE 45

Preparation of
N-ethyl-2-[[2-(phenylmethyl-)-1-oxo-3-[4-(3-hydroxyphenyl)-3,4-dimethyl-1-piperidinyl]propyl]-amino]ethanamide [X-NHCH$_2$CH$_3$].

Acetic acid ester product prepared as in Example 43 (HCl salt) (300 mg) was combined with ethylamine (50 ml, 70%) and stirred for one hour. The solvent evaporated and the residue dissolved in ethyl acetate. The organic layer was washed with water, dried over K$_2$CO$_3$ and the solvent removed to provide 240 mg of a solid.

ms (fd)=451 M+

Analysis for $C_{27}H_{37}N_3O_3$ Theory: C 71.81 H 8.29 N 9.30; Found: C 71.96 H 8.18 N 9.49.

EXAMPLE 46

Preparation of N-(2-amino-2-oxoethyl)-3-[3,4-dimethyl-4-(3-hydroxyphenyl)-1-piperidinyl]-2-phenylmethyl propanamide monohydrochloride monohydrate [$XNH_2 \cdot HCl \cdot H_2O$]

Acetic acid ester product prepared as in Example 43 (HCl salt) (500 mg), ammonium hydroxide (10 ml, 28%) and methanol (5 ml) were combined and stirred at room temperature overnight. The mixture was evaporated to dryness under vacuum and the residue was partitioned between butanol-toluene (v:v, 3:1) and water. The pH of the water layer was adjusted to 9.8 with 1N NaOH and the layers separated. The organic layer was washed one time with water and dried over $K_2CO_3$. The solvent was evaporated to yield 470 mg of a viscous oil. This oil was passed over a silica column eluting with a gradient of ethyl acetate to ethyl acetate/methanol (v:v, 9:1). Removal of solvent provided 270 mg of an oil.

ms (fd)=423 M+, 424 M+ +1

This product was converted to the HCl salt to provide 250 mg of white solid which was triturated in ethyl acetate and filtered to yield 230 mgs white solid.

m.p.=134°–137° C.

Analysis for $C_{25}H_{34}N_3O_3 \cdot HCl \cdot H_2O$: Theory: C, 62.81; H, 7.59; N, 8.79; Found: C, 62.58; H, 7.31; N, 8.59.

EXAMPLE 47

Preparation of N,N-dimethyl-2-[[3-4-(3-hydroxyphenyl)-3,4-dimethyl-1-piperidinyl]-2-(phenylmethyl)-1-oxypropyl-]amino]acetamide monohydrochloride monohydrate $X$-$N(CH_3)_2 \cdot HCl \cdot H_2O$]

The procedure of Example 46 was followed with acetic acid ester (HCl salt) product of the Example 43 procedure (500 mg), dimethylamine (10 ml, 40 wt. % in water) and methanol (5 ml) with the reaction mixture stirred for two hours. 350 mg of material were recovered which was passed through a silica column eluting with ethyl acetate. 230 mg of product were recovered.

ms (fd)=451 M+ +1 This material was converted to the HCl salt to provide 200 mg of white solid.

m.p.=119°–123° C.

Analysis for $C_{27}H_{37}N_3O_3 \cdot HCl \cdot H_2O$: Theory: C, 64.28; H, 7.85; N, 8.61; Found: C, 64.57; H, 7.68; N, 8.53.

EXAMPLE 48

Preparation of N-(1-methylethyl)-2-[[3-[4-(3-hydroxyphenyl)-3,4-dimethyl-1-piperidinyl]-2-(phenylmethyl)-1-oxopropyl-]amino]acetamide hydrochloride monohydrate $X$-$NHCH(CH_3)_2 \cdot HCl \cdot H_2O$]

Acetic acid ester (HCl salt) product of the procedure of Example 43 (750 mg) [$X$-$OCH_2CH_3$], 2-aminopropane (106 mg), Hobt (243 mg) were mixed in DMF (50 ml) followed by the addition of DCC (371 mg). This mixture was stirred at room temperature for 64 hours under nitrogen. The mixture was evaporated to dryness and the residue dissolved in ethyl acetate, which was then washed two times with water and dried over $K_2CO_3$. The solvent was removed to provide 880 mg of material which was passed through a silica column eluting with ethyl acetate. Solvent Evaporation provided 450 mg of product.

ms (fd)=465 M+, and 466 M+ +1 The HCl salt was formed and the white solid dried at 60° C.

m.p.=124°–128° C.

Analysis for $C_{28}H_{39}N_3O_3 \cdot HCl \cdot H_2O$: Theory: C, 64.66; H, 8.14; N, 8.08; Found: C, 64.83; H, 8.30; N, 8.34.

EXAMPLE 49

Preparation of N-2-propylamino-2-oxoethyl]-3-[4-(3-hydroxyphenyl)-3,4-dimethyl-1-piperidinyl]-2-phenylmethyl propanamide monohydrate hydrochloride. [$XNH(CH_2)_2CH_3 \cdot HCl \cdot H_2O$]

Acetic acid ester (HCl salt) prepared as in Example 43 (750 mg), 1-aminopropane (106 mg) and Hobt (243 mg) were combined in DMF (50 ml) followed by the addition of DCC (371 mg) using the procedure of Example 48. 1.2 g of material were obtained and passed through a silica column eluting with ethyl acetate to provide 500 mg of product.

ms (fd)=465 M+, 466 M+ +1 This product was converted to the HCl salt and dried to provide 510 mg of white solid.

m.p.=115°–120° C.

Analysis for $C_{28}H_{39}N_3O_3 \cdot HCl \cdot H_2O$: Theory: C, 64.66; H, 8.14; N, 8.08; Found: C, 64.91; H, 7.86; N, 7.97.

EXAMPLE 50

Preparation of N-2-[(2-methylpropyl)amino]-2-oxo-ethyl]-3-[3,4-dimethyl-4-(3-hydroxyphenyl)-1-piperidinyl-2-phenylmethyl propanamide monohydrate hydrochloride [$X$-$NHCH_2CH(CH_3)_2 \cdot HCl \cdot H_2O$]

The procedure of Example 48 was followed with acetic acid ester (HCl salt) prepared as in Example 43 (600 mg), 2-methyl-1-aminopropane (102 mg), Hobt (189 mg), dry DMF (50 ml) and DCC (288 mg). 940 mg of material were isolated and passed through a silica column eluting with ethyl acetate to provide 300 mg of product.

ms (fd) of 479 M+.

This product was converted to the HCl salt and dried to provide 210 mg of white solid.

m.p.=107°–110° C.

Analysis for $C_{29}H_{41}N_3O_3 \cdot HCl \cdot H_2O$: Theory: C, 65.21; H, 8.30; N, 7.87; Found: C, 65.51; H, 8.07; N, 7.80.

EXAMPLE 51

Preparation of 2-[[2-(phenylmethyl)-3-[4-(3-hydroxyphenyl)-3,4-dimethyl-1-piperidinyl]-1-oxopropyl]-amino]ethanoic acid 2-propyl ester monohydrochloride [$X$-$OCH(CH_3)_2 \cdot HCl$]

Acetic acid ester (HCl salt) prepared as in Example 43 (1.0 g), isopropyl alcohol (20 ml), and 3 angstrom molecular sieve (50 mg) were combined followed by the addition of isopropyl alcohol saturated with gaseous HCl (20 ml). The reaction mixture was refluxed for 48 hours and the solvent removed. The residue was diluted with water and the pH adjusted to 9.8 with TEA. The mixture was extracted with ethyl acetate which was then dried over $K_2CO_3$. The solvent was removed and the residue passed through a silica column eluting with ethyl acetate. The recovered product was converted to the HCl salt to provide 700 mg of white solid after drying. The solid was triturated in ethyl acetate and filtered to yield 650 mgs of white solid.

m.p. = 75°–120° C. (foam):
Analysis for $C_{28}H_{38}N_2O_4 \cdot HCl$ Theory: C, 66.85; H, 7.81; N, 5.57; Found: C, 66.98; H, 7.64; N, 5.52.

EXAMPLE 52

Preparation of
2-[[2-(phenylmethyl)-1-oxo-3-[4-(3-hydroxyphenyl)-3,4-dimethyl-1-piperidinyl]propyl]amino]-ethanoic acid cyclohexyl ester monohydrochloride
$[X-O-(CH_6H_{11}) \cdot HCl]$ To acetic acid ester (HCl salt) prepared as in Example 43 (1.0 g) and 3 angstrom molecular sieve (0.5 g) was added cyclohexanol (20 ml) followed by cyclohexanol saturated with gaseous HCl (20 ml). The mixture was allowed to stir 72 hours at room temperature. The mixture was then heated to 50° C. for 24 hours, cooled, filtered, and stripped to dryness. The resulting material was triturated in hexane. The solvent was removed, the residue dissolved in water, and the pH adjusted to 9.8 with triethylamine. The Product was extracted with ethyl acetate which was then dried over $K_2CO_3$. The solvent was removed and the residue was passed through a silica column eluting with ethyl acetate/hexane (v:v, 4:1). After removing the solvent, the product was converted to the HCl salt to give 65 mg of white solid.

m.p. = 100°–140° C. (foam):
Analysis for $C_{32}H_{44}N_2O_4 \cdot HCl$: Theory: C, 68.55; H, 7.98; N, 5.16; Found: C, 68.80; H, 7.82; N, 5.05.

EXAMPLE 53

Preparation of
2-[[2-(phenylmethyl)-1-oxo-3-[4-(3-hydroxyphenyl)-3,%-dimethyl-1-piperidinyl]propylamino]-ethanoic acid cyclohexylmethyl ester monohydrochloride
$[X-OCH_2(CH_6H_{11}) \cdot HCl]$ Acetic acid ester prepared as in Example 43 (HCl salt) (7S0 mg) and cyclohexylmethanol saturated with Gaseous HCl (20 ml) were combined and heated to 60° C. for 24 hours. The mixture was evaporated to dryness under vacuum. The residue was diluted with water and ethyl acetate and the pH adjusted to 9.8 with triethylamine. The organic layer was separated, and dried over $K_2CO_3$. The solvent was removed and the residue passed through a silica column eluting with hexane/ethyl acetate (v:v, 1:1). Removal of solvent provided the product which was converted to the HCl salt and triturated in ethyl ether to provide 263 mg of tan solid.

m.p. = 140°–155° C. (foam):
Analysis for $C_{32}H_{44}N_2O_4 \cdot HCl$: Theory: C, 68.98; H, 8.14; N, 5.03; Found: C, 69.18; H, 8.05; N, 4.83.

EXAMPLE 54

Preparation of
2-[2-(phenylmethyl)-1-oxo-3-4-(3-hydroxyphenyl)-3,4-dimethyl-1-piperidinyl]propyl]amino]-ethanoic acid 2-methylpropyl ester monohydrochloride
$[X-OCH_2CH(CH_3)_2 \cdot HCl]$ Acetic acid ester prepared as in Example 43 (HCl salt) (1.0 g), 3 angstrom molecular sieve (0.5 g) and isobutyl alcohol saturated with Gaseous HCl (40 ml) were combined and stirred at room temperature for 72 hours. The mixture was then heated to 50° C. for 24 hours. The reaction was filtered and the filtrate was stripped to dryness. The resulting residue was diluted with water and the pH adjusted to 9.8 with triethylamine. The product was extracted into ethyl acetate and the organic layer dried over $K_2CO_3$. The solvent was removed and the residue passed through a silica column eluting with ethyl acetate/hexane (v:v, 4:1). The recovered product was converted to the HCl salt to provide 500 mg of a white solid.

Analysis for $C_{298}H_{40}N_2O_4 \cdot HCl$: Theory: C, 67.36; H, 7.99; N, 5.41; Found: C, 67.65; H, 7.94; N, 5.36.

EXAMPLE 55

Preparation of
2-[[2-(phenylmethyl)-1-oxo-3-[4-(3-hydroxyphenyl)3,4-dimethyl-1-piperidinyl]propyl]amino]-ethanoic acid phenylmethyl ester hydrochloride
$[XOCH_2(CH_6H_5) \cdot HCl]$ Acetic acid ester prepared as in Example 43 (HCl salt) (1.0 g), 3 angstrom molecular sieve (0.5 g), and benzyl alcohol (40 ml) saturated with Gaseous HCl were combined and stirred at room temperature for 72 hours. The mixture was then heated at 50° C. for 24 hours. The mixture was filtered and the solvent removed under vacuum. The residue was diluted with water and the pH was adjusted to 9.8 with triethylamine. The product was extracted into ethyl acetate which was dried over $K_2CO_3$. The ethyl acetate was evaporated under vacuum and the resulting residue passed through a silica column eluting with ethyl acetate/hexane (v:v, 4:1). The resulting product was converted to the HCl salt and dried to provide 300 mg of white solid.

m.p. = 80°–110° C. (foam):
Analysis for $C_{32}H_{38}N_2O_4 \cdot HCl$ $H_2O$: Theory: C, 67.53; H, 7.26; N, 4.92; Found: C, 67.51; H, 7.09; N, 4.99.

EXAMPLE 56

Preparation of
2-[[2-(phenylmethyl)-1-oxo-3-[4-(3-hydroxyphenyl)-3,4-dimethyl-1-piperidinyl]propyl]amino]-propanoic acid phenylmethyl ester hydrochloride
$[Z-NH(CH_2)_2C(O)OCH_2(CH_6H_5) \cdot HCl]$ Propanoic acid prepared as in Example 4B (1.23 g), benzyl-3-amino-propionate.p-tosylate (1.22 g), Hobt (473 mg) and TEA (0.418 ml) were combined in DMF (100 ml) and stirred ten minutes at 0° C. DCC (719 mg) was then added and the mixture allowed to warm to room temperature and the stirring was continued for three days at room temperature. The solvent was removed and the residue diluted with butanol-toluene (v:v, 3:1) and water. The pH of the aqueous layer was adjusted to 9.8 with ammonium hydroxide and the mixture extracted with butanol-toluene (3:1). The organic layer was separated and dried over $K_2CO_3$. The solvent was removed and resulting residue passed through a silica column eluting with ethyl acetate/hexane (v:v, 3:1). Removal of solvent provided 1.2 g of product. The product was converted to the HCl salt and dried to provide a white solid.

m.p. = 70°–85° C.
Analysis for $C_{33}H_{40}N_2O_4 \cdot HCl$: Theory: C, 70.13; H, 7.31; N, 4.96; Found: C, 70:40; H, 7.27; N, 5.21.

EXAMPLE 57

Preparation of
2-[[3-[4-(3-hydroxyphenyl)3,4-dimethyl-1-piperidinyl]-1-oxo-2-(phenylmethyl)propyl]-amino]propanoic acid monohydrate Z-NH(CH$_2$)$_2$C(O)OH·H$_2$O]

The product of Example 56 (700 mg) was contacted with 5% Pd/C and H$_2$ at 60 psi overnight. The mixture was filtered and the solvent was removed. The residue was diluted with a water/ethanol mixture. The pH was adjusted to 7.0 with 1N NaOH. This solvent was removed and the residue slurried in ethanol and filtered to remove NaCl. The solvent was removed from the filtrate and the residue passed through silica gel column eluting with ethyl acetate/ethanol (v:v, 1:1). The solvent was removed and the solid was dried to provide 366 mg of product.

m.p.=98°-100° C.

Analysis for C$_{26}$H$_{34}$N$_2$O$_4$·H$_2$O Theory: C, 68.39; H, 7.94; N, 6.12; Found: C, 68.59; H, 8.03; N, 5.72.

EXAMPLE 58

Preparation of
[[3-[4-(3-hydroxyphenyl)-3,4-dimethyl-1-piperidinyl]-1-oxo-2-(phenylmethyl)propyl]-amino]propanoic acid ethyl ester monohydrochloride [Z-NH(CH$_2$)$_2$C(O)OCH$_2$CH$_3$·HCl]

Propanoic acid prepared as in Example 4B (1.65 g), β-alanine ethyl ester.HCl (691 mg), TEA (454 mg), Hobt (608 mg) and dried DMF (75 ml) were combined followed by DCC (928 mg) and stirred 64 hours at room temperature under nitrogen. The mixture was evaporated to dryness and the residue partitioned between ethyl acetate and water. The layers were separated with the organic layer being washed with water, dried over K$_2$CO$_3$ and evaporated to dryness to provide 2.0 g of material. This material was passed through a silica column eluting with a gradient of hexane/ethyl acetate (v:v, 1:1) to ethyl acetate providing 1.26 g of product. This product was converted to the HCl salt and dried to provide 1.3 g of white solid.

m.p.=119°-124° C.
ms (fd)=466 M+

EXAMPLE 59

Preparation of
N-(methyl)-3-[[3-[4-(3-hydroxyphenyl)-3,4-dimethyl-1-piperidinyl]-2-(phenylmethyl)-1-oxopropyl]amino]-propanamide monohydrochloride [Z-NH(CH$_2$)$_2$C(O)NHCH$_3$·HCl]

Propionic acid ethyl ester prepared as in Example 58 (450 mg), methylamine (15 ml, 40% in water), and methanol (10 ml) were combined and stirred at room temperature for three hours. The reaction was evaporated to dryness. The residue was partitioned between butanol/toluene (v:v, 3:1) and water. The H$_2$O layer was adjusted to a pH of 9.8 with 1N NaOH and the layers separated. The organic layer was washed one time with water, dried over K$_2$CO$_3$, and evaporated to provide 440 mg of material. This material was subjected to column chromatography eluting with a gradient of ethyl acetate to ethyl acetate/methanol (v:v, 9:1) providing 344 mg of product.

ms (fd)=451 M+, 452 M++1

The product was converted to the HCl salt and dried to provide 260 mg of white solid.

m.p=95°-99° C. (foam):

Analysis for C$_{27}$H$_{37}$N$_3$O$_3$·HCl: Theory: C, 66.45; H, 7.85; N, 8.61; Found: C, 66.75; H, 7.99; N, 8.46.

EXAMPLE 60

Preparation of
N-(ethyl)-3-[[3-[4-(3-hydroxyphenyl)-3,4-dimethyl-1-piperidinyl]-2-(phenylmethyl)-1-oxopropyl]amino]-propanamide monohydrochloride [Z-NH(CH$_2$)$_2$C(O)NHCH$_2$CH$_3$·HCl]

The procedure of Example 59 was followed using propionic acid ethyl ester prepared as in Example 58 (400 mg) and ethylamine (20 ml, 70 wt. % in water) with stirring for 3.5 days. The 380 mg of material recovered was subjected to column chromatography eluting with a gradient of ethyl acetate to ethyl acetate/methanol (v:v, 1:1) providing 360 mg of product.

ms (fd)=465 M+, 466 M++1

This material was converted to the HCl salt and dried to provide 300 mg of white solid.

m.p.=86°-90° C.

Analysis for C$_{28}$H$_{39}$N$_3$O$_3$·HCl: Theory C, 66.98; H, 8.03; N, 8.37; Found: C, 66.69; H, 7.89; N, 8.28.

EXAMPLE 61

Preparation of
4-[[3-[4-(3-hydroxyphenyl)-3,4-dimethyl-1-piperidinyl]-1-oxo-2-(phenylmethyl)propyl]-amino]butanoic acid ethyl ester monohydrochloride monohydrate [Z-NH(CH$_2$)$_3$C(O)OCH$_2$CH$_3$·HCl·H$_2$O]

Propanoic acid prepared as in Example 4B (HCl salt) (530 mg), TEA (0.452 ml), ethyl-4-aminobutyrate·HCl (297 mg), Hobt (218 mg), DMF (60 ml), were combined followed by the addition of DCC (333 mg). The mixture was stirred at room temperature for three days, filtered and the solvent removed. The residue was diluted with a water/ethyl acetate mixture and the water layer adjusted to a pH of 9.8 with TEA. The mixture was extracted with ethyl acetate and the organic layer separated and dried over K$_2$CO$_3$. The solvent was removed to yield 1.0 gram of material. This was passed through a silica gel column eluting with ethyl acetate. The solvent was removed to yield 300 mg of product. This product was converted to the HCl salt to give 370 mg of white solid.

m.p.=65°-70° C.

Analysis for C$_{26}$H$_{41}$N$_2$O$_4$·H$_2$O·HCl: Theory: C, 65.09; H, 8.09; N, 5.23; Found: C, 65.26; H, 7.74; N, 5.53.

EXAMPLE 62

Preparation of
N-(methyl)-4-[[3-]4-(3-hydroxyphenyl)-3,4-dimethyl-1-piperidinyl]-2-(phenylmethyl)-1-oxopropyl]amino]-butanamide monohydrochloride monohydrate [Z-NH(CH$_2$)$_3$C(O)NHCH$_3$·HCl·H$_2$O]

The procedure of Example 59 was followed with the product from the procedure of Example 61 (HCl salt) (400 mg), methylamine (10 ml, 40 wt. % in water) and methanol (10 ml) with a three hour reaction time. 400 mg of material were recovered and subjected to column chromatography eluting with a gradient of ethyl acetate to ethyl acetate/methanol (v:v, 9:1). After evaporation of solvent, 280 mg of product were recovered.

ms (fd)=465 M+, 466 M++1

This material was converted to the HCl salt and dried to provide 260 mg of white solid.

m.p.=90°-93° C. (foam):

Analysis for $C_{28}H_{39}N_3O_3 \cdot HCl \; H_2O$: Theory: C, 64.78; H, 7.96; N, 8.09; Found: C, 64.38; H, 7.73; N, 7.89.

EXAMPLE 63

Preparation of
4-[[3-[4-(3-hydroxyphenyl)-3,4-dimethyl-1-piperidinyl]-2-(phenylmethyl)-1-oxopropyl]-amino]butanamide monohydrochloride -NH(CH$_2$)$_3$C(O)-NH$_2$·HCl]

The procedure of Example 59 was followed with the product from the procedure of Example 61 (HCl salt) (400 mg), ammonium hydroxide (10 ml, 28% in water) and methanol (5 ml) with the reaction mixture heated at 40° C. for two days. The 400 mg of material recovered was subjected to column chromatography eluting with a gradient of ethyl acetate to ethyl acetate/methanol (v:v, 9:1) which provided 250 mg of product.

ms (fd)=451 M+

This product was converted to the HCl salt and dried to provide 200 mg of tan solid.

m.p.=101°-107° C.

Analysis for $C_{27}H_{37}N_3O_3 \cdot HCl$: Theory: C, 66.4; H, 7.85; N, 8.61; Found: C, 66.04; H, 7.86; N, 8.46.

EXAMPLE 64

Preparation of
N-(ethyl)-4-[[3-4-(3-hydroxyphenyl)-3,4-dimethyl-1-piperidinyl]-2-(phenylmethyl)-1-oxopropyl]amino]-butanamide monohydrochloride
[Z-NH(CH$_2$)$_3$C(O)NHCH$_2$CH$_3$·HCl]

The procedure of Example 59 was followed with the product from the procedure of Example 61 (HCl salt) (450 mg) and ethylamine (15 ml, 70% in water) with stirring for 3.5 days to provide 440 mg of material. This material was subjected to column chromatography eluting with a gradient of ethyl acetate to ethyl acetate/methanol (v:v, 1:1) providing 230 mg of product.

ms (fd)=479 M+, 480 M++1

This product was converted to the HCl salt and dried to provide 210 mg of white solid.

m.p.=105°-110° C.

Analysis for $C_{29}H_{41}N_3O_3 \cdot HCl$: Theory: C, 67.49; H, 8.20; N, 8.14; Found: C, 67.62; H, 8.28; N, 8.07.

EXAMPLE 65

Preparation of
[[2-[[4-(3-hydroxyphenyl)-3,4-dimethyl-1-piperidinyl]-methyl]-1-oxo-3-phenylpropyl]-methylamino]acetic acid ethyl ester monohydrochloride.
Z-N(CH$_3$)CH$_2$C(O)OCH$_2$CH$_3$·HCl]

Product from the procedure of Example 4B (1.5 g), sarcosine ethyl ester.HCl (614 mg), TEA (405 mg), Hobt (540 mg) were combined in dry DMF (75 ml) and then DCC (824 mg) was introduced. The mixture was stirred at room temperature under nitrogen for three days. The mixture was filtered and evaporated to dryness. Resulting residue was dissolved in ethyl acetate, washed one time with water and dried over K$_2$CO$_3$. Evaporation of the solvent yielded 1.72 g of material. This material was subjected to column chromatography eluting with a gradient of hexane/ethyl acetate (1:1) to ethyl acetate. The solvent was removed to yield 910 mg of product. A portion of this product was converted to the HCl salt to produce a white solid.

ms (fd)=466 M+ m.p.=91°-95° C.

Analysis for $C_{28}H_{38}N_2O_4 \cdot HCl$: Theory: C, 66.85; H, 7.81; N, 5.57; Found: C, 66.63; H, 7.81; N, 5.62.

EXAMPLE 66

Preparation of
[[2-[[4-(3-hydroxyphenyl)-3,4-dimethyl-1-piperidinyl]-methyl]-1-oxo-3-phenylpropyl]-methylamino]acetic acid monohydrate [Z-N(CH$_3$)CH$_2$C(O)OH·H$_2$O]

Product from the procedure of Example 65 (660 mg) and lithium hydroxide (176 mg) were combined in a mixture of THF/H$_2$O/methanol (20 ml, 3:1:1) and stirred at room temperature for three hours. The reaction mixture was poured into 10% HCl in water and extracted with a butanol-toluene (3:1) solution. The organic layer was washed with water and dried over K$_2$CO$_3$. Evaporation of the solvent under vacuum yielded 700 mg of a semi-solid material. This material was subjected to column chromatography eluting with a gradient of ethyl acetate to ethyl acetate/methanol (v:v, 1:1). The solvent was removed to yield 350 mg of solid material.

ms (fd)=438 M+, 439 M++1

This material was recrystallized from ethyl acetate to yield 220 mg of crystalline product.

m.p. of 134°-136° C.

Analysis for $C_{26}H_{34}N_2O_4 \cdot H_2O$: Theory: C, 68.39; H, 7.95; N, 6.39; Found: C, 68.25; H, 7.76; N, 6.11.

EXAMPLE 67

Preparation of
[[2-[2-[4-(3-hydroxyphenyl)-3,4-dimethyl-1-piperidinyl]methyl]-3-phenyl-1-oxopropyl]-amino]acetyl]amino]acetic acid ethyl ester monohydrochloride
[Z-NHCH$_2$C(O)NHCH$_2$C(O)OCH$_2$CH$_3$·HCl]

The procedure of Example 65 was used with the product from the procedure of Example 48 [Z-OH] (1.5 g), Glycyl Glycine ethyl ester·HCl (786 mg), TEA (405 mg), Hobt (540 mg), dry DMF (75 ml) and DCC (824 mg). 1.36 g of material were recovered. This material was passed over a silica column eluting with ethyl acetate to provide 790 mg of product.

ms (fd)=509 M+

A portion of the material was converted to the HCl salt and dried to yield a white solid.

m.p.=105°-110° C.

Analysis for $C_{29}H_{39}N_3O_5 \cdot HCl$: Theory: C, 63.78; H, 7.38; N, 7.69; Found: C, 63 77; H, 7.47; N, 7.75.

EXAMPLE 68

Preparation of
N-(carboxylmethyl-)-2-[[3-[4-(3-hydroxyphenyl)-3,4-dimethyl-1-piperidinyl]-2-(phenylmethyl)-1-oxopropyl-]amino]acetamide monohydrate[Z-NHCH$_2$C(O)NHCH$_2$C(O)OH·H$_2$O]

Procedure of Example 66 was followed with the ester product from Example 67 (500 mg) and lithium hydroxide (126 mg) in THF/H$_2$O/methanol (20 ml, 12:4:4). The mixture was stirred four hours at room temperature and 400 mg of material recovered. This material was passed over a silica column eluting with a gradient of ethyl acetate/methanol (v:v, 9:1) to methanol to provide 210 mg of solid product.

m.p.=124.5°-127° C.

ms (fd)=482 M+

Analysis for $C_{27}H_{35}N_3O_5 \cdot H_2O$: Theory: C, 64.91; H, 7.47; N, 8.41; Found: C, 64.64; H, 7.28; N, 8.62.

EXAMPLE 69

Preparation of
N-[2-(dimethylamino)ethyl]-3-[4-(3-hydroxyphenyl)-3,4-dimethyl-1-piperidine]-2-phenylmethylpropanamide dihydrochloride [Z-NH(CH$_2$)$_2$-N(CH$_3$)$_2$·2HCl]

Procedure of Example 65 was followed with product from the procedure of Example 4B (1 g), Dimethylethylene Diamine (238 mg), Hobt (364 mg), dry DMF (50 ml) and DCC (556 mg). After evaporating the solvent, the residue was dissolved in a butanol/toluene mixture (3:1) which was washed one time with water and dried over K$_2$CO$_3$. The solvent was evaporated to provide 1.94 g of crude material. This material was subjected to column chromatography eluting with a gradient of ethyl acetate/methanol (v:v, 9:1) to ethyl acetate/methanol (v:v, 1:1). Removal of solvent provided 700 mg of product.

ms (fd) = 437 M+, 438 M+ +1

This product was coverted to the di-hydrochloride salt yielding a white solid.

m.p. = 89°–93° C.

Analysis for C$_{27}$H$_{39}$N$_3$O$_2$·2HCl: Theory: C, 63.52; H, 8.10; N, 8.23; Found: C, 63.32; H, 8.20; N, 8.42.

EXAMPLE 70

Preparation of 2-methyl amine, 4-ethyl-oxadiazole monohydrochloride

A. Sodium (9.2 g) was added to methanol (200 ml) to provide sodium methoxide. Hydroxylamine hydrochloride (26.2 g) was then added. Propionitrile (24.16 g) in methanol (50 ml) was added dropwise. The mixture was then stirred for 48 hours at room temperature. The solvent was removed and the solid was taken into ethyl ether and filtered. The ether filtrate was removed and the residue was passed through a silica column eluting with ethyl acetate to provide 13 g of N-Hydroxy-propaneinidamide [H$_3$CCH$_2$C(NHOH)NH$_2$].

ms (fd) = 89 M+

B. Glycine ethyl ester hydrochloride (27.92 g) was combined with a mixture of water (382 ml) and dioxane (700 ml) and 1N NaOH (380 ml). To this mixture was added di-tert-butyldicarbonate (94 g) dropwise while maintaining the reaction mixture at 0°–5° C. The mixture was then stirred overnight at room temperature. Dioxane was removed under vacuum and the remaining mixture extracted with ethyl acetate. The organic layer was recovered and dried over K$_2$CO$_3$. The solvent was removed to yield 40 g of material. Bulb to bulb distillation at 145° C. under 0.05 mm Hg provided 20 g of di-tert-butyldicarbonate-glycine ethyl ester as a colorless oil. [(CH$_3$)$_3$COC(O)NHCH$_2$C(O)OCH$_2$CH$_3$]

Analysis: (C$_9$H$_{17}$NO$_4$) Theory: C, 53.19; H, 8.43; N, 6.89; Found: C, 53.05; H, 8.12; N, 6.80.

ms (fd) = 203 M+

C. To ethanol (20 ml) under a nitrogen blanket was added sodium (436 mg) followed by powdered molecular sieve (4 angstrom) (20 mg) and the oxime from Example 70A above (1.3 g). To this mixture was added the product from Example 70B. above (3.26 g) dropwise as a solution in ethanol (20 ml). The mixture was then refluxed for 16 hours, filtered over celite and the solvent removed The resulting oil was partitioned between methylene chloride and water. The organic layer was dried over sodium sulfate. The solvent was removed under vacuum to provide a yellow oil (3.0 g). This material was passed through a silica column eluting with ethyl acetate to provide 1.0 g of oxadiazole.

Analysis: C$_{10}$H$_{17}$N$_3$O$_3$ Theory: C, 53.32; H, 6.71; N, 18.66; Found: C, 52.12; H, 7.59; N, 18.99.

ms (fd) = 228 M+ +1

To 900 mg of the oxadiazole were added dioxane (60 ml) and 1N HCl (70 ml). The mixture was allowed to stir for two hours at room temperature. Water was removed under vacuum. Acetonitrile (100 ml) was added and solvent removed under vacuum. The product was recrystallized from acetonitrile to afford 430 mg of solid product.

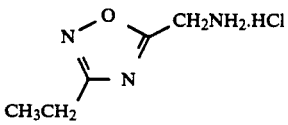

m.p. = 158°–161° C.

ms (fd) = 127 M+

Analysis for C$_5$H$_9$N$_3$O·HCl Theory: C, 36.71; H, 6.16; N, 25.68; Found C, 35.83; H, 5.84; N, 24.86.

EXAMPLE 71

Preparation of
3-[4-(3-hydroxyphenyl)-3,4-dimethyl1-piperidinyl]-2-(phenylmethyl)-N-[(3-ethyl-1,2,4-oxadiazol-5-yl)methyl]propanamide

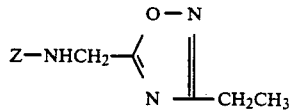

Carboxylic acid product from the procedure of Example 4B (918 mg), amine.HCl product from Example 70 C. (400 mg), Hobt (338 mg), TEA (253 mg), dry DMF (75 ml) and DCC (515 mg) were combined and stirred at room temperature under nitrogen for three days. The mixture was then evaporated under vacuum to dryness. The residue dissolved in ethyl acetate, washed two times with water and the solution dried over K$_2$CO$_3$. The liquid was evaporated under vacuum to provide 1.71 g of material. This material was subjected to column chromatography eluting with a gradient of hexane/ethyl acetate (1:1) to ethyl acetate to afford 710 mg of a viscous oil. This product was converted to HCl salt.

ms (fd) = 476 M+, 477 M+ +1 m.p. = 103°–107° C.

Analysis for C$_{28}$H$_{36}$N$_4$O$_3$·HCl: Theory: C, 65.55; H, 7.27; N, 10.92; Found C, 65.26; H, 7.15; N, 10.70.

EXAMPLE 72

Preparation of 2-(2-Aminoacetyl)(amino)-N-(Phenylmethyl)-acetamide
[H$_2$NCH$_2$C(O)NHCH$_2$C(O)NHCH$_2$C(O)NHCH$_2$-(C$_6$H$_5$)]

A. The procedure of Example 65 was followed with t-butoxycarbon-yl glycine (3 g), benzylamine (1.82 g), Hobt (2.30 g) and DCC (3.50 g) to provide 5.16 g of solid product. t-butoxycarbonyl-2-Amino-N-(Phenylmethyl)-acetamide[(CH$_3$)$_3$COC(O)-NH-CH$_2$-C(O)-NH-CH$_2$-C$_6$H$_5$]

B. The product from 72A above (5.16 g) was combined with 6N HCl (200 ml) and stirred overnight at room temperature. The mixture was then diluted with water (200 ml) and the pH adjusted to 11.5 with NaOH (50%) and ice. This mixture was extracted with a mixture of butanol and toluene (3:1). The organic layer was backwashed one time with water dried over $K_2CO_3$ and evaporated under vacuum to provide 2.1 g of solid material. This material was subjected to column chromatography eluting with a gradient of ethyl acetate/methanol (v:v, 9:1) to ethyl acetate/methanol (v:v, 1:1). 1.60 g of product was recovered. 2-Amino-N-(Phenylmethyl)-Acetamide[$H_2NCH_2C(O)NHCH_2C_6H_5$].

ms (fd) = 164 M+

C. Product from 72B above (1.5 g), t-butoxycarbonyl glycine (1.59 g), Hobt (1.85 g) and dry DMF (75 ml) were combined followed by DCC (1.22 g). The mixture was stirred under nitrogen at room temperature for three days. The resulting mixture was filtered and evaporated to dryness. The residue was dissolved in ethyl acetate, filtered and dried over $K_2CO_3$. The solvent was evaporated to provide 8.14 g of butoxycarbonyl-2-(2-amineacetyl)-(amino)-N-(Phenylmethyl)-acetamide[$(CH_3)COC(O)NHCH_2C(O)NHCH_2C(O)NHCH_2C_6H_5$].

D. Product from 72C above (8.14 g) was combined with 6N HCl (150 ml) using the procedure of Example 72B to provide 2 g of product. This material was subjected to column chromatography eluting with a gradient of ethyl acetate to ethyl acetate/methanol (1:1) providing 700 mg of crystalline product. [$H_2NCH_2C(O)NHCH_2C(O)NHCH_2C_6H_5$].

m.p. = 113°–116° C.
ms (fd) = 201 M+

EXAMPLE 73

Preparation of X-NH-$CH_2C(O)$-NH-$CH_2C_6H_5$

Carboxylic acid product of the procedure of Example 4B (886 mg), amine product from Example 72 D (700 mg), Hobt (405 mg) and dry DMF (50 ml) were combined and then DCC (618 mg) was added. This mixture was stirred 72 hours at room temperature, filtered and evaporated under vacuum to provide 2.0 g of material. This material was subjected to column chromatography eluting with a gradient of ethyl acetate to ethyl acetate/methanol (v:v, 9:1) providing 860 mg of product.

ms (fd) = 570 M+, 571 M+ +1

This product was converted to the HCl salt.
m.p. = 119°–122° C.

Analysis $C_{34}H_{42}N_4O_4 \cdot HCl$: Theory: C, 67.26; H, 7.14; N, 9.23; Found: C, 67.48; H, 7.07; N, 9.12.

EXAMPLE 74

Preparation of $NH_2CH_2C(O)N(CH_3)CH_2C(O)OCH_2CH_3 \cdot HCl$

A. t-butoxycarbonyl glycine (3 g), Sarcosine Ethyl Ester·HCl (2.61 g), TEA (1.72 g), Hobt (2.30 g) and DMF (125 ml) were combined and DCC (3.5 g) was added. This mixture was stirred for 72 hours at room temperature, filtered and evaporated to dryness under vacuum. 8.1 g of material was recovered. This was passed through a silica column eluting with a gradient of ethyl acetate to ethyl acetate/methanol (1:1) providing 2.9 g. of product ($CH_3)_3OC(O)NHCH_2C(O)N(CH_3)CH_2C(O)OCH_2CH_3$].

ms (fd) = 274 M+, 275 M+ +1

B. The product from Example 74A (2.90 g), 1N HCl (50 ml), and ethyl acetate (10 ml) were combined and stirred at room temperature for three hours. The mixture was evaporated to dryness. The residue triturated in acetonitrile and ethyl ether The solid which formed was filtered to provide 900 mg of the HCl salt. [$H_2NCH_2C(O)N(CH_3)CH_2C(O)OCH_2CH_3 \cdot HCl$].

ms (fd) = 174 M+

EXAMPLE 75

Preparation of X-N($CH_3$)$CH_2C(O)OCH_2CH_3$

Carboxylic acid product from the procedure of Example 4B (Z-OH) (1.15 g), product from Example 74B (900 mg), TEA (434 mg), Hobt (580 mg) and dry DMF (50 ml) were combined followed by the addition of DCC (886 mg). The mixture was stirred for three days at room temperature under nitrogen. The mixture was filtered and evaporated to dryness The residue was dissolved in ethyl acetate, washed one time with water, dried over $K_2CO_3$ and the solvent evaporated to provide 2.47 g of material. This was subjected to column chromatography eluting with a gradient of ethyl acetate to ethyl acetate/methanol (v:v, 9:1) providing 1.7 g of material This was again passed through a silica column eluting with ethyl acetate to provide 150 mgs of semi-solid material.

ms (fd) = 523 M+, 524 M+ +1

The material was converted to HCl salt to yield 100 mgs a white powder.

m.p. = 104°–107° C.

Analysis for $C_{30}H_{41}N_3O_5 \cdot HCl$: Theory: C, 64.33; H, 7.56; N, 7.50; Found: C, 64.61; H, 7.55; N, 7.27.

EXAMPLE 76

Preparation of $H_2NCH_2C(O)NHCH_2C(O)NHCH_2CH_3$

A. t-butoxycarbonyl- glycine (3 g), ethylamine.HCl (1.39 g), TEA (1.72 g), Hobt (2.3 g) and dry DMF (100 ml) were combined and DCC (3.5 g) was added. The mixture was stirred for three days at room temperature under nitrogen, then filtered and evaporated to dryness. 6 g of material was recovered. This material was subjected to column chromatography eluting with a gradient of ethyl acetate to ethyl acetate/methanol (1:1) providing 4.01 g of ($CH_3)_3COC(O)NHCH_2C(O)NHCH_2CH_3$.

ms (fd) = 202 M+

B. Product from 76A above (4 g) and 6N HCl (150 ml) were mixed and stirred overnight at room temperature. Acetonitrile was added and the solution was evaporated to dryness. The resulting solid was slurried in ethyl ether, filtered and dried to provide 1.84 g. of $H_2NCH_2C(O)NHCH_2CH_3 \cdot HCl$.

ms (fd) = 102 M+

C. The product from 76B above (1.80 g), t-butoxycarbonylglycine (2.28 g), TEA (1.31 g), Hobt (1.76 g) and dry DMF (150 ml) were combined and DCC (2.68 g) was added. The mixture was stirred for three days at room temperature under nitrogen, filtered and evaporated to dryness. The residue was dissolved in ethyl acetate which was washed one time with water, dried over $K_2CO_3$ and evaporated to provide 2.15 g of material. This material was subjected to column chromatography eluting with a gradient of ethyl acetate/methanol (v:v, 9:1) to ethyl acetate/methanol (v:v, 1:1) providing 920 mg of ($CH_3)_3COC(O)$-$NHCH_2C(O)NHCH_2C(O)NHCH_2CH_3$.

ms (fd) = 259 M+

D. The product from 76C above (900 mg) and 6N HCl (40 ml) were combined as in Example 74 B to provide 700 mg of product as the HCl salt.
ms (fd)=160 M+

EXAMPLE 77

Preparation of X-NHCH$_2$C(O)NHCH$_2$C(O)NHCH$_2$CH$_3$

The procedure of Example 76A was followed with the carboxylic acid prepared from the procedure of Example 4B (Z-OH) (774 mg), amine.HCl product from Example 76 D (458 mg), TEA (293 mg), Hobt (391 mg), dry DMF (50 ml) and DCC (597 mg). 1.74 g of material was recovered. This material was subjected to column chromatography eluting with a gradient of ethyl acetate to ethyl acetate/methanol (1:1) providing 510 mg of product.
ms (fd)=508 M+, 509 M++1
This product was converted to HCl salt to provide 400 mg of solid.
m.p.=110°–115° C.
Analysis for C$_{29}$H$_{40}$N$_4$O$_4$·HCl: Theory: C, 63.90; H, 7.58; N, 10.28; Found: C, 64.16; H, 7.29; N, 10.06.
In Examples 78 thru 82, W is

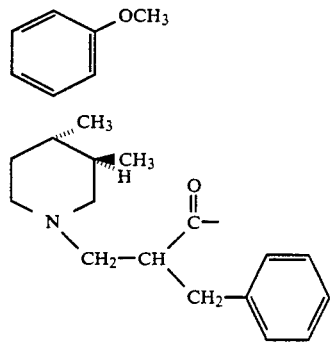

EXAMPLE 78

Preparation of W-OCH$_2$CH$_3$

A. Trans-(+)- 1,3,4-trimethyl-4-(3-methoxyphenyl)-piperidine (3.48 g) vinyl chloroformate (2.73 ml) and proton sponge (7.13 g) were mixed in 1, 2-dichloroethane (150 ml), refluxed for 2 hours, cooled to room temperature and evaporated to dryness. The resulting residue was dissolved in ethyl ether, washed two times with cold 1N HCl, one time with water, dried over K$_2$CO$_3$, and evaporated to dryness to provide 4.51 g of the carbamate product. The carbamate was mixed with ethanol (100 ml) and ethanol/gaseous HCl (100 ml) and refluxed for 1.5 hours. The mixture was cooled to room temperature and evaporated to dryness. The residue was dissolved in 1N NaOH and ethyl ether added. The ether layer was separated, washed with water, dried over K$_2$CO$_3$ and evaporated to provide 3.0 grams of material. This was vacuum distilled in a bulb-to-bulb distillation apparatus at 220° C. and 0.1 mmHg to provide 2.86 g of trans-3,4-dimethyl-4-(3-methoxyphenyl)-piperidine.

B. The product from 78A above (2.86 g) and 3-phenyl-2-(ethoxycarbonyl)-1-propene prepared as in Example 2 (2..72 g) and methanol (50 ml) were mixed and stirred at room temperature under nitrogen for 10 days. The mixture was evaporated 2 times and rediluted with methanol on day 5 and day 9. On day 10 the mixture was evaporated to dryness to provide 5.46 g of material which was subjected to column chromatography eluting with a gradient of hexane to ethyl acetate. Removal of solvent provided 4.05 g of product.
ms (fd)=409 M+, 410 M++1
A portion of the product was converted to the HCl salt.
m.p.=61°–64° C.
Analysis for C$_{26}$H$_{35}$NO$_3$·HCl: Theory: C, 70.01; H, 8.13; N, 3.14; Found: C, 70.00; H, 8.02; N 3.17.

EXAMPLE 79

Preparation of W-OH

The method of Example 12 was followed with W-OCH$_2$CH$_3$ prepared as in Example 78B (2.03 g) and lithium hydroxide (6.29 mg) in THF/H$_2$O/methanol (63:21:21). Evaporation of the solvent yielded 1.82 grams of crystalline material as the HCl salt. This material was recrystallized from acetonitrile to provide 610 mg of crystalline product.
ms (fd)=481 M+
m.p.=196.5°–198° C.
Analysis C$_{24}$H$_{31}$NO$_3$·HCl: Theory: C, 68.77; H, 7.72; N, 3.35; Cl, 8.48; Found: C, 68.84; H, 7.79; N, 3.33; Cl 8.49.

EXAMPLE 80

Preparation of W-NHCH$_3$

W-OCH$_2$CH$_3$ prepared by the procedure of Example 78B (700 mg) and methylamine (25 ml 40% weight percent in water), were mixed and stirred at 50° C. for 4 days. The reaction mixture was evaporated to dryness and the residue was partitioned between a butanol-toluene (3:1) mixture and water. The pH of the water was adjusted to 9.8 with 1N NaOH and layers were separated. The organic layer was washed one time with water and dried over K$_2$CO$_3$ and evaporated to provide 600 mg of material. This material was subjected to column chromatography eluting with a gradient of hexane/ethyl acetate (9:1) to ethyl acetate providing 140 mg of product.
ms (fd)=396 M+
This product was converted to the HCl salt and dried to provide 110 mg of solid.
m.p.=86°–90° C.
Analysis for C$_{25}$H$_{34}$N$_2$O$_2$·HCl: Theory: C, 69.67; H, 8.18; N, 6.50; Found: C, 69.91; H, 8.35; N, 6.33.

EXAMPLE 81

Preparation of W-NHCH$_2$C(O)OCH$_2$CH$_3$

W-OH prepared as in Example 79 (4.15 g), glycine ethyl ester.HCl (1.40 g), TEA (1.01 g), Hobt (1.35 g) and dry DMF (300 ml) were combined and DCC (2.06 g) was then added. The mixture was stirred at room temperature under nitrogen for 3 days, filtered and evaporated to dryness. The residue was dissolved in ethyl acetate, washed with water, dried over K$_2$CO$_3$ and evaporated under vacuum to provide 5.65 g of material. This material was subjected to column chromatography eluting with a gradient of hexane/ethyl acetate (9:1) to ethyl acetate providing 3.40 g of product.
ms (fd)=466 M+
2 g of this material were converted to the HCl salt and dried to provide 2.13 g of white solid.
m.p.=122°–126° C.

Analysis for $C_{28}H_{38}N_2O_4 \cdot HCl$ Theory: C, 66.85; H, 7.81; N, 5.57; Found: C, 67.11; H, 7.99; N, 5.61.

EXAMPLE 82

Preparation of W-NHCH$_2$C(O)NHCH$_3$

The procedure of Example 80 was followed with W-NH·CH$_2$C(O)OCH$_2$CH$_3$ prepared as in Example 81 (600 mg) and methylamine (25 ml, 40 wt % in water) for 2 hours at room temperature. 580 mg of product was recovered. This was passed over a silica column eluting with ethyl acetate to provide 350 mg of material.

ms (fd)=451 M+

This was converted to the HCl salt and dried to provide 380 mg of a white solid.

m.p.=101°–106° C.

Analysis for $C_{27}H_{37}N_3O_3 \cdot HCl$: Theory: C, 66.44; H, 7.85; N, 8.61; Found: C, 66.25; H, 7.90; N, 8.58.

EXAMPLE 83

Preparation of W-NHCH$_2$C(O)NHCH$_2$CH$_3$

The procedure of Example 80 was followed with W-NHCH$_2$C(O)OCH$_2$CH$_3$ prepared as in Example 81 (600 mg) and ethylamine (25 ml, 70 wt % in water stirring for two hours at room temperature. 610 mg of material were recovered. This material was passed over a silica column eluting with ethyl acetate to provide 400 mg of product.

ms (fd)=465 M+

This product was converted to the HCl salt and dried to provide 425 mg of white solid.

m.p.=103°–108° C.

Analysis for $C_{28}H_{39}N_3O_3 \cdot HCl$: Theory: C, 66.98; H, 8.03; N, 8.37; Found: C, 66.71; H, 8.11; N, 8.38.

EXAMPLE 84

A Preparation of N,N-dimethyl-2-hydroxyacetamide

Methyl-2-hydroxyethanoate (10 g) and dimethylamine (100 ml, 40 weight percent in water) were mixed and stirred at room temperature for three hours. The mixture was evaporated to dryness to provide approximately 10 g of material. This material was subjected to column chromatography eluting with a gradient of hexane/ethyl acetate (V:V, 4:1) to ethyl acetate. Removal of the solvent provided 8.12 g of crystalline product.

ms (fd)=103 M+ m.p.=40°–42° C.

I.R.=1655.4 cm$^{-1}$ (carbonyl)

Analysis for $C_4H_9NO_2$: Theory: C, 46.59; H, 8.80; N, 13.59; Found: C, 46.44; H, 8.69; N, 13.60.

B. Preparation of N-methyl-2-hydroxyacetamide

The procedure of 84A was followed using methylamine (100 ml, 40 weight percent in water) as the amine. 10.2 g of material was obtained which was slurried in toluene and evaporated to remove water. This material was passed over a silica column eluting with ethyl acetate to provide 7.13 g of solid product.

m.p.=66.5°–68° C.

ms (fd)=89 M+

Analysis for $C_3H_7NO_2$: Theory: C, 40.44; H, 7.92; N, 15.72; Found: C, 40.36; H, 7.75; N, 15.54.

C. Preparation of N-ethyl-2-hydroxyacetamide

The procedure of 84A was followed with ethylamine (100 ml, 70 weight percent in water) as the amine to provide 11.26 g of an oil. This material was passed over a silica column eluting with ethyl acetate. 7.2 g of product was recovered as white crystals.

m.p.=79°–82° C.

ms (fd)=103 M+

Analysis for $C_4H_9NO_2$: Theory: C, 46.59; H, 8.80; N, 13.58; Found: C, 46.86; H, 8.41; N, 14.00.

D. Preparation of 2-hydroxyacetamide

The procedure of 84A was followed using ammonium hydroxide (100 ml, 28% in H$_2$O) to provide 10.3 g of crystalline material. This material was recrystallized from ethyl acetate/ethanol (v:v, 4:1) to provide 6.0 g of white crystal product.

m.p.=111°–112.5° C.

ms (fd)=75 M+

Analysis for $C_2H_5NO_2$: Theory: C, 32.00; H, 6.71; N, 18.66; Found: C, 32.02; H, 6.49; N, 18.43.

E. Preparation of N-benzyl-2-hydroxyacetamide

The procedure of 84A was followed with methyl2-hydroxyethanoate (8 g) and benzylamine (10 ml in 30 ml H$_2$O). After one hour material precipitated out of solution. The mixture was stirred overnight, and the solid recovered by filtration to provide 4.12 g of white solid. The solvent was removed from the filtrate by vacuum to provide 4.71 g of material The solid and filtrate were combined and passed over a silica column eluting with a gradient of ethyl acetate to ethyl acetate/methanol (v:v, 1:1). Removal of solvent provided 8 g of white crystal product.

m.p.=101°–102° C.

ms (fd)=165 M+

I.R.=1634.88 cm$^{-1}$ (carbonyl)

Analysis for $C_9H_{11}NO_2$: Theory: C, 65.44; H, 6.71; N, 8.48; Found: C, 65.39; H, 6.83; N, 8.62.

In Examples 85 through 95, X represents Z-NHCH$_2$C(O)- where Z is as set forth for Example 73.

EXAMPLE 85

Preparation of X-OCH$_2$C(O)OCH$_3$

The carboxylic acid X-OH prepared as in Example 44 (1.5 g), methyl glycolate (315 mg), Hobt (473 mg) and dry DMF (125 ml) were combined and DCC (721 mg) was then added. The mixture was stirred at room temperature under nitrogen for 24 hours. The mixture was filtered and evaporated under vacuum to dryness. The residue was dissolved in ethyl acetate which was washed once with water, dried over K$_2$CO$_3$ and evaporated under vacuum to provide 1.86 g of an orange semi-solid material. This material was subjected to column chromatography eluting with a gradient of hexane/ethyl acetate (v:v, 9:1) to ethyl acetate. Removal of the solid provided 1.41 g of an orange material which was then passed over a chromatron using 4000 micron plate and eluting with hexane/ethyl acetate (1:1) to provide 980 mg of material.

ms (fd)=497 M+

This material was converted to the HCl salt and dried to provide 770 mg of tan solid.

m.p.=98°–104° C.

Analysis for $C_{28}H_{36}N_2O_6 \cdot HCl$: Theory: C, 63.09; H, 7.00; N, 5.26; Found: C, 62.81; H, 7.08; N, 4.97.

EXAMPLE 86

Preparation of X-O(CH$_2$)$_4$CH$_3$

The carboxylic acid X-OH prepared as in Example 44 (500 mg), amyl alcohol (20 ml) and amyl alcohol saturated with gaseous HCl gas (20 ml) were combined and refluxed under nitrogen for 1.5 hours. The mixture was then evaporated to dryness and the residue partitioned between ethyl acetate and water. The pH of the water layer was adjusted to 9.8 with 1N NaOH. The layers were separated and the ethyl acetate layer washed one time with water, dried over $K_2CO_3$ and evaporated to provide 660 mg of a viscous oil. This material was subjected to column chromatography eluting with a gradient of hexane/ethyl acetate (v:v, 9:1) to hexane/ethyl acetate (v:v, 1:1). Removal of solvent provided 400 mg of a white foam.

ms (fd)=494 M+, 495 M++1

This material was converted to the HCl salt and dried to provide 300 mg of white solid.

m.p.=75°-81° C.

Analysis for $C_{30}H_{42}N_2O_4 \cdot HCl$: Theory: C, 66.71; H, 8.21; N, 5.19; Found: C, 66.44; H, 8.07; N, 5.35.

EXAMPLE 87

Preparation of X-O-CH$_2$C(O)NH$_2$

The procedure of Example 85 was followed with X-OH prepared as in Example 44 (500 mg), 2-hydroxyacetamide (90 mg), Hobt (162 mg), dry DMF (50 ml) and DCC (247 mg) to provide 660 mg of an orange oil. This material was passed over a silica column eluting with ethyl acetate providing 310 mg of a white foam. This material was passed over a chromatron using 2000 micron plate and eluting with ethyl acetate to provide 260 mg of product.

ms (fd)=482.4 M++1

This was converted to the HCl salt and dried to provide a white solid.

m.p.=111°-116° C.

Analysis for: $C_{27}H_{35}N_3O_5 \cdot HCl$: Theory: C, 62.60; H, 7.00; N, 8.11; Found: C, 62.61; H, 6.97; N, 7.71.

EXAMPLE 88

Preparation of X-OCH$_2$C(O)NHCH$_3$

The procedure of Example 85 was followed with X-OH prepared as in Example 44 (500 mg), N-methyl-2-hydroxyacetamide (107 mg), Hobt (162 mg), DMF (500 ml), and DCC (247 mg) to provide 890 mg of an oil. This material was passed over a silica column eluting with ethyl acetate with 400 mg of material recovered. This was passed over a chromatron using 2000 micron plate and eluting with ethyl acetate to provide 260 mg of a white solid.

ms (fd)=497 M++1

This material was converted to the HCl salt and dried to provide 218 m9 of a tan solid.

m.p.=114°-118° C.

Analysis for $C_{28}H_{37}N_3O_5 \cdot HCl$: Theory: C, 63.21; H, 7.20; N, 7.90; Found C, 62.90; H, 7.15; N, 7.50.

EXAMPLE 89

Preparation of X-OCH$_2$C(O)NHCH$_2$CH$_3$

The procedure of Example 85 was followed with X-OH prepared as in Example 44 (530 mg), N-ethyl-2-hydroxyacetamide (134 mg), Hobt (176 mg), dry DMF (50 ml), and DCC (268 mg) to provide 810 mg of a viscus oil. This was passed over a silica column eluting with ethyl acetate with 400 mg of a white foam recovered. This was passed over a chromatron with a 2000 micron plate eluting with ethyl aceate to provide 300 mg of product.

ms (fd)=510 M++1

This material was converted to the HCl salt and dried at 60° C. to provide a white solid.

m.p.=109°-113° C.

Analysis for $C_{29}H_{39}N_3O_5 \cdot HCl$: Theory: C, 63.78; H, 7.38; N, 7.69; Found: C, 63.38; H, 7.32; N, 7.47.

EXAMPLE 90

Preparation of X-OCH$_2$C(O)N(CH$_3$)$_2$

The procedure of Example 85 was followed with X-OH prepared as in Example 44 (500 mg), N,N-dimethyl-2-hydroxyacetamide (124 mg), Hobt (162 mg), dry DMF (50 ml), and DCC (247 mg) to provide 615 mg of an orange semi-solid materia. This was passed over a silica column eluting with ethyl acetate to provide 260 mg of an orange foam. This was passed over a chromatron with a 2000 micro plate eluting with ethyl acetate to provide 230 mg of a white foam.

ms (fd)=509 M+, 510 M++1

This material was converted to the HCl salt and dried at 60° C. to yield 220 mgs of white solid.

m.p.=124°-130° C.

Analysis for $C_{29}H_{39}N_3O_5 \cdot HCl \cdot \frac{1}{2}H_2O$: Theory: C, 62.74; H, 7.38; N, 7.57; Found: C, 62.78; H, 7.53; N, 7.69.

EXAMPLE 91

Preparation of X-NHCH$_2$(C$_6$H$_{11}$)

The procedure of Example 85 was followed with X-OH prepared as in Example 44 (500 mg), N-cyclohexylmethylene-2-hydroxyacetamide (205 mg), Hobt (162 mg), dry DMF (40 ml), and DCC (247 mg) to provide 715 mg of pale orange foam. This material was passed over a silica column eluting with ethyl acetate to provide 600 mg of material which was then passed over a chromatron using a 2000 micron plate eluting with ethyl acetate to provide 170 mg of product.

ms (fd)=519 M+, 520 M++1

This material was converted to HCl salt and dried at 60° C. for two hours to provide a white solid.

m.p.=136°-140° C.

Analysis for $C_{32}H_{45}N_3O_3 \cdot HCl$: Theory: C, 69.11; H, 8.34; N, 7.56; Found C, 68.83; H, 8.38; N, 7.81.

EXAMPLE 92

Preparation of X-O-(4-methoxycyclohexyl)--hydrochloride.

X-OH prepared as in Example 44 (424 mg), $K_2CO_3$ (1.83 g), CIS-4-methoxycylohexyl-p-toluensulfonate (1.52 g) were combined in dry DMF (70 ml) and the mixture heated under nitrogen for 20h at reflux. The mixture was cooled, filtered, and evaporated under vacuum to yield 640 mgs. This material was subjected to column chromatography eluting with a gradient of hexane/ethyl acetate (v:v, 1:1) to ethyl acetate. Removal of the solvent provided 370 mg of a viscous oil.

ms (fd)=537 M++1 This material was converted to the HCl salt and dried at 60° C. to provide 300 mg of a white solid.

m.p.=116°-119° C.

Analysis for $C_{32}H_{44}N_2O_5 \cdot HCl$: Theory: C, 67.06; H, 7.91; N, 4.89; Found: C, 66.80; H, 7.82; N, 4.87.

EXAMPLE 93

Preparation of X-OCH₂C(O)NHCH₂(C₆H₅)·hydrochloride·monohydrate

X-OH prepared as in Example 44 (500 mg), N-benzyl-2-hydroxyacetamide (198 mg), Hobt (162 mg), dry DMF (40 ml) and DCC (247 mg) were combined as in Example 85 to provide 910 mg of a tan oil. This material was passed over a silica column eluting with ethyl acetate with 415 mg of an orange foam recovered. This material was passed over a chromatron using a 2000 micron plate and eluting with ethyl acetate to provide 160 mg of material.

ms (fd)=571 M+, 572 M++1

This material was converted to HCl salt and dried at 60° to yield a white solid.

m.p.=115°-120° C.

Analysis for C₃₄H₄₁N₃O₅·HCl H₂O: Theory: C, 65.21; H, 7.0B; N, 6.71; Found: C, 65.23; H, 7.29; N, 6.71.

EXAMPLE 94

Preparation of X-OCH(CH₃)OC(O)CH₃·hydrochloride

XOH prepared as in Example 44 (463 mg) and K₂CO₃ (1.83 g) were heated at 70° C. for ten minutes. The mixture was then cooled to room temperature and 1-bromoethylacetate (894 mg) in DMF (20 ml) was added dropwise at room temperature. After stirring one hour at room temperature, the solution was filtered and evaporated. The residue was partitioned between ethyl acetate and water with the water layer pH adjusted to 9.8 with 1N N₃OH. The layers were separated and the ethyl acetate layer washed one time with water, dried over K₂CO₃ and evaporated to provide 620 mg of a dark oil. This material was passed over a silica column eluting with a gradient of hexane/ethyl acetate (v:v, 1:1) to ethyl acetate. Removal of solvent provided 330 mg of a dark oil which was placed over the chromatron using a 2 mm plate and eluting with a gradient of hexane/ethyl acetate (v:v, 1:1) to ethyl acetate. The resulting solution was stirred over decolorizing charcoal and the solvent removed to provide 200 mg of a tan oil having a mass spec of 511 (M++1). This product was converted to HCl salt and dried at 60° C. to provide 190 mg of a tan solid.

m.p.=94°-98° C. (with decomposition)

Analysis for C₂₉H₃₈N₂O₆·HCl: Theory: C, 63.67; H, 7.19; N, 5.12 ; Found: C, 63.65; H, 7.32; N, 5.15.

EXAMPLE 95

Preparation of

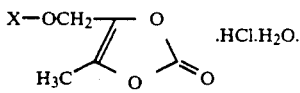

XOH prepared as in Example 44 (636 mg) and K₂CO₃ (1.89 g) were combined and cooled to 0° C. under a nitrogen atmosphere. 4',Bromomethyl-4,5-methyl-1,3-dioxol-2-one (1.07 g) in dry methylene chloride (20 ml) was added dropwise. The mixture was allowed to warm to room temperature and stirred for one hour. The mixture was filtered and evaporated to dryness to provide 1.0 g of a dark oil. This was subjected to column chromatography eluting with a gradient of hexane/ethyl acetate (1:1) to ethyl acetate/methanol (v:v, 9:1). The removal of solvent provided 300 mg of a tan oil.

ms (fd)=537 M++1

A portion of this product was converted to HCl salt and dried at 60° C. to provide a white solid.

m.p.=72°-75° C.

Analysis for C₃₀H₃₆N₂O₇·HCl·H₂O: Theory: C, 60.95; H, 6.65; N, 4.74; Found: C, 60.84; H, 6.47; N, 4.82.

EXAMPLE 96

Preparation of sec-butyl-2-aminoaceate-para-tosylate

Glycine (7.51 g), paratoluenesulfonic acid (20.92 g), isobutyanol (20 ml) and toluene (200 ml) were combined and refluxed for five hours with a Dean Stark trap. The reaction mixture was cooled and evaporated to dryness to provide 28.11 g of crystalline product. The crystalline product was recrystallized from hexane/ethyl acetate (v:v, 4:1) to provide 27.12 g of white crystals.

m.p.=73°-74° C.

ms (fd)=132 (free base)=M+

I.R.=1738.9 cm⁻¹ (carbonyl)

Analysis for C₆H₁₃N₂O·p-tosylate Theory: C, 51.47; H, 6.98; N, 4.62; Found: C, 51.56; H, 6.96; N, 4.59.

EXAMPLE 97

Preparation of (+)(3R,4R)-trans-[[2-[[4-(3-hydroxyphenyl)-3,4-dimethyl-1-piperidinyl]methyl]-1-oxo-3-phenylpropyl]amino]acetic acid monohydrate [(+)X-OH·H₂O of Example 85].

A. Preparation of (+)-trans-(3R,4R)-3-[4-(3-hydroxyphenyl)-3,4-dimethyl-1-piperidinyl]-2-phenylmethylpropanoic acid, ethyl ester.

The procedure of Example 4A was followed with (+)-trans-(3R,4R)-4-(3-hydroxyphenyl)-3,4-dimethylpiperidine (4.4 g, 20 mmole) and 2-ethoxycarbonyl-3-phenylpropene (4.5 g) in methanol (225 ml). The reactants were stirred at room temperature under nitrogen for ten days with the reaction mixture then evaporated to dryness to provide 8.8 g of a viscous oil. This material was passed through a Prep-500 liquid chromatography eluting with a gradient of hexane to 10% ethyl acetate/hexane. 8.0 g of a white foam was recovered.

ms (fd)=395 M+

B. Preparation of (+)-trans-(3R,4R)-3-[4-(3-hydroxyphenyl)-3,4-dimethyl-1-piperidinyl-2-phenylmethyl propanoic acid[(+)-Z-OH]

The product from 97A above (6 g, 15 mmole) and lithium hydroxide (1.89 g) were combined in a mixture of THF/methanol/water (192 ml/64 ml/64 ml) and stirred at room temperature for three hours. The mixture was then poured into 1N HCl and stirred for five minutes. The aqueous solution was then adjusted to a pH of 9.8 with triethylamine and extracted with n-butanol/tolune (3:1). The organic layer was dried over MgSO₄ and evaporated to provide 7.14 g of a white foam. This material was subjected to column chromatography eluting with a gradient of ethyl acetate/methanol (9:1) to ethyl acetate/methanol (1:1). Removal of solvent provided 3.98 g of a white powder.

ms (fd)=367 M+, 368 M++1

C. Preparation of (+)X-OCH₂CH(CH₃)₂

The carboxylic acid product (+)Z-OH from 97B above (2.45 g, 6.7 mmole), the amine from Example 96 (1.82 g), triethylamine (604 mg), Hobt (806 mg), DCC (1.23 g) were combined in dry DMF (180 ml) and stirred at room temperature under nitrogen for 72 hours. The mixture was then filtered and evaporated to dryness. The residue was partitioned between ethyl acetate and water. The pH of the water layer was adjusted to 9.8 with 1N N₃OH and the layers were separated. The organic layer was dried over $K_2CO_3$ and then evaporated to provide 3.21 g of an orange foam. This material was passed over a silica column eluting with a gradient of hexane/ethyl acetate (9:1) to ethyl acetate. The removal of solvent provided 2.31 g of a white foam.

ms (fd)=481 M+

D. Separation of diastereomers 4.36 g of an isomeric mix prepared as in Example 97C above was passed over a Prep-500 liquid chromatograph using a gradient of hexane/triethylamine (99:1) to hexane/ethyl acetate/triethylamine (75:24:1). An 8 liter forerun was discarded and 300 ml fractions were then collected.

Fractions 38-45 contained 99% of a first peak by HPLC. Removal of solvent provided 580 mg of a white foam (Diastereomer A)[(+)-(3R,4R)-X-OCH₂CH(CH₃)₂. ms (fd)=481 M+

$[\alpha]_{365} = +172.65°$

Analysis for $C_{29}H_{40}N_2O_4$: Theory: C, 72.47; H, 8.39; N, 5.83; Found: C, 72.49; H, 8.59; N, 5.63.

This was converted to the HCl salt.

m.p.=91°-95° C.

Analysis for: Theory: C, 67.36; H, 7.99; N, 5.42; Found: C, 67.06; H, 7.98; N, 5.30.

Fractions 57-67 were analyzed to contain 85% of a second peak by HPLC. Removal of solvent provided 490 mg of a solid material. Recrystallization from isopropyl ether provided 410 mg of crystalline product (diastereomer B).

m.p.=136°-136.5° C.

ms (fd)=481 M+

$[\alpha]_{365} = +153.03°$

Analysis for: $C_{29}H_{40}N_2O_4$: Theory: C, 72.47; H, 8.39; N, 5.83; Found: C, 72.42; H, 8.26; N, 6.04.

E. Formation of Title Compound [(+)X-OH]

Diastereomer A prepared as in Example 97D above (300 mg), dioxane (15 ml) and 6N HCl (15 ml) were combined and refluxed for six hours. The mixture was cooled to room temperature and evaporated to dryness. The resulting solid was partitioned between water and butanol/toluene (3:1). The water layer was adjusted to a pH of 9.8 using triethylamine. The layers were separated and the organic layer dried over $MgSO_4$ and evaporated to dryness. The solid material was passed over a silica column eluting with a gradient of ethyl acetate/methanol (9:1) to methanol. Evaporation of solvent yielded 126 mgs of a white solid.

m.p.=135°-138° C.

ms (fd)'424 M+, 425 M++1

Analysis for $C_{25}H_{32}N_2O_4 \cdot H_2O$: Theory: C, 67.87; H, 7.74; N, 6.32; Found : C, 67.49; H, 7.45; N, 5.97.

EXAMPLE 98

Preparation of (—)-(3S,4S)-trans-[[2-[[4-(3-hydroxyphenyl)-3,4-dimethyl)-1-piperidinyl]methyl]-1-oxo-3-phenylpropyl]amino]acetic acid [(—)X-OH of Example 85]

A. Preparation of (—)-trans-(3S,4S)-3-[4-(3-hydroxyphenyl)-3,4-dimethyl-1-piperidinyl]-2-phenylmethyl-propanoic acid ethyl ester.

The procedure of Example 97A was followed using (—)-trans (3S,4S)-4-(3-hydroxyphenyl)-3,4-dimethyl-piperidine (10 g, 48 mmole) and 2-ethoxycarbonyl-3-phenylpropene (10.2 g) in methanol (500 ml). 18.31 g of a tan viscus oil was recovered. This was passed over a PREP-500 liquid chromatograph eluting with a gradient of hexane to 10% ethyl acetate/hexane to providing 17.40 g of a white foam.

ms (fd)=395 M+

B. Preparation of (—)-(3S,4S)-3-[4-(3-hydroxyphenyl)-3,4-dimethyl-1-piperidinyl]-2-phenylmethyl-propanoic acid.

The procedure of Example 97B was followed with the product from Example 97A (12.5 g, 32 mmole), lithium hydroxide (3.98 g) in THF/methanol/water (400 ml/130 ml/130 ml). 10.75 g of a tan foam was recovered. This was subjected to column chromatography eluting with a gradient of ethyl acetate/methanol (9:1) to ethyl acetate/methanol (1:1). Removal of the solvent provided 8.97 g of a white powder.

ms (fd)=368 M++1

C. Preparation of (—)-X-OCH₂-CH(CH₃)₂

The procedure of Example 97C was followed with the product from Example 98B (5.12 g, 14 mmole), amine from Example 96 (4.54 g), triethylamine (1.5 g), Hobt (2.0 g) DCC (3.04 g) in dry DMF (400 ml). 7.81 g of an orange foam was recovered. This was passed over a silica column eluting with a gradient of hexane/ethyl acetate (9:1) to hexane/ethyl acetate (1:1). Removal of the solvent provided 5.5 g of a white foam.

ms (fd)=481 M+

D. Separation of Diastereomers

The procedure of Example 97D was followed using 4.20 g of the (—)-isomeric mix of Example 98C.

Fractions 33-40 showed 98% of a first peak by HPLC. Removal of solvent provided 435 mg of a white foam (diastereomer A).

ms (fd)=481 M+

$[\alpha]_{365} = -172.11°$

Analysis for $C_{29}H_{40}N_2O_4$: Theory: C, 72.47; H, 8.39; N, 5.83; Found C, 72.31; H, 8.51; N, 5.66.

Fractions 54-63 showed 88% of a second peak by HPLC. Removal of solid provided 510 mg of material. This was recrystallized from isopropyl ether to provide 460 mg of a crystalline product. HPLC showed 99% of this second peak (diastereomer B).

ms (fd)=481 M+

$[\alpha]_{365} = -153.95°$

Analysis for $C_{29}H_{40}N_2O_4$: Theory: C, 72.47; H, 8.39; N, 5.83; Found C, 72.67; H, 8.35; N, 5.88.

E. Preparation of (—)X-OH

The procedure of Example 97E was followed with Diastereomer B from Example 98D (200 mg), dioxane (10 ml) and 6N HCl (10 ml) to provide 210 mg of material. This was passed over a silica column eluting with a gradient of ethyl acetate/methanol (9:1) to methanol Removal of the solvent provided 101 mg of product.
m.p. = 130°-133° C.
ms (fd) = 421 M+ + 1
[α]365 (−115.16°)
Analysis for $C_{25}H_{32}N_2O_4 \cdot H_2O$ Theory C 67.87 H 7.7N 6.32; Found C 68.07 H 7.34 N 6.15.

The instant compounds are useful in blocking peripherial opioid receptors and preventing peripherally opiate induced side effects These side effects induced by the administration of an opiate such as morphine to a mammal can include constipation, nausea, and vomiting. These compounds can also be useful in the treatment of irritable bowel syndrome and idiopathic constipation. While not wishing to be bound by the theory, it is believed that the instant compounds act as opioid antagonists and bind to peripherial opioid receptors outside of the brain. The compounds do not substantially pass through the blood-brain barrier and therefore do not mitigate the opioid's effect on central (brain and spinal cord) opioid receptors. Consequently, these compounds should also be substantially free of other centrally mediated effects.

In order to determine in vivo opioid receptor antagonism, the mouse writhing analgesis test was used. Test compounds were measured for their ability to block morphine-induced analgesia.

Five CF-1 male mice (Charles River, Portage, Mich.), weighing approximately 20 g after being fasted overnight, were observed simultaneously for the writhing response. The writhing response was defined as a contraction of the abdominal musculature, followed by the extension of the hind limbs, and was induced by the intraperitoneal adminstration of 0.6% acetic acid in a volumne of 1 ml/100 g body weight. The observation period was 10 min. in duration, beginning 5 min. after injection of acetic acid. The percent inhibition of writhing was calculated from the average number of writhes in the control (non-drug) group. Each data point is the mean (±standard error) for five mice. The $ED_{50}$ was defined as the dose of agonist that inhibited mean writhing by 50%. The $AD_{50}$ was defined as the dose of antagonist that reduced the inhibition of writhing produced by a 1.25 mg/kg dose of morphine sulfate to 50%. Each mouse was only used once. All drugs were administered subcutaneously (1 ml/100 g bwt) 20 min. before the injection of acetic acid.

Determinations of peripheral opioid activity were conducted. Mice maintained (6 mice/cage) on 0.01M saccharin water with 1 g/l morphine sulfate for a minimum of 10 days with mice averaging 3.0+ g water/mouse/day for at least three days are used as subjects. The morphine water was removed 45 min. prior to injection with the proposed opioid antagonist. Initial testing consisted of 5 mice/dose of compound. The antagonist was given by the subcutaneous or oral, route of administration, and the mice were placed in 11-14"×4 7/12 I.D. clear plastic cylinders with white paper towels used for a floor.

The mice were then monitored visually for 30 minutes post-injection for the presence of jumping and of diarrhea. Jumping was scored as positive if at least one jump occurred in 30 min. Diarrhea was scored as positive when feces were moist enough to stain the white paper at the base of the cylinder. After 30 minutes of testing, the mice were placed back in original cages, put back on morphine water, and not tested again for 48 hrs. Lower doses of the antagonist compounds were tested until threshold doses for diarrhea were determined. Diarrhea is a peripherally mediated sign of precipitated opiate abstinence.

The extent of the effect on peripheral activity compared to central activity of the present compounds can be determined by comparing the $AD_{50}$ for the mouse writhing test with the $ED_{50}$ for the mouse diarrhea test. The higher the ratio, the greater the relative antagonism of the peripheral opioid receptors by a particular compound. This ratio for each compound is provided in Table I.

TABLE I

| Example No.[1] | $AD_{50}$[2] | $ED_{50}$[3] | Ratio[4] |
|---|---|---|---|
| 4A | 1.08 | 0.012 | 9 |
| 4B | 8.90 | 0.011 | 809 |
| 5A | 1.2 | 0.06 | 20 |
| 5B | 1.6 | 0.24 | 7 |
| 8A | 0.70 | 0.02 | 35 |
| 8B | 0.64 | 0.012 | 53 |
| 9B | 1.50 | 0.02 | 75 |
| 10 | 0.54 | 0.06 | 9 |
| 11 | 2.4 | 0.017 | 141 |
| 12 | 40 | 0.015 | 2667 |
| 13 | >40 | 0.32 | >125 |
| 14 | >40 | 0.92 | >43 |
| 15 | >40 | 0.30 | >133 |
| 17 | >40 | 0.06 | >667 |
| 18 | >40 | 0.045 | >888 |
| 20 | 32.1 | 0.004 | 802 |
| 21 | >20 | 0.16 | >125 |
| 22 | >40 | 0.08 | >500 |
| 23 | >20 | 0.14 | >140 |
| 24 | >40 | 0.10 | >400 |
| 25 | 11.5 | 0.29 | 40 |
| 26 | 7.5 | 0.03 | 250 |
| 27 | 15.3 | 0.30 | 51 |
| 28 | >40 | 0.01 | >4000 |
| 29 | 3.9 | 0.17 | 23 |
| 30 | >40 | 0.017 | >2353 |
| 31 | 5.3 | 0.14 | 38 |
| 32 | 7.3 | 0.16 | 45 |
| 33 | 10.2 | 0.17 | 60 |
| 34 | 15.1 | 0.18 | 84 |
| 35 | 40 | 0.06 | 667 |
| 36 | 3.8 | 0.32 | 12 |
| 37 | 3.9 | 0.09 | 43 |
| 38 | >40 | 0.06 | >667 |
| 39 | 11.9 | 0.66 | 18 |
| 40 | 4.5 | 1.30 | 3.5 |
| 41 | 4.5 | 0.17 | 26 |
| 42 | 2.1 | 0.26 | 8 |
| 43 | 1.9 | 0.013 | 146 |
| 44 | >40 | 0.15 | >266 |
| 45 | 2.6 | 0.24 | 11 |
| 46 | 40 | 0.07 | 571 |
| 47 | 40 | 0.15 | 267 |
| 48 | >40 | 0.10 | >400 |
| 49 | 6.08 | 0.10 | 61 |
| 50 | 14.3 | 0.54 | 26 |
| 51 | 3.8 | 0.15 | 25 |
| 52 | 8 | 0.20 | 40 |
| 53 | >40 | 1.70 | >23 |
| 54 | 23 | 0.02 | 1150 |
| 55 | 7.5 | 0.12 | 63 |
| 56 | 40 | 0.06 | 667 |
| 57 | >40 | 0.10 | >400 |
| 59 | 5.9 | 0.54 | 11 |
| 60 | 11.2 | 0.10 | 112 |
| 61 | 3.3 | 0.05 | 66 |
| 62 | 18.3 | 0.15 | 122 |
| 63 | 26 | 0.29 | 90 |
| 64 | >40 | 0.90 | >45 |
| 65 | 2.8 | 0.92 | 3 |
| 66 | 14.0 | <3.0 | <4.7 |
| 67 | 5.5 | 0.15 | 36 |
| 68 | >40 | 0.23 | >174 |
| 69 | 30 | 1.70 | 51 |
| 71 | 2.1 | 0.19 | 11 |
| 73 | 20 | 1.73 | 11 |
| 75 | 5.2 | 0.073 | 71 |

TABLE I-continued

| Example No.[1] | AD$_{50}$[2] | ED$_{50}$[3] | Ratio[4] |
|---|---|---|---|
| 77 | >40 | 1.31 | >31 |
| 78B | 1.6 | 0.055 | 29 |
| 79 | 1.7 | 0.13 | 13 |
| 80 | 3.9 | 0.16 | 24 |
| 81 | 13.2 | 3.28 | 4 |
| 82 | .95 | 0.055 | 17 |
| 83 | 0.71 | 0.04 | 2 |
| 85 | 9.5 | 0.05 | 190 |
| 86 | >40 | 0.017 | >2353 |
| 87 | 19 | 0.71 | 27 |
| 88 | 13.5 | 0.07 | 193 |
| 89 | 6.0 | >10 | <1 |
| 90 | 2.2 | 0.1 | 22 |
| 91 | 4.0 | 0.5 | 8 |
| 92 | 7.7 | .005 | 1540 |
| 93 | 29.0 | .008 | 3625 |
| 94 | 20 | .009 | 2222 |
| 95 | 2.7 | 0.19 | 14 |
| 97D* | 12.7 | 0.04 | 317 |
| 97D** | 32 | 0.6 | 53 |
| 97E | 8.9*** | 0.07*** | 127 |
| 98D* | 2.9 | 0.76 | 4 |
| 98D** | 15.3 | 0.06 | 255 |
| 98E | 6.2*** | 0.10*** | 62 |

The compounds of the present invention have been found to display excellent activity in an opioid receptor binding assay which measures the affinity of the compounds to to bind to mu receptors. This assay was conducted by the following procedure.

Male Sprague Dawley rats for mu site experiments were sacrificed via decapitation and the brains were removed. The brain tissue, rat whole brain minus cerebellum for mu was homogenized in a Teflon and glass tissue homogenizer. A supernatant I, pellet IV, fraction was frozen in a nitrogen freezer at 1.33 g/ml concentration and stored for not longer than five weeks prior to use. Pellets were rehydrated with physiological buffer prior to use.

For mu sites increasing concentrations of experimental compound, [0.1 to 1000 nanomolar (nM)], Kreb-Hepes buffer pH 7.4, and tritiated naloxone (0.5 nM) ($^3$H ligand) were combined in polystyrene tubes at room temperature. The reaction was initiated by the addition of the resuspended tissue which had been preincubated at 37° C. for 20 minutes. The reaction mixture was incubated in a 37° C. water bath for 20 minutes. The reaction was terminated by rapid filtration, (Brandel Cell Harvestor), through Whatman GF/B glass filters that had been presoaked in Krebs-Hepes buffer pH 7.4. The filters were then washed 2x with 5 ml of ice cold Krebs-Hepes buffer pH 7.4. Washed filters were placed in scintillation vials and 10 ml RedySolv, (Brandel), was added and samples counted in a Searle D-300 beta counter. Means and standard error statistics were calculated for triplicate experimental determinations in certain cases. The incubation time for the reaction mixture was 20 minutes at 37° C.

Ki values were calculated using a minitab statistical program according to the following formula:

$$K_i = \frac{IC_{50}}{1 + \frac{\text{concentration of }^3H\text{ ligand}}{K_D}}$$

wherein IC$_{50}$ is the concentration at which 50% of the $^3$H ligand is displaced by the test compounds and K$_D$ is the dissociation constant for the $^3$H ligand at the receptor site. K$_D$ can be determined as described by Bennett, "Methods in Binding Studies", *Neurotransmitter Receptor Binding*, Yamamura, et al., ed., p. 57-90, Raven Press, N.Y. (1978) incorporated herein by reference.

The results of the evaluation of certain compounds of the present invention in the opioid receptor binding assay are set forth below in Table II. In the Table, column 1 sets forth the Example Number of the compound evaluated, column 2 the Ki value in nanomolar (nM) at the mu receptor and columns 3 and 4 the percent displacement by the test compound at the indicated concentration, i.e., 10 nm or 100 nm.

TABLE II

| | [$^3$H] NAL Binding Assay (mu receptor) | | |
|---|---|---|---|
| Example | Ki[1] | 10 nM[2] | 100 nM[2] |
| 4A | 1.38 | 92 | 98 |
| 4B | 2.62 | 83 | 97 |
| 5A | 13.80 | 61 | 93 |
| 5B | 1.11 | 93 | 99 |
| 8A | 2.01 | 88 | 95 |
| 8B | 0.27 | 100 | 100 |
| 9B | 0.66 | 90 | 93 |
| 10 | 1.17 | 89 | 100 |
| 11 | 0.30 | 81 | 89 |
| 12 | 1.89 | 84 | 94 |
| 13 | 0.43 | 94 | 95 |
| 14 | 6.42 | 87 | 93 |
| 15 | 1.07 | 99 | 100 |
| 17 | 0.43 | 97 | 100 |
| 18 | 0.43 | 97 | 97 |
| 20 | 0.78 | 98 | 100 |
| 21 | 0.45 | 96 | 100 |
| 22 | 0.33 | 100 | 96 |
| 23 | 1.65 | 100 | 96 |
| 24 | 0.45 | 100 | 100 |
| 25 | 0.22 | 100 | 100 |
| 26 | 1.17 | 76 | 91 |
| 27 | 0.91 | 92 | 99 |
| 28 | 3.09 | 86 | 95 |
| 29 | 2.94 | 98 | 100 |
| 30 | 0.42 | 89 | 93 |
| 31 | 0.40 | 100 | 97 |
| 32 | 0.72 | 97 | 100 |
| 33 | 1.19 | 95 | 100 |
| 34 | 36.60 | 78 | 97 |
| 35 | 0.54 | 98 | 100 |
| 36 | 0.47 | 79 | 86 |
| 37 | 1.09 | 93 | 97 |
| 38 | 0.48 | 98 | 99 |
| 39 | 3.75 | 91 | 98 |
| 40 | 0.75 | 95 | 100 |
| 41 | 0.39 | 100 | 100 |
| 42 | 0.57 | 100 | 97 |
| 43 | 0.64 | 98 | 99 |
| 44 | 0.89 | 87 | 94 |
| 45 | 1.28 | 93 | 98 |
| 46 | 0.31 | 99 | 95 |
| 47 | 2.11 | 89 | 95 |
| 48 | 1.82 | 96 | 100 |
| 49 | 0.54 | 98 | 100 |
| 50 | 1.20 | 94 | 100 |
| 51 | 5.43 | 85 | 97 |
| 52 | — | 53 | 92 |
| 53 | — | 2 | 11 |
| 54 | 2.27 | 78 | 98 |
| 55 | — | 83 | 97 |
| 56 | 0.49 | 97 | 98 |
| 57 | 0.50 | 92 | 98 |
| 59 | 4.64 | 88 | 100 |
| 60 | 1.89 | 100 | 100 |
| 61 | 1.91 | 98 | 99 |
| 62 | 1.18 | 89 | 98 |
| 63 | 2.00 | 89 | 100 |
| 64 | 1.23 | 94 | 100 |
| 65 | — | 57 | 95 |
| 66 | 1.96 | 70 | 85 |
| 67 | 0.37 | 79 | 91 |
| 68 | 1.51 | 79 | 86 |
| 69 | — | 57 | 89 |
| 71 | 0.71 | 81 | 94 |

TABLE II-continued

| | [³H] NAL Binding Assay (mu receptor) | | |
|---|---|---|---|
| Example | $K_i^{(1)}$ | 10 nM$^{(2)}$ | 100 nM $^{(2)}$ |
| 73 | 1.80 | 84 | 90 |
| 75 | 1.15 | 90 | 99 |
| 77 | 1.35 | 88 | 95 |
| 78B | — | 0 | 2 |
| 79 | — | 0 | 15 |
| 80 | — | 0 | 37 |
| 81 | — | 21 | 55 |
| 82 | — | 31 | 73 |
| 83 | — | 52 | 83 |
| 85 | — | 93 | 98 |
| 86 | — | 74 | 91 |
| 87 | — | 94 | 99 |
| 88 | — | 93 | 99 |
| 89 | — | 94 | 99 |
| 90 | — | 93 | 99 |
| 91 | — | 69 | 94 |
| 92 | — | 85 | 97 |
| 93 | — | 81 | 95 |
| 94 | — | 76 | 95 |
| 95 | — | 79 | 94 |
| 97D | — | 86 | 99 |
| 97E | — | 80 | 90 |
| 98D | — | 57 | 92 |
| 98E | — | 69 | 87 |
| 97D | — | 11 | 70 |
| 98D | — | 80 | 96 |

$^{(1)}$In nanomoles
$^{(2)}$% displacement

While it is possible to administer a compound of the invention directly without any formulation, the compounds are preferably employed in the form of a pharmaceutical formulation comprising a pharmaceutically acceptable excipient and at least one compound of the invention. Such compositions contain from about 0.1 percent by weight to about 90.0 percent by weight of a present compound As such, the present invention also provides pharmaceutical formulations comprising a compound of the invention and a pharmaceutically acceptable excipient therefor.

In making the compositions of the present invention, the active ingredient is usually mixed an excipient which can be a carrier, or a diluent or be diluted by a carrier, or enclosed within a carrier which can be in the form of a capsule, sachet, paper or other container. When the carrier serves as a diluent, it can be a solid, semi-solid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

Examples of suitable excipients, include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can also include wetting agents, emulsifying and suspending agents, preserving agents, sweetening agents or flavoring agents. The formulations of the invention can be formulated so as to provide quick, sustained, or delayed release of the active ingredient after administration to the patient by employing procedures well known in the art.

For oral administration, a compound of this invention is preferably admixed with one or more excipient, and molded into tablets or enclosed in gelatin capsules.

The compositions are preferably formulated in a unit dosage form, each dosage containing from about 1 to about 500 mg more usually about 5 to 300 mg of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

In order to more fully illustrate the operation of this invention, the following formulation examples are provided. The samples are illustrative only, and are not intended to limit the scope of the invention. The formulations may employ as active compounds any of the compounds of the present invention. Specific compounds are provided as illustrative with Z, G, X.

Formulation 1

Hard gelatin capsules are prepared using the following ingredients:

| | Amount Per Capsule | Concentration by Weight (percent) |
|---|---|---|
| Z-NH(CH$_2$)$_2$C(O)NH$_2$ | 20 mg | 10.0 |
| starch dried | 200 mg | 43.0 |
| magnesium stearate | 10 mg | 2.0 |
| | 460 mg | 100.0 |

The above ingredients are mixed and filled into hard gelatin capsules in 460 mg quantities.

Formulation 2

Capsules each containing 20 mg of medicament are made as follows:

| | Amount Per Capsule | Concentration by Weight (percent) |
|---|---|---|
| G-NH(CH$_2$)$_2$C(O)NH$_2$ | 20 mg | 10.0 |
| starch | 89 mg | 44.5 |
| microcrystalline cellulose | 89 mg | 44.5 |
| magnesium stearate | 2 mg | 1.0 |
| | 200 mg | 100.0 mg |

The active ingredient, cellulose, starch and magnesium stearate are blended, passed through a No. 45 mesh U.S. sieve and filled into a hard gelatin capsule.

Formulation 3

Capsules each containing 100 mg of active ingredient are made as follows:

| | Amount Per Capsule | Concentration by Weight (percent) |
|---|---|---|
| G-NH(CH$_2$)$_3$C(O)NHCH$_3$ | 100 mg | 30.0 |
| polyoxyethylene sorbitan monooleate | 50 microg | 0.02 |
| starch powder | 250 mg | 69.98 |
| | 350.05 mg | 100.00 |

The above ingredients are thoroughly mixed and placed in an empty gelatin capsule.

Formulation 4

Tablets each containing 10 mg of active ingredient are prepared as follows:

|  | Amount Per Tablet | Concentration by Weight (percent) |
|---|---|---|
| $X\text{-}OCH_2CH(CH_3)_2$ | 10 mg | 10.0 |
| starch | 45 mg | 45.0 |
| microcrystalline cellulose | 35 mg | 35.0 |
| polyvinylpyrrolidone (as 10% solution in water) | 4 mg | 4.0 |
| sodium carboxymethyl starch | 4.5 mg | 4.5 |
| magnesium stearate | 0.5 mg | 0.5 |
| talc | 1 mg | 1.0 |
|  | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°-60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

Formulation 5

A tablet formula may be prepared using the ingredients below:

|  | Amount Per Capsule | Concentration by Weight (percent) |
|---|---|---|
| $X\text{-}O(CH_2)_4CH_3$ | 250 mg | 38.0 |
| cellulose microcrystalline | 400 mg | 60.0 |
| silicon dioxide fumed | 10 mg | 1.5 |
| stearic acid | 5 mg | 0.5 |
|  | 665 mg | 100.0 |

The components are blended and compressed to form tablets each weighing 665 mg.

Formulation 6

Suspensions each containing 5 mg of medicament per 5 ml dose are made as follows:

|  | per 5 ml of suspension |
|---|---|
| $M\text{-}NHCH_2C(O)OH$ | 5 mg |
| sodium carboxymethyl cellulose | 50 mg |
| syrup | 1.25 ml |
| benzoic acid solution | 0.10 ml |
| flavor | q.v. |
| color | q.v. |
| water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

|  | Concentration by Weight (percent) |
|---|---|
| $U\text{-}NHCH_2C(O)OH$ | 0.25 |
| ethanol | 29.75 |
| Propellant 22 (chlorodifluoromethane) | 70.00 |
|  | 100.00 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

I claim:

1. A trans-3,4 isomer of a compound of the formula (I)

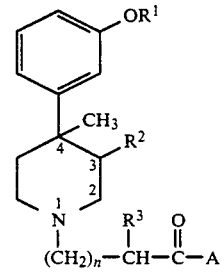

wherein $R^1$ is hydrogen or $C_1$-$C_5$ alkyl;

$R^2$ is hydrogen, $C_1$-$C_5$ alkyl or $C_2$-$C_6$ alkenyl;

$R^3$ is hydrogen, $C_1$-$C_{10}$ alkyl, $C_3$-$C_{10}$ alkenyl, phenyl, cycloalkyl, $C_5$-$C_8$ cycloalkenyl, cycloalkyl-substituted $C_1$-$C_3$, alkyl $C_5$-$C_8$ cycloalkyl-substituted $C_1$-$C_3$ alkyl or phenyl-substituted $C_1$-$C_3$ alkyl;

A is $OR^4$ or $NR^5R^6$;

wherein:

$R^4$ is hydrogen, $C_1$-$C_{10}$ alkyl, $C_2$-$C_{10}$ alkenyl, cycloalkyl, $C_5$-$C_8$ cycloalkenyl, cycloalkyl-substituted $C_1$-$C_3$ alkyl, $C_5$-$C_8$ cycloalkenyl-substituted $C_1$-$C_3$ alkyl or phenyl-substituted $C_1$-$C_3$ alkyl;

$R^5$ is hydrogen or $C_1$-$C_3$ alkyl;

$R^6$ is hydrogen, $C_1$-$C_{10}$ alkyl, $C_3$-$C_{10}$ alkenyl, cycloalkyl, phenyl, cycloalkyl-substituted $C_1$-$C_3$ alkyl, $C_5$-$C_8$ cycloalkenyl, $C_5$-$C_8$ cycloalkenyl-substituted $C_1$-$C_3$ alkyl, phenyl-substituted $C_1$-$C_3$ alkyl, or $(CH_2)_q$—B; or $R^5$ and $R^6$ together with N form a saturated non aromatic 4- to 6-membered heterocyclic ring;

B is 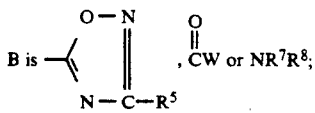, CW or NR⁷R⁸;

R⁷ is hydrogen or $C_1$-$C_3$ alkyl;
R⁸ is hydrogen, $C_1$-$C_{10}$ alkyl, $C_3$-$C_{10}$ alkenyl, cycloalkyl-substituted $C_1$-$C_3$ alkyl, cycloalkyl, $C_5$-$C_8$ cycloalkenyl, $C_5$-$C_8$ cycloalkenyl-substituted $C_1$-$C_3$ alkyl, phenyl or phenyl-substituted $C_1$-$C_3$ alkyl; or
R⁷ and R⁸ together with N form a saturated non aromatic 4- to 6-membered heterocyclic ring;
W is OR⁹, NR¹⁰R¹¹, or OE;
R⁹ is hydrogen, $C_1$-$C_{10}$ alkyl, $C_2$-$C_{10}$ alkenyl, cycloalkyl, $C_5$-$C_8$ cycloalkenyl, cycloalkyl-substituted $C_1$-$C_3$ alkyl, $C_5$-$C_8$ cycloalkenyl-substituted $C_1$-$C_3$ alkyl or phenyl-substituted $C_1$-$C_3$ alkyl;
R¹⁰ is hydrogen or $C_1$-$C_3$ alkyl;
R¹¹ is hydrogen, $C_1$-$C_{10}$ alkyl, $C_3$-$C_{10}$ alkenyl, phenyl, cycloalkyl, $C_5$-$C_8$ cycloalkenyl, cycloalkyl-substituted $C_1$-$C_3$ alkyl, phenyl-substituted $C_1$-$C_3$ alkyl,

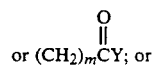

or $(CH_2)_mCY$; or

R¹⁰ and R¹¹ together with N form a saturated non aromatic 4- 6-membered heterocyclic ring;

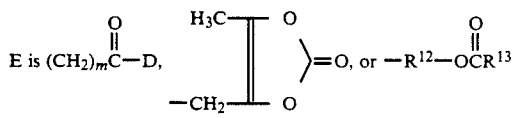

E is $(CH_2)_mC$—D,  ... =O, or —R¹²—OCR¹³

R¹² is $C_1$-$C_3$ alkyl substituted methylene,
R¹³ is $C_1$-$C_{10}$ alkyl;
D is OR¹⁴ or NR¹⁵R¹⁶;
wherein:
R¹⁴ is hydrogen, $C_1$-$C_{10}$ alkyl, $C_2$-$C_{10}$ alkenyl, cycloalkyl, $C_5$-$C_8$ cycloalkenyl, cycloalkyl-substituted $C_1$-$C_3$ alkyl, or $C_5$-$C_8$ cycloalkenyl-substituted $C_1$-$C_3$ alkyl or phenyl-substituted $C_1$-$C_3$ alkyl;
R¹⁵ is hydrogen, $C_1$-$C_{10}$ alkyl, $C_3$-$C_{10}$ alkenyl, phenyl, phenyl-substituted $C_1$-$C_3$ alkyl, cycloalkyl, $C_5$-$C_8$ cycloalkenyl, cycloalkyl-substituted $C_1$-$C_3$ alkyl or $C_5$-$C_8$ cycloalkenyl-substituted $C_1$-$C_3$ alkyl; and
R¹⁶ is hydrogen or $C_1$-$C_3$ alkyl; or
R¹⁵ and R¹⁶ together with N form a saturated non aromatic 4- to 6-membered heterocyclic ring;
Y is OR¹⁷ or NR¹⁸R¹⁹;
R¹⁷ is hydrogen, $C_1$-$C_{10}$ alkyl, $C_2$-$C_{10}$ alkenyl, cycloalkyl, $C_5$-$C_8$ cycloalkenyl, cycloalkyl-substituted $C_1$-$C_3$ alkyl, $C_5$-$C_8$ cycloalkenyl-substituted $C_1$-$C_3$ alkyl, or phenyl-substituted $C_1$-$C_3$ alkyl;
R¹⁸ is hydrogen or $C_1$-$C_3$ alkyl; and
R¹⁹ is hydrogen, $C_1$-$C_{10}$ alkyl, $C_3$-$C_{10}$ alkenyl, phenyl, cycloalkyl, $C_5$-$C_8$ cycloalkenyl, cycloalkyl-substituted $C_1$-$C_3$ alkyl, $C_5$-$C_8$ cycloalkenyl-substituted $C_1$-$C_3$ alkyl, or phenyl-substituted $C_1$-$C_3$ alkyl; or
R¹⁸ and R¹⁹ together with N form a saturated non aromatic 4- to 6-membered heterocyclic ring;

n is 0-;
q is 1-4;
m is 1-4;
or a pharmaceutically acceptable salt thereof.

2. The compound of claim 1 wherein R¹ is hydrogen; R² is $C_1$-$C_3$ alkyl; n=1 or 2; and R³ is benzyl, phenyl, cyclohexyl, or cyclohexylmethyl.

3. The compound of claim 2 wherein A is OR⁴ and R⁴ is hydrogen or $C_1$-$C_3$ alkyl.

4. The compound of claim 2 wherein A is NR⁵R⁶ in which R⁵ is hydrogen and R⁶ is $(CH_2)_q$—B wherein q is 1 to 3 and B is —C(O)W.

5. The compound of claim 4 wherein W is OR⁹ and R⁹ is hydrogen, $C_1$-$C_5$ alkyl, phenyl-substituted $C_1$-$C_2$ alkyl, $C_5$-$C_6$ cycloalkyl, or $C_5$-$C_6$ cycloalkyl-substituted $C_1$-$C_3$ alkyl.

6. The compound of claim 4 wherein W is NR¹⁰R¹¹ in which R¹⁰ is hydrogen or $C_1$-$C_3$ alkyl, and R¹¹ is hydrogen, $C_1$-$C_3$ alkyl or $(CH_2)_mC(O)Y$.

7. The compound of claim 6 wherein m is 1 to 3 and Y is OR¹⁷ or NR¹⁸R¹⁹ wherein R¹⁷, R¹⁸ and R¹⁹ are independently hydrogen or $C_1$-$C_3$ alkyl.

8. The compound of claim 4 wherein W is $OCH_2C(O)OD$ in which D is OR¹⁴ or NR¹⁵R¹⁶ wherein R¹⁴ is hydrogen or $C_1$-$C_3$ alkyl, R¹⁵ is hydrogen and R¹⁶ is methyl or benzyl.

9. The compound of claim 4 wherein W is $OR^{12}OC(O)R^{13}$, wherein R¹² is —CH(CH₃)— or —CH(CH₂CH₃)— and R¹³ is $C_1$-$C_3$ alkyl.

10. The compound of claim 1 wherein the configuration at positions 3 and 4 of the piperidine ring is each R.

11. The compound of claim 1 selected from the group consisting of
QCH₂CH[CH₂(C₆H₅)]C(O)OH,
QCH₂CH₂CH(C₆H₅)C(O)NHCH₂C(O)-OCH₂CH₂, QCH₂CH₂CH(C₆H₅)C(O)NHCH₂C(O)OH, Q-CH₂CH₂CH-(C₆H₅)C(O)NHCH₂C(O)NHCH₃, Q-CH₂CH₂CH(C₆H₅)C(O)NHCH₂C(O)-NHCH₂CH₃, G-NH(CH₂)₂C(O)NH₂, G-NH(CH₂)₂C(O)NHCH₃, G-NHCH₂C(O)NH₂, G-NHCH₂C(O)NHCH₃, G-NHCH₃C(O)NHCH₂CH₃, G-NH(CH₂)₃C(O)OCH₂CH₃, G-NH(CH₂)₃C(O)NHCH₃, G-NH(CH₂)₂C(O)-OH, G-NH(CH₂)₃C(O)OH,
QCH₂CH[CH₂(C₆H₁₁)]C(O)NHCH₂C(O)OH,
QCH₂CH[CH₂(C₆H₁₁)]C(O)NH(CH₂) ₂C(O)OH,
QCH₂CH[CH₂(C₆H₁₁)]-C(O)NH(CH₂)₂C(O)NH₂,
Z-NHCH₂C(O)OCH₂CH₃, Z-NHCH₂C(O)OH, Z-NHCH₂C(O)NH₂, Z-NHCH₂C(O)N(CH₃)₂, Z-NHCH₂C(O)NHCH(CH₃)₂, Z-NHCH₂C(O)OCH₂CH(CH₃)₂, Z-NH(CH₂)₂C(O)OCH₂(C₆H₅), Z-NH-(CH₂C(O)OH, Z-NH(CH₂)₂C(O)NHCH₂CH₃, Z-NH(CH₂)₃C(O)NHCH₃, Z-NHCH₂C(O)NHCH₂C(O)OH, Z-NHCH₂C(O)OCH₂C(O)OCH₃, Z-NHCH₂-C(O)O(CH₂)₄CH₃, Z-NHCH₂C(O)OCH₂-C(O)NHCH₃, Z-NHCH₂C(O)O-( 4-methoxycyclohexyl), Z-NHCH₂C(O)OCH₂-C(O)NHCH₂(C₆H₅), and Z-NHCH₂C(O)OCH(CH₃)OC(O)CH₃, wherein:

Q represents trans-3,4-dimethyl

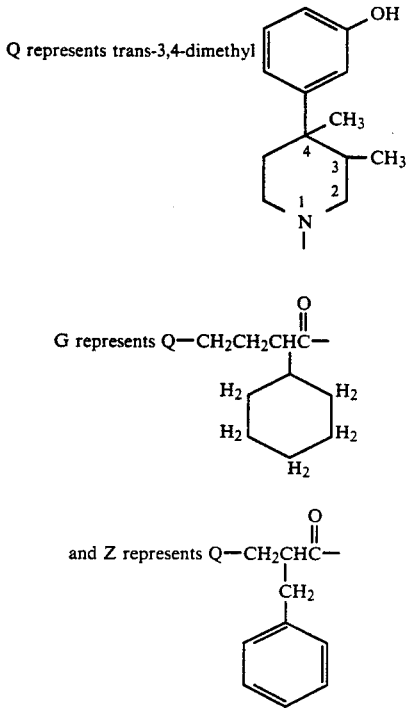

and pharmaceutically acceptable salts thereof.

12. A compound of claim 11 selected from the group consisting of (3R,4R,S)-Z-NHCH$_2$C(O)OCH$_2$CH(CH$_3$)$_2$, (+)Z-NHCH$_2$C(O)OH, (—)Z-NHCH$_2$C(O)OH, (3R,4R,R)-ZNHCH$_2$C(O)-OCH$_2$CH(CH$_3$)$_2$, (3S,4S,S)-ZNHCH$_2$C(O)OCH$_2$CH(CH$_3$)$_2$, (3S,4S,R)-ZNHCH$_2$C(O)OCH$_2$CH(CH$_3$)$_2$, (3R,4R)-ZNHCH$_2$C(O)NHCH$_2$(C$_6$H$_5$) and (3R,4R)-G-NH(CH$_2$)$_3$C(O)OH, and pharmaceutically acceptable salts thereof.

13. A substantially pure stereoisomer of a compound of claim 1 or a pharmaceutically acceptable salt thereof.

14. A pharmaceutical formulation comprising a compound of claim 1 or the salt thereof in combination with a pharmaceutically acceptable excipient.

15. A pharmaceutical formulation comprising a compound of claim 11 or a pharmaceutically acceptable salt thereof in combination with a pharmaceutically acceptable excipient.

16. A method for treating irritable bowel syndrome in a patient said method comprising administering to said patient an effective amount of a compound of claim 1 or a pharmaceutically acceptable salt thereof.

17. A method for binding a peripheral opioid receptor in a patient which comprises administering to said patient an effective amount of a compound of claim 1 or a pharmaceutically acceptable salt thereof.

18. The method of claim 17 wherein said peripheral effect being treated is constipation, nausea or vomiting.

19. A method for blocking mu receptors in mammals comprising administering to a mammal requiring blocking of a mu receptor a receptor blocking dose of a compound of claim 1 or a pharmaceutically acceptable salt thereof.

20. A method for treating idiopathic constipation in a patient said method comprising administering to said patient an effective amount of a compound of claim 1 or a pharmaceutically acceptable salt thereof.

21. A method of claim 16 wherein the compound is one wherein R$^1$ is hydrogen; R$^2$ is C$_1$-C$_3$ alkyl; n=1 or 2; and R$^3$ is benzyl, phenyl, cyclohexyl, or cyclohexylmethyl.

22. A method of claim 21 wherein the compound is one wherein A is NR$^5$R$^6$ and R$^5$ is hydrogen, R$^6$ is (CH$_2$)$_q$—B, q is 1 to 3 and B is —C(O)W.

23. A method of claim 22 wherein the compound is one wherein W is OR$^9$ and R$^9$ is hydrogen, C$_1$-C$_5$ alkyl, phenyl-substituted C$_1$-C$_2$ alkyl, C$_5$-C$_6$ cycloalkyl, or C$_5$-C$_6$ cycloalkyl-substituted C$_1$-C$_3$ alkyl.

24. A method for treating irritable bowel syndrome in a patient comprising administering to the patient an effective amount of a compound of claim 11.

25. A method of claim 24 wherein the compound is selected from the group consisting of (3R,4R,S)-Z-NHCH$_2$C(O)OCH$_2$CH(CH$_3$)$_2$, (+)Z-NHCH$_2$C(O)OH, (—)Z-NHCH$_2$C(O)OH, (3R,4R,R)-ZNHCH$_2$C(O)OCH$_2$CH(CH$_3$)$_2$, (3S,4S,S)-ZNCH$_2$C(O)OCH$_2$CH(CH$_3$)$_2$, (3S,4S,R)-ZNHCH$_2$C(O)OCH$_2$CH-(CH$_3$)$_2$, (3R,4R)-ZNHCH$_2$C(O)NHCH$_2$(C$_6$H$_5$) and (3R,4R)-G-NH(CH$_2$)$_3$C(O)OH.

26. A method of claim 18 wherein the compound is one wherein R$^1$ is hydrogen; R$^2$ is C$_1$-C$_3$ alkyl; n=1 or 2; and R$^3$ is benzyl, phenyl, cyclohexyl, or cyclohexylmethyl.

27. A method of claim 26 wherein the compound is one wherein A is NR$^5$R$^6$ and R$^5$ is hydrogen, R$^6$ is (C$_2$)$_q$—B, q is 1 to 3 and B is —C(O)W.

28. A method of claim 27 wherein the compound is one wherein W is OR$^9$ and R$^9$ is hydrogen, C$_1$-C$_5$ alkyl, phenyl-substituted C$_1$-C$_2$ alkyl, C$_5$-C$_6$ cycloalkyl, or C$_5$-C$_6$ cycloalkyl-substituted C$_1$-C$_3$ alkyl.

29. A method for binding a peripheral opioid receptor in a patient which comprises administering to said patient an effective amount of a compound of claim 11.

30. A method of claim 29 wherein the compound is one selected from the group consisting of (3R,4R,S)-Z-NHCH$_2$C(O)OCH$_2$CH(CH$_3$)$_2$, (+)-NHCH$_2$C(O)OH, (—)Z-NHCH$_2$C(O)OH, (3R,4R,R)-ZNHCH$_2$C(O)OCH$_2$CH(CH$_3$)$_2$, (3S,4S,S)-ZNCH$_2$C(O)OCH$_2$CH(CH$_3$)$_2$, (3S,4S,R)-ZNHCH$_2$C(O)OCH$_2$CH-(CH$_3$)$_2$, (3R,4R)-ZNHCH$_2$C(O)NHCH$_2$(C$_6$H$_5$) and (3R,4R)-G-NH(CH$_2$)$_3$C(O)OH.

31. A method of claim 19 wherein the compound is one wherein R$^1$ is hydrogen; R$^2$ is C$_1$-C$_3$ alkyl; n=1 or 2; and R$^3$ is benzyl, phenyl, cyclohexyl or cyclohexylmethyl.

32. A method of claim 31 wherein the compound is one wherein A is NR$^5$R$^6$ and R$^5$ is hydrogen, R$^6$ is (CH$_2$)$_q$—B, q is 1 to 3 and B is —C(O)W.

33. A method of claim 32 wherein the compound is one wherein W is OR$^9$ and R$^9$ is hydrogen, C$_1$-C$_5$ alkyl, phenyl-substituted C$_1$-C$_2$ alkyl, C$_5$-C$_6$ cycloalkyl, or C$_5$-C$_6$ cycloalkyl-substituted C$_1$-C$_3$ alkyl.

34. A method for blocking a mu receptor in a mammal comprising administering to a mammal requiring blocking of a mu receptor a receptor blocking dose of a compound of claim 11.

35. A method of claim 34 wherein the compound is one selected from the group consisting of (3R,4R,S)-Z-NHCH$_2$C(O)OCH$_2$CH(CH$_3$)$_2$, (+)Z-NHCH$_2$C(O)OH, (—)Z-NHCH$_2$C(O)OH, (3R,4R,R)-ZNHCH$_2$C(O)OCH$_2$CH(CH$_3$)$_2$, (3S,4S,S)-

ZNCH$_2$C(O)OCH$_2$CH(CH$_3$)$_2$, (3S,4S,R)-ZNHCH$_2$C(O)OCH$_2$-CH(CH$_3$)$_2$, (3R,4R)-ZNHCH$_2$C(O)NHCH$_2$(C$_6$H$_5$) and (3R,4R)-G-NH(CH$_2$)$_3$C(O)OH.

36. A method of claim 20 wherein the compound is one wherein R$^1$ is hydrogen; R$^2$ is C$_1$-C$_3$ alkyl; n=1 or 2; and R$^3$ is benzyl, phenyl, cyclohexyl, or cyclohexylmethyl.

37. A method of claim 36 wherein the compound is one wherein A is NR$^5$R$^6$ and R$^5$ is hydrogen, R$^6$ is (CH$_2$)$_q$—B, q is 1 to 3 and B is —C(O)W.

38. A method of claim 37 wherein the compound is one wherein W is OR$^9$ and R$^9$ is hydrogen, C$_1$-C$_5$ alkyl, phenyl-substituted C$_1$-C$_2$ alkyl, C$_5$-C$_6$ cycloalkyl, or C$_5$-C$_6$ cycloalkyl-substituted C$_1$-C$_3$ alkyl.

39. A method for treating idiopathic constipation in a patient comprising administering to the patient an effective amount of a compound of claim 11.

40. A method of claim 39 wherein the compound is one selected from the group consisting of (3R,4R,S)-Z-NHCH$_2$C(O)OCH$_2$CH(CH$_3$)$_2$, (+)Z-NHCH$_2$C(O)OH, (—)Z-NHCH$_2$C(O)OH, (3R,4R,R)-ZNHCH$_2$C(O)OCH$_2$CH(CH$_3$)$_2$, (3S,4S,S)-ZNHCH$_2$C(O)OCH$_2$CH(CH$_3$)$_2$, (3S,4S,R)-ZNHCH$_2$C(O)OCH$_2$CH-(CH$_3$)$_2$, (3R,4R)-ZNHCH$_2$C(O)NHCH$_2$(C$_6$H$_5$) and (3R,4R)-G-NH(CH$_2$)$_3$C(O)OH.

* * * * *

UNITED STATES PATENT AND TRADEMARK OFFICE
CERTIFICATE OF CORRECTION

PATENT NO.   :   5,250,542

DATED        :   October 5, 1993

INVENTOR(S)  :   Buddy E. Cantrell, et al.

It is certified that an error appears in the above-identified patent and that said Letters Patent is hereby corrected as shown below:

Column 2, line 62, delete the term "$\overset{\overset{O}{\|}}{C}Y$" and replace it with $--(CH_2)_n\overset{\overset{O}{\|}}{C}Y--$.

Column 3, line 17, delete the term "$C_{10}-C_{10}$" and replace it with $--(C_1-C_{10})--$.

Column 5, lines 1-12, delete the structure "  " and replace it with  -- -- .

UNITED STATES PATENT AND TRADEMARK OFFICE
CERTIFICATE OF CORRECTION

PATENT NO.   :   5,250,542

DATED        :   October 5, 1993

INVENTOR(S)  :   Buddy E. Cantrell, et al.

It is certified that an error appears in the above-identified patent and that said Letters Patent is hereby corrected as shown below:

Column 7, lines 12-27, delete the structure

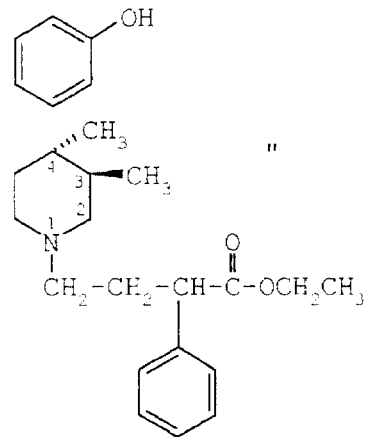

and replace it with

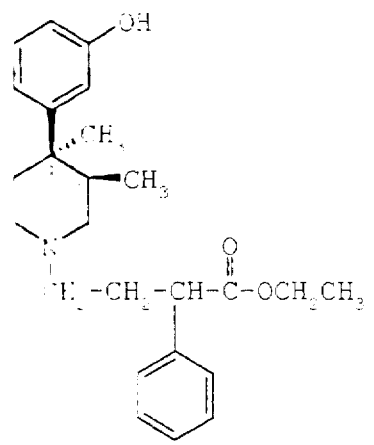

UNITED STATES PATENT AND TRADEMARK OFFICE
CERTIFICATE OF CORRECTION

PATENT NO. : 5,250,542                                    Page 3 of 10

DATED     : October 5, 1993

INVENTOR(S) : Buddy E. Cantrell, et al.

It is certified that an error appears in the above-identified patent and that said Letters Patent is hereby corrected as shown below:

Column 8, line 22, delete the term "pheny)" and replace it with --phenyl)--.

Column 13, line 54, delete the term "$R^8$" and replace it with --$R^3$--.

Column 13, line 66, delete the term "e-methylene" and replace it with --α-methylene--.

Column 14, lines 1-15, delete the structure 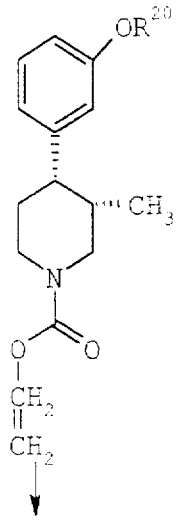

UNITED STATES PATENT AND TRADEMARK OFFICE
CERTIFICATE OF CORRECTION

PATENT NO.    : 5,250,542

DATED         : October 5, 1993

INVENTOR(S)   : Buddy E. Cantrell, et al.

It is certified that an error appears in the above-identified patent and that said Letters Patent is hereby corrected as shown below:

and replace it with -- 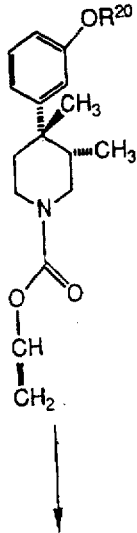 --.

Column 17, line 27, delete the term "1,3,%-trimethyl" and replace it with --1,3,4-trimethyl--.

Column 17, line 48, delete the term "$[\alpha]_{589}$" and replace it with --$[\alpha]_{365}$--.

Column 22, line 47, delete the term "$C_{26}H_{35}N_3O \cdot HCl$ and replace it with --$C_{26}H_{35}N_3O_3 \cdot HCl$--.

Column 22, line 63, delete the term "424 $^++1$" and replace it with --424 $M^++1$--.

UNITED STATES PATENT AND TRADEMARK OFFICE

CERTIFICATE OF CORRECTION

PATENT NO.   :   5,250,542

DATED        :   October 5, 1993

INVENTOR(S)  :   Buddy E. Cantrell, et al.

It is certified that an error appears in the above-identified patent and that said Letters Patent is hereby corrected as shown below:

Column 23, line 7, delete the term "U-NHCH$_3$C(O)-NHCH$_2$CH$_3$·HCl·H$_2$O]" and replace it with --[U-NHCH$_2$C(O)-NHCH$_2$CH$_3$·HCl·H$_2$O]--.

Column 23, line 53, delete the term "[G-NH(CH$_3$)$_2$C(O)NH$_2$·HCl]" and replace it with --[G-NH(CH$_2$)$_2$C(O)NH$_2$·HCl].

Column 25, line 21, delete the term "119°-12° C" and replace it with --119°-124°C--.

Column 27, line 9, delete the term "NHCH$_2$C(O)OCH$_2$CH$_2$·HCl]" and replace it with --NHCH$_2$C(O)OCH$_2$CH$_3$·HCl]--.

Column 28, line 67, delete the term "65.0S" and replace it with --65.05--.

Column 29, line 58, delete the term "C, 6S.91" and replace it with --C, 64.91--.

Column 29, line 59, delete the term "C, 6S.04" and replace it with --65.04--.

Column 30, line 17, delete the term " 6S.86" and replace it with --65.86--.

Column 30, line 53, delete the term "444 M+1" and replace it with --444 M$^+$+1--.

UNITED STATES PATENT AND TRADEMARK OFFICE
CERTIFICATE OF CORRECTION

PATENT NO. : 5,250,542

DATED : October 5, 1993

INVENTOR(S) : Buddy E. Cantrell, et al.

Page 6 of 10

It is certified that an error appears in the above-identified patent and that said Letters Patent is hereby corrected as shown below:

Column 35, line 10, delete the term "[X-O-(CH$_6$H$_{11}$)·HCl]" and replace it with --"[X-O-(C$_6$H$_{11}$)·HCl]".

Column 35, line 34, delete the term "3,%-dimethyl" and replace it with --3,4 dimethyl--.

Column 35, line 36, delete the term "[X-OCH$_2$(CH$_6$H$_{11}$)·HCl]" and replace it with --[X-OCH$_2$(C$_6$H$_{11}$)·HCl]--.

Column 35, line 39, delete the term "(7S0 mg)" and replace it with --(750 mg)--.

Column 36, line 8, delete the term "C$_{298}$" and replace it with --C$_{29}$--.

Column 36, line 17 delete the term "[XOCH$_2$(CH$_6$H$_5$)·HCl]" and replace it with --[XOCH$_2$(C$_6$H$_5$)·HCl]--.

Column 36, line 45, delete the term "[Z-NH(CH$_2$)$_2$C(O)OCH$_2$(CH$_6$H$_5$)·HCl]" and replace it with --[Z-NH(CH$_2$)$_2$C(O)OCH$_2$(C$_6$H$_5$)·HCl]--.

Column 37, line 9, delete the term "Hz" and replace it with --H$_2$--.

Column 38, line 47, delete the term "C$_{26}$" and replace it with --C$_{29}$--.

Column 39, line 1, after the term "HCl" add --·--.

UNITED STATES PATENT AND TRADEMARK OFFICE
CERTIFICATE OF CORRECTION

PATENT NO.    : 5,250,542

DATED         : October 5, 1993

INVENTOR(S)   : Buddy E. Cantrell, et al.

It is certified that an error appears in the above-identified patent and that said Letters Patent is hereby corrected as shown below:

Column 39, line 9, after the term "monohydrochloride" add --. [Z--.

Column 39, line 21, delete the term "C, 66.4" and replace it with --66.44--.

Column 40, line 49, delete the term "C, " and replace it with --C, 63.77--.

Column 42, line 28, delete the term "3,4-dimethyl-" and replace it with --3,4-dimethyl-1- --.

Column 42, line 60, delete the phrase "$[H_2NCH_2C(O)NHCH_2C(O)NHCH_2C(O)NHCH_2-(C_6H_5)]$" and replace it with --$[H_2NCH_2C(O)NHCH_2C(O)NHCH_2-(C_6H_5)]$--.

Column 42, line 64, delete the term "t-butoxycarbon-yl" and replace it with --t-butoxycarbonyl--.

Column 45, lines 25-40, delete the structure " 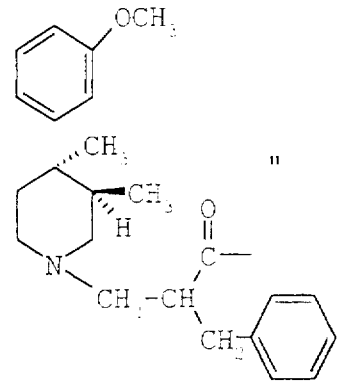 "

UNITED STATES PATENT AND TRADEMARK OFFICE
CERTIFICATE OF CORRECTION

PATENT NO. : 5,250,542           Page 8 of 10

DATED : October 5, 1993

INVENTOR(S) : Buddy E. Cantrell, et al.

It is certified that an error appears in the above-identified patent and that said Letters Patent is hereby corrected as shown below:

and replace it with -- 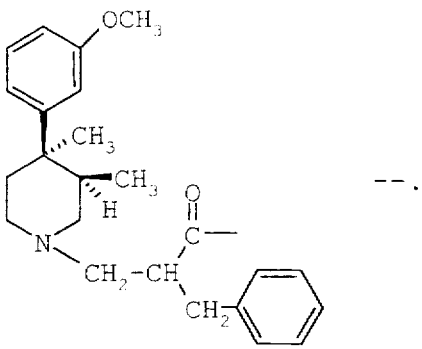 --.

Column 45, line 65, delete the term "(2..72 g) and replace it with --2.72 g)--.

Column 49, line 52, delete the term "218 m9" and replace it with --218 mg--.

Column 49, line 66, delete the term "aceate" and replace it with --acetate--.

Column 51, line 20, delete the term "H, 7.0B;" and replace it with --H, 7.08;--.

Column 51, line 33, delete the term "N$_3$OH" and replace it with --NaOH--.

Column 53, line 11, delete the term "N$_3$OH" and replace it with --NaOH--.

UNITED STATES PATENT AND TRADEMARK OFFICE
CERTIFICATE OF CORRECTION

PATENT NO.   :   5,250,542

DATED        :   October 5, 1993

INVENTOR(S)  :   Buddy E. Cantrell, et al.

It is certified that an error appears in the above-identified patent and that said Letters Patent is hereby corrected as shown below:

Column 53, line 40, delete the term "57-67" and replace it with --57-65--.

Column 53, line 66, delete the term "ms (fd)'424 M$^+$," and replace it with --ms (fd) = 424 M$^+$,--.

Column 55, line 7, delete the term "7.7N 6.32;" and replace it with --7.74 N 6.32;--.

Column 57, line 23, after the graph, insert the following

--(1)   compound tested corresponding to Example Number
  (2)   mg/kg in mouse writhing test
  (3)   mg/kg in mouse distress test
  (4)   ration of AD$_{50}$ to ED
   *    Diastereomer A
  **    Diastereomer B
 ***    I. V. administration because of lack of sample--.

Column 64, line 1, delete the term "0-;" and replace it with --0-4;--.

Column 64, line 46, delete the term "NHCH$_3$C(O)NHCH$_2$CH$_3$," and replace it with -- NHCH$_2$C(O)NHCH$_2$CH$_3$ .

Column 64, line 59, delete the term "(CH$_2$C(O)OH," and replace it with --(CH$_2$)$_2$C(O)OH,--.

UNITED STATES PATENT AND TRADEMARK OFFICE
CERTIFICATE OF CORRECTION

PATENT NO.   : 5,250,542

DATED        : October 5, 1993

INVENTOR(S)  : Buddy E. Cantrell

It is certified that an error appears in the above-identified patent and that said Letters Patent is hereby corrected as shown below:

Column 66, line 22, delete the term "$ZNCH_2C(O)OCH_2CH(CH_3)_2$," and replace it with --$ZNHCH_2C(O)OCH_2CH(CH_3)_2$--.

Column 66, line 32, delete the term "$(C_2)_q-B$," and replace it with --$(CH_2)_q-B$,--.

Column 66, line 45, delete the term "$ZNCH_2C(O)OCH_2CH(CH_3)_2$," and replace it with --$ZNHCH_2C(O)OCH_2CH(CH_3)_2$,--.

Column 67, line 1, delete the term "$ZNCH_2C(O)OCH_2CH(CH_3)_2$," and replace it with --$ZNHCH_2C(O)OCH_2CH(CH_3)_2$,--.

Signed and Sealed this

Twenty-eighth Day of December, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

| | | |
|---|---|---|
| PATENT NO. | : 5,250,542 | |
| APPLICATION NO. | : 07/916783 | |
| DATED | : October 5, 1993 | |
| INVENTOR(S) | : Buddy E. Cantrell et al. | |

It is certified that error appears in the above-identified patent and that said Letters Patent is hereby corrected as shown below:

In Column 64, Line 39, please change "$OCH_2CH_2$" to --$OCH_2CH_3$--.

Signed and Sealed this

Twenty-sixth Day of June, 2007

JON W. DUDAS
*Director of the United States Patent and Trademark Office*